United States Patent [19]
Cone et al.

[11] Patent Number: 6,100,048
[45] Date of Patent: Aug. 8, 2000

[54] METHODS AND REAGENTS FOR DISCOVERING AND USING MAMMALIAN MELANOCORTIN RECEPTOR AGONISTS AND ANTAGONISTS TO MODULATE FEEDING BEHAVIOR IN ANIMALS

[75] Inventors: Roger D. Cone, Oregon City; Wei Fan, Portland; Bruce A. Boston, Lake Oswego; Robert A. Kesterton, Portland; Dongsi Lu, Beaverton; Wenbiao Chen, Portland, all of Oreg.

[73] Assignee: Oregon Health Sciences University, Portland, Oreg.

[21] Appl. No.: 08/706,281

[22] Filed: Sep. 4, 1996

Related U.S. Application Data

[63] Continuation-in-part of application No. 08/466,906, Jun. 6, 1995, Pat. No. 5,849,871, application No. 08/478,992, Jun. 7, 1995, Pat. No. 5,773,229, and application No. 08/044,812, Apr. 8, 1993, Pat. No. 5,837,521, said application No. 08/466,906, is a division of application No. 07/886,979, May 21, 1992, Pat. No. 5,270,605, said application No. 08/478,992, is a division of application No. 07/866,560, Apr. 10, 1992, Pat. No. 5,280,112.

[51] Int. Cl.$^7$ .......................... G01N 33/566; C12N 5/10; C12N 15/10; C07K 14/71

[52] U.S. Cl. .................. 435/7.21; 530/350; 530/306; 530/312; 435/69.1; 435/325; 536/23.5

[58] Field of Search .................. 435/7.21, 69.1, 435/325; 530/350, 306, 312; 536/23.5

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91 |
| 5,280,112 | 1/1994 | Cone et al. | 536/23.5 |
| 5,532,347 | 7/1996 | Cone et al. | 536/23.5 |
| 5,556,753 | 9/1996 | Bard et al. | 435/6 |
| 5,622,860 | 4/1997 | Yamada et al. | 435/252.3 |

FOREIGN PATENT DOCUMENTS

WO 93/21315  10/1993  WIPO.
WO 93/21316  10/1993  WIPO.

OTHER PUBLICATIONS

Gantz et al., Molecular cloning, expression, and gene localization of a fourth melanocortin receptor, J. Biol. Chem., 268(20): 15174–15179, Jul. 15, 1993.

Chhajlani et al., Molecular cloning of a novel human melanocortin receptor, 195(2): 866–873, Sep. 15, 1993.

Gantz et al., Molecular cloning, expression, and characterization of a fifth melanocortin receptor, Biochem. Biophys. Res. Comm., 200(3): 1214–1220, May 16, 1994.

Hodgson, J., Receptor screening and the search for new pharmaceuticals, Bio/Technol., 10:973–977, Sep. 1992.

Ahmed et al., "Isolation and partial purification of a melanocyte–stimulating hormone receptor from B16 murine melanoma cells. A novel approach using a cleavable biotinylated photoactivated ligand and streptavidin–coated magnetic beads," *The Biochemical Journal* 286:377–382 (Sep. 1, 1992).

Bergendahl et al., "Short–Term Starvation Decreases POMC mRNA but Does Not Alter GnRH mRNA in the Brain of Adult Male Rats," *Neuroendocrinol.* 56:913–920 (1992).

Bertling, "Transfection of a DNA/Protein Complex into Nuclei of Mammalian Cells Using Polyoma Capsids and Electroporation," *Bioscience Reports* 7:107–112 (1987).

Bost et al., "Molecular characterization of a corticotropin receptor," *Molecular and Cellular Endocrinology* 44:1–9 (1986).

Bost et al., "Similarity between the corticotropin (ACTH) receptor and a peptide encoded by an RNA that is complementary to ACTH mRNA," *PNAS* 82:1372–1375 (Mar. 1985).

Brady et al., "Altered Expression of Hypothalamic Neuropeptide mRNAs in Food–Restricted and Food–Deprived Rats," *Neuroendocrinol.* 52:441–447 (1990).

Buckley & Ramachandran, "Characterization of corticotropin receptors on adrenocortical cells," *Proc. Natl. Acad. Sci. USA* 78:7431–7435 (1981).

Chen & Okayama, "High–Efficiency Transformation of Mammalian Cells by Plasmid DNA," *Mol. Cell. Biol.* 7:2745–2752 (1987).

Chen et al., "A Colorimetric Assay for Measuring Activation of $G_s$– and $G_q$–Coupled Signaling Pathways," *Analyt. Biochem.* 226:349–354 (1995).

Chhajlani et al., "Molecular cloning and expression of the human melanocyte stimulating hormone receptor cDNA," *FEBS Letters* 309(3):417–420 (Sep. 14, 1992).

Chirgwin et al., "Isolation of Biologically Active Ribonucleic Acid for Sources Enriched in Ribonuclease," *Biochemistry* 18:5294–5299 (1979).

DeWied & Jolles, "Neuropeptides derived from pro–opiocortin: Behavioral, physiological and neurochemical effects," *Physiol. Rev.* 62:976–1059 (1982).

(List continued on next page.)

*Primary Examiner*—Lila Feisee
*Assistant Examiner*—Claire M. Kaufman
*Attorney, Agent, or Firm*—McDonnell Boehnen Hulbert & Berghoff

[57] ABSTRACT

The present invention provides recombinant expression constructs comprising nucleic acid encoding mammalian melanocortin receptors, and mammalian cells into which said recombinant expression constructs have been introduced that express functional mammalian melanocortin receptors. The invention provides a panel of such transformed mammalian cells expressing melanocortin receptors for screening compounds for receptor agonist and antagonist activity. The invention also provides methods for using such panels of melanocortin receptor-expressing mammalian cells to specifically detect and identify agonists and antagonists for each melanocortin receptor, as well as patterns of agonist and antagonist activity of said compounds for the class of melanocortin receptors. Such screening methods provide a means for identifying compounds with patterns of melanocortin agonist and antagonist activity which are associated with the capacity to influence or modify metabolism and behavior, particularly feeding behavior.

21 Claims, 46 Drawing Sheets

OTHER PUBLICATIONS

Dixon et al., "Structural features required for ligand binding to the β–adrenergic receptor," *EMBO J.* 6:3269–3275 (1987).

Eberle et al., "Receptor–specific antibodies by immunization with 'antisense' peptides?," *Peptide Research* 2(3):213–220 (1989).

Felgner et al., "Enhanced Gene Delivery and Mechanism Studies with a Novel Series of Cationic Lipid Formulations," *J. Biol. Chem.* 269:2550–2561 (1994).

Fink et al., "The CGTCA sequence motif is essential for biological activity of the vasoactive intestinal peptide gene cAMP–regulated enhancer," *Proc. Natl. Acad. Sci. USA* 85:6662–6666 (1988).

Gantz et al., "Molecular Cloning of a Novel Melanocortin Receptor," *J. Biol. Chem.* 268:8246–8250 (1993).

Gerst et al., "Dual Regulation of β–Melanotropin Receptor Function and Adenylate Cyclase by Calcium and Guanosine Nucleotides in the M2r Melanoma Cell Line," *Mol. Pharmacol.* 31:81–88 (1987).

Gilman, "A Protein Binding Assay for Adenosine 3':5'–Cyclic Monophosphate," *Proc. Natl. Acad. Sci. USA* 67:305–312 (1979).

Grahame–Smith et al., "Adenosine 3':5'–Monophosphate as the Intracellular Mediator of the Action of Adrenocorticotropic Hormone on the Adrenal Cortex," *J. Biol. Chem.* 242:5535–5541 (1967).

Gruber & Callahan, "ACTH–(4–10) through gamma–MSH: evidence for a new class of central autonomoic nervous system–regulating peptides," *Am. Physiol. Soc.* 257:R681–R694 (1989).

Hanneman et al., "Peptides encoded by the pro–opiomelanocortin gene," *Peptide Hormone as Prohormones*, G. Martinez, ed. (Ellis Horwood Ltd.: Chichester, UK) pp. 53–82 (1987).

Hofmann et al., "Radioactive probes for adrenocorticotropic hormone receptors," *Biochemistry* 25(6):1339–1346 (Mar. 25, 1986).

Hruby et al., "Cyclic Lactam α–Melanotropin Analogues of Ac–Nle$^4$–cyclo[Asp$^5$,D–Phe$^7$,Lys$^{10}$]α–Melanocyte–Stimulating Hormone–(4–10)–NH$_2$ with Bulky Aromatic Amino Acids at Position 7 Show High Antagonist Potency and Selectivity at Specific Melanocortin Receptors," *J. Med. Chem.* 38:3454–3461 (1995).

Kameyama et al., "Expression of melanocyte stimulating hormone receptors correlates with mammalian pigmentation, and can be modulated by interferons," *J. Cellular Physiology* 137(1):35–44 (Oct. 1988).

Karnik et al., "Cysteine residues 110 and 187 are essential for the formation of correct structure in bovine rhodopsin," *Proc. Natl. Acad. Sci. USA* 85:8459–8463 (1988).

Klein et al., "Pressor and cardioaccelerator effects of gamma MSH and related peptides," *Life Sci.* 36:769–775 (1985).

Labbe et al., "Molecular Cloning of a Mouse Melanocortin 5 Receptor Gene Widley Expressed in Peripheral Tissues," *Biochem.* 33:4543–4549 (1994).

Laursen and Belknap, "Intracerebroventricular Injections in Mice," *J. Pharmacol. Methods* 16:355–357 (1986).

Leiba et al., "The melanocortin receptor in the rat lacrimal gland: a model system for the study of MSH (melanocyte stimulating hormone) as a potential neurotransmitter," *European Journal of Pharmacology* 181(1–2):71–82 (May 31, 1990).

Libert et al., "Selective Amplification and Cloning of Four New Members of the G Protein–Coupled Receptor Family," *Science* 244:569 (1989).

Lin et al., "A γ–melanocyte stimulating hormone–like peptide causes reflex natriuresis after acute unilaterasl nephrectomy," *Hypertension* 10:619–627 (1987).

Ling et al., "Synthesis and biological activity of four gamma–melanotropin peptides derived from the cryptic region of the adrenocorticotropin/β–lipotropin precursor," *Life Sci.* 25:1773–1780 (1979).

Lu et al., "Agouti protein is an antagonist of the melanocyte–stimulating–hormone receptor," *Nature* 371:799–802 (1994).

Masu et al., "cDNA cloning of bovine substance–K receptor through oocyte expression system," *Nature* 329:836–838 (1987).

Matsuda et al., "Structure of a cannabinoid receptor and functional expression of the cloned cDNA," *Nature* 346:561–564 (1990).

Mertz et al., "Adrenocorticotropin receptors: Functional expression from rat adrenal mRNA in *Xenopus laevis* oocytes," *PNAS* 88:8525–8529 (1991).

Moore et al., *Endocrinology*, 34:107–114 (1991).

Mountjoy et al., "Localization of the Melanocortin–4 Receptor (MC4–R) in Neuroendocrine and Autonomic Control Circuits in the Brain," *Mole. Endocrinol.* 8:1298–1308 (1994).

Mountjoy et al., "The cloning of a family of genes that encode the melanocortin receptors," *Science* 257:1248–1251 (1992).

Oelofsen & Ramachandran, "Studies of Corticotropin Receptors on Rat Adipocytes," *Arch. Biochem. Biophys.* 225:414–421 (1983).

Oki et al., "γ–MSH Fragments from ACTH–β–LPH Precursor Have an Affinity for Opiate Receptors," *Eur. J. Pharmacol.* 64:161–164 (1980).

Pawalek, "Studies on the Cloudman Melanoma Cell Line as a Model for the Action of MSH," *Yale J. Biol. Med.* 58:571–578 (1985).

Pawelek, "Factors Regulating Growth and Pigmentation of Melanoma Cells," *J. Invest. Dermatol.* 66:201–209 (1976).

Roselli–Rehfuss et al., "Identification of a receptor for γ melanotropin and other proopiomelanocortin peptides in the hypothalamus and limbic system," *Proc. Natl. Acad. Sci. USA* 90:8856–8860 (1993).

Saiki et al., "Primer–Directed Enzymatic Amplification of DNA with a Thermostable DNA Polymerase," *Science* 239:487–491 (1988).

Sambrook et al., 1990, *Molecular Cloning: A Laboratory Manual* (Cold Spring Harbor Press: New York).

Sanger et al., "DNA sequencing with chain–terminating inhibitors," *Proc. Natl. Acad. Sci. USA* 74:5463–6567 (1977).

Schild, "pA, A New Scale for the Measurement of Drug Antagonism," *Brit J. Pharmacol.* 2:189–206 (1947).

Schimmer et al., "Adrenocorticotropin–Resistant Mutants of the Y1 Adrenal Cell Line Fail to Express the Adrenocorticotropin Receptor," *J. Cell Physiol.* 163:164–171 (1995).

Schimuze, "Thirty–five years of progress in the study of MSH," *Yale J. Biol. Med.* 58:561–570 (1985).

Shimizu et al., "Effects of MSH on Food Intake, Body Weight and Coat Color of the Yellow Obese Mouse," *Life Sci.* 45:543–552 (1989).

Siegrist et al., "Characterization of Receptors for α–Melanocyte–stimulating Hormone on Human Melanoma Cells," *Cancer Research* 49:6352–6358 (Nov. 15, 1989).

Siegrist et al., "Quantification of MSH receptors on mouse melanoma tissue by receptor autoradiography," *J. Receptor Res.* 11:323–331 (1991).

Slominski et al., "Melanotropic activity of gamma MSH peptides in melanoma cells," *Life Sci.* 50:1103–1108 (1992).

Smithies et al., "Insertion of DNA sequences into the human chromosomal β–globin locus by homologous recombination," *Nature* 317:230–234 (1985).

Solca et al., "The receptor for α–melanotropin of mouse and human melanoma cells," *J. Biol. Chem.* 264:14277–14280 (1989).

Spindel et al., "Cloning and Functional Characterization of a Complementary DNA Encoding the Murine Fibroblast Bobmesin/Gastrin–Releasing Peptide Receptor," *Mol. Endocrinol.* 4:1956–1963 (1990).

Tatro & Reichlin, "Specific receptors for α–melanocyte–stimulating hormone are widely distributed in tissues of rodents," *Endocrinology* 121:1900–1907 (1987).

Tatro et al., "Melanotropin Receptors of Murine Melanoma Characterized in Cultured Cells and Demonstrated in Experimental Tumors in Situ," *Cancer Res.* 50:1237–1242 (1990).

Thomas & Capecchi, "Site–Directed Mutagenesis by Gene Targeting in Mouse Embryo–Derived Stem Cells," *Cell* 51:503–512 (1987).

*Tissue Culture*, Academic Press, Kruse & Patterson, editors (1973).

Tsujii et al., "Acetylation Alters the Feeding Response to MSH and Beta–Endorphin," *Brian Res. Bull.* 23:165–169 (1989).

Yen et al., "Obesity, diabetes, and neoplasia in yellow $A^{vy}$/–mice: ectopic expression of the *agouti* gene," *FASEB J.* 8:479–488 (1994).

Zhou et al., "Cloning and expression of human and rat $D_1$ dopamine receptors," *Nature* 347:76–80 (Sep. 1990).

FIG. 1A

| | |
|---|---|
| TTCCTGACAA GACT ATG TCC ACT CAG GAG CCC CAG AAG AGT CTT CTG GGT<br>                      Met Ser Thr Gln Glu Pro Gln Lys Ser Leu Leu Gly<br>                       1                     5                      10 | 50 |
| TCT CTC AAC TCC AAT GCC ACC TCT CAC CTT GGA CTG GCC ACC AAC CAG<br>Ser Leu Asn Ser Asn Ala Thr Ser His Leu Gly Leu Ala Thr Asn Gln<br>         15                    20                   25 | 98 |
| TCA GAG CCT TGG TGC CTG TAT GTG TCC ATC CCA GAT GGC CTC TTC CTC<br>Ser Glu Pro Trp Cys Leu Tyr Val Ser Ile Pro Asp Gly Leu Phe Leu<br>      30                     35                  40 | 146 |
| AGC CTA GGG CTG GTG AGT CTG GTG GAG AAT GTG CTG GTT GTG ATA GCC<br>Ser Leu Gly Leu Val Ser Leu Val Glu Asn Val Leu Val Val Ile Ala<br>45                50                   55                 60 | 194 |
| ATC ACC AAA AAC CGC AAC CTG CAC TCG CCC ATG TAT TAC TTC ATC TGC<br>Ile Thr Lys Asn Arg Asn Leu His Ser Pro Met Tyr Tyr Phe Ile Cys<br>               65                    70                   75 | 242 |
| TGC CTG GCC CTG TCT GAC CTG ATG GTA AGT GTC AGC ATC GTG CTG GAG<br>Cys Leu Ala Leu Ser Asp Leu Met Val Ser Val Ser Ile Val Leu Glu<br>             80                    85                90 | 290 |
| ACT ACT ATC ATC CTG CTG CTG GAG GTG GGC ATC CTG GTG GCC AGA GTG<br>Thr Thr Ile Ile Leu Leu Leu Glu Val Gly Ile Leu Val Ala Arg Val<br>        95                    100                105 | 338 |
| GCT TTG GTG CAG CAG CTG GAC AAC CTC ATT GAC GTG CTC ATC TGT GGC<br>Ala Leu Val Gln Gln Leu Asp Asn Leu Ile Asp Val Leu Ile Cys Gly<br>      110                  115                120 | 386 |
| TCC ATG GTG TCC AGT CTC TGC TTC CTG GGC ATC ATT GCT ATA GAC CGC<br>Ser Met Val Ser Ser Leu Cys Phe Leu Gly Ile Ile Ala Ile Asp Arg<br>125              130                   135                140 | 434 |
| TAC ATC TCC ATC TTC TAT GCG CTG CGT TAT CAC AGC ATC GTG ACG CTG<br>Tyr Ile Ser Ile Phe Tyr Ala Leu Arg Tyr His Ser Ile Val Thr Leu<br>               145                  150              155 | 482 |
| CCC AGA GCA CGA CGG GCT GTC GTG GGC ATC TGG ATG GTC AGC ATC GTC<br>Pro Arg Ala Arg Arg Ala Val Val Gly Ile Trp Met Val Ser Ile Val<br>         160                  165                170 | 530 |

FIG. 1B

```
TCC AGC ACC CTC TTT ATC ACC TAC TAC AAG CAC ACA GCC GTT CTG CTC       578
Ser Ser Thr Leu Phe Ile Thr Tyr Tyr Lys His Thr Ala Val Leu Leu
        175                 180                 185

TGC CTC GTC ACT TTC TTT CTA GCC ATG CTG GCA CTC ATG GCG ATT CTG       626
Cys Leu Val Thr Phe Phe Leu Ala Met Leu Ala Leu Met Ala Ile Leu
        190                 195                 200

TAT GCC CAC ATG TTC ACG AGA GCG TGC CAG CAC GTC CAG GGC ATT GCC       674
Tyr Ala His Met Phe Thr Arg Ala Cys Gln His Val Gln Gly Ile Ala
205                 210                 215                 220

CAG CTC CAC AAA AGG CGG CGG TCC ATC CGC CAA GGC TTC TGC CTC AAG       722
Gln Leu His Lys Arg Arg Arg Ser Ile Arg Gln Gly Phe Cys Leu Lys
                225                 230                 235

GGT GCT GCC ACC CTT ACT ATC CTT CTG GGG ATT TTC TTC CTG TGC TGG       770
Gly Ala Ala Thr Leu Thr Ile Leu Leu Gly Ile Phe Phe Leu Cys Trp
            240                 245                 250

GGC CCC TTC TTC CTG CAT CTC TTG CTC ATC GTC CTC TGC CCT CAG CAC       818
Gly Pro Phe Phe Leu His Leu Leu Leu Ile Val Leu Cys Pro Gln His
            255                 260                 265

CCC ACC TGC AGC TGC ATC TTC AAG AAC TTC AAC CTC TTC CTC CTC CTC       866
Pro Thr Cys Ser Cys Ile Phe Lys Asn Phe Asn Leu Phe Leu Leu Leu
        270                 275                 280

ATC GTC CTC AGC TCC ACT GTT GAC CCC CTC ATC TAT GCT TTC CGC AGC       914
Ile Val Leu Ser Ser Thr Val Asp Pro Leu Ile Tyr Ala Phe Arg Ser
285                 290                 295                 300

CAG GAG CTC CGC ATG ACA CTC AAG GAG GTG CTG CTG TGC TCC TGG            959
Gln Glu Leu Arg Met Thr Leu Lys Glu Val Leu Leu Cys Ser Trp
                305                 310                 315

TGATCAGAGG GCGCTGGGCA GAGGGTGACA GTGATATCCA GTGGCCTGCA TCTGTGAGAC    1019

CACAGGTACT CATCCCTTCC TGATCTCCAT TTGTCTAAGG GTCGACAGGA TGAGCTTTAA    1079

AATAGAAACC CAGAGTGCCT GGGGCCAGGA GAAAGGGTAA CTGTGACTGC AGGGCTCACC    1139

CAGGGCAGCT ACGGGAAGTG GAGGAGACAG GGATGGGAAC TCTAGCCCTG AGCAAGGGTC    1199

AGACCACAGG CTCCTGAAGA GCTTCACCTC TCCCCACCTA CAGGCAACTC CTGCTCAAGC    1259

```
CCCGCATGTG GCCGCCCTCA ATGGAGGGCT CTGAGAACGA CTTTTAAAAC GCAGAGAAAA        60

AGCTCCATTC TTCCCAGACC TCAGCGCAGC CCTGGCCCAG GAAGGGAGGA GACAGAGGCC       120

AGGACGGTCC AGAGGTGTCG AAATGTCCTG GGAACCTGAG CAGCAGCCAC CAGGGAAGAG       180

GCAGGGAGGG AGCTGAGGAC CAGGCTTGGT TGTGAGAATC CCTGAGCCCA GGCGGTTGAT       240

GCCAGGAGGT GTCTGGACTG GCTGGGCCAT GCCTGGGCTG ACCTGTCCAG CCAGGGAGAG       300

GGTGTGAGGG CAGATCTGGG GGTGCCCAGA TGGAAGGAGG CAGGCATGGG GACACCCAAG       360

GCCCCCTGGC AGCACCATGA ACTAAGCAGG ACACCTGGAG GGGAAGAACT GTGGGGACCT       420

GGAGGCCTCC AACGACTCCT TCCTGCTTCC TGGACAGGAC T ATG GCT GTG CAG           473
                                              Met Ala Val Gln
                                               1
```

| Codons | Amino Acids | Pos |
|---|---|---|
| GGA TCC CAG AGA AGA CTT CTG GGC TCC CTC AAC TCC ACC CCC ACA GCC | Gly Ser Gln Arg Arg Leu Leu Gly Ser Leu Asn Ser Thr Pro Thr Ala | 521 |
|  | 5      10      15      20 |  |
| ATC CCC CAG CTG GGG CTG GCT GCC AAC CAG ACA GGA GCC CGG TGC CTG | Ile Pro Gln Leu Gly Leu Ala Ala Asn Gln Thr Gly Ala Arg Cys Leu | 569 |
|  | 25      30      35 |  |
| GAG GTG TCC ATC TCT GAC GGG CTC TTC CTC AGC CTG GGG CTG GTG AGC | Glu Val Ser Ile Ser Asp Gly Leu Phe Leu Ser Leu Gly Leu Val Ser | 617 |
|  | 40      45      50 |  |
| TTG GTG GAG AAC GCG CTG GTG GTG GCC ACC ATC GCC AAG AAC CGG AAC | Leu Val Glu Asn Ala Leu Val Val Ala Thr Ile Ala Lys Asn Arg Asn | 665 |
|  | 55      60      65 |  |
| CTG CAC TCA CCC ATG TAC TGC TTC ATC TGC TGC CTG GCC TTG TCG GAC | Leu His Ser Pro Met Tyr Cys Phe Ile Cys Cys Leu Ala Leu Ser Asp | 713 |
|  | 70      75      80 |  |
| CTG CTG GTG AGC GGG ACG AAC GTG CTG GAG ACG GCC GTC ATC CTC CTG | Leu Leu Val Ser Gly Thr Asn Val Leu Glu Thr Ala Val Ile Leu Leu | 761 |
|  | 85      90      95      100 |  |
| CTG GAG GCC GGT GCA CTG GTG GCC CGG GCT GCG GTG CTG CAG CAG CTG | Leu Glu Ala Gly Ala Leu Val Ala Arg Ala Ala Val Leu Gln Gln Leu | 809 |
|  | 105      110      115 |  |
| GAC AAT GTC ATT GAC GTG ATC ACC TGC AGC TCC ATG CTG TCC AGC CTC | Asp Asn Val Ile Asp Val Ile Thr Cys Ser Ser Met Leu Ser Ser Leu | 857 |
|  | 120      125      130 |  |
| TGC TTC CTG GGC GCC ATC GCC GTG GAC CGC TAC ATC TCC ATC TTC TAC | Cys Phe Leu Gly Ala Ile Ala Val Asp Arg Tyr Ile Ser Ile Phe Tyr | 905 |
|  | 135      140      145 |  |
| GCA CTG CGC TAC CAC AGC ATC GTG ACC CTG CCG CGG GCG CCG CGA GCC | Ala Leu Arg Tyr His Ser Ile Val Thr Leu Pro Arg Ala Pro Arg Ala | 953 |
|  | 150      155      160 |  |

FIG. 2B

```
GTT GCG GCC ATC TGG GTG GCC AGT GTC GTC TTC AGC ACG CTC TTC ATC        1001
Val Ala Ala Ile Trp Val Ala Ser Val Val Phe Ser Thr Leu Phe Ile
165             170             175             180

GCC TAC TAC GAC CAC GTG GCC GTC CTG CTG TGC CTC GTG GTC TTC TTC        1049
Ala Tyr Tyr Asp His Val Ala Val Leu Leu Cys Leu Val Val Phe Phe
                185             190             195

CTG GCT ATG CTG GTG CTC ATG GCC GTG CTG TAC GTC CAC ATG CTG GCC        1097
Leu Ala Met Leu Val Leu Met Ala Val Leu Tyr Val His Met Leu Ala
            200             205             210

CGG GCC TGC CAG CAC GCC CAG GGC ATC GCC CGG CTC CAC AAG AGG CAG        1145
Arg Ala Cys Gln His Ala Gln Gly Ile Ala Arg Leu His Lys Arg Gln
        215             220             225

CGC CCG GTC CAC CAG GGC TTT GGC CTT AAA GGC GCT GTC ACC CTC ACC        1193
Arg Pro Val His Gln Gly Phe Gly Leu Lys Gly Ala Val Thr Leu Thr
    230             235             240

ATC CTG CTG GGC ATT TTC TTC CTC TGC TGG GGC CCC TTC TTC CTG CAT        1241
Ile Leu Leu Gly Ile Phe Phe Leu Cys Trp Gly Pro Phe Phe Leu His
245             250             255             260

CTC ACA CTC ATC GTC CTC TGC CCC GAG CAC CCC ACG TGC GGC TGC ATC        1289
Leu Thr Leu Ile Val Leu Cys Pro Glu His Pro Thr Cys Gly Cys Ile
            265             270             275

TTC AAG AAC TTC AAC CTC TTT CTC GCC CTC ATC ATC TGC AAT GCC ATC        1337
Phe Lys Asn Phe Asn Leu Phe Leu Ala Leu Ile Ile Cys Asn Ala Ile
        280             285             290

ATC GAC CCC CTC ATC TAC GCC TTC CAC AGC CAG GAG CTC CGC AGG ACG        1385
Ile Asp Pro Leu Ile Tyr Ala Phe His Ser Gln Glu Leu Arg Arg Thr
    295             300             305

CTC AAG GAG GTG CTG ACA TGC TCC TGG TGAGCGCGGT GCACGCGCTT             1432
Leu Lys Glu Val Leu Thr Cys Ser Trp
310             315

TAAGTGTGCT GGGCAGAGGG AGGTGGTGAT ATTGTGGTCT GGTTCCTGTG TGACCCTGGG     1492

CAGTTCCTTA CCTCCCTGGT CCCCGTTTGT CAAAGAGGAT GGACTAAATG ATCTCTGAAA     1552

GTGTTGAAGC GCGGACCCTT CTGGGCAGGG AGGGGTCCTG CAAAACTCCA GGCAGGACTT     1612

CTCACCAGCA GTCGTGGGAA C                                              1633
```

FIG. 3A

| | |
|---|---|
| ACAACACTTT ATATATATTT TTATAAATGT AAGGGGTACA AAGGTGCCAT TTTGTTACAT | 60 |
| GGATATACCG TGTAGTGGTG AAGCCTGGGC TTTTAGTGTA TCTGTCATCA GAATAACATA | 120 |
| CGTGTTACCC ATAGGAATTT CTCATCACCC GCCCCCTCCA CCCTTCGAGT CTCCAATGTC | 180 |
| CATTCCACAC TCTATATCCA CGTGTATGCA TATAGCTCCA CATATAAGTG AGAACATGTA | 240 |
| GTATTTGACT TCCTCTTTCT GAGTTATTTC ACTTTGATAA TGGCCTCCAC TTCCATCCAT | 300 |
| GTTGCTGCAA AAGACATGAC CTTATTCTTT TTGATAGCTG GGAGTACTC CATTGTGTAT | 360 |
| ATGTACCACA TTTCTTTATC CATTCACCCA TTGAGAACAC TTAGTTGATT CCATATCTTT | 420 |
| GCTATTGTCA CTAGTGCTGC AATAAACATA CATGTGCAGG CTCCTTCTAA TATACTGATT | 480 |
| TATATTTTAT GGAGAGAGAT AGAGTTCTTA GCGAGTGTGC TGTTTATTTC TAGTGTACTT | 540 |
| GCAACTAATA TTCTGTATAC TCCCTTTAGG TGATTGGAGA TTTAACTTAG ATCTCCAGCA | 600 |
| AGTGCTACAA GAAGAAAAGA TCCTGAAGAA TCAATCAAGT TTCCGTGAAG TCAAGTCCAA | 660 |
| GTAACATCCC CGCCTTAACC ACAAGCAGGA GAA ATG AAG CAC ATT ATC AAC TCG | 714 |
|                                                                  Met Lys His Ile Ile Asn Ser<br>                                                                   1                5 | |
| TAT GAA AAC ATC AAC AAC ACA GCA AGA AAT AAT TCC GAC TGT CCT CGT<br>Tyr Glu Asn Ile Asn Asn Thr Ala Arg Asn Asn Ser Asp Cys Pro Arg<br>            10                       15                      20 | 762 |
| GTG GTT TTG CCG GAG GAG ATA TTT TTC ACA ATT TCC ATT GTT GGA GTT<br>Val Val Leu Pro Glu Glu Ile Phe Phe Thr Ile Ser Ile Val Gly Val<br>      25                           30                        35 | 810 |
| TTG GAG AAT CTG ATC GTC CTG CTG GCT GTG TTC AAG AAT AAG AAT CTC<br>Leu Glu Asn Leu Ile Val Leu Leu Ala Val Phe Lys Asn Lys Asn Leu<br>40                            45                        50                      55 | 858 |
| CAG GCA CCC ATG TAC TTT TTC ATC TGT AGC TTG GCC ATA TCT GAT ATG<br>Gln Ala Pro Met Tyr Phe Phe Ile Cys Ser Leu Ala Ile Ser Asp Met<br>                    60                       65                       70 | 906 |
| CTG GGC AGC CTA TAT AAG ATC TTG GAA AAT ATC CTG ATC ATA TTG AGA<br>Leu Gly Ser Leu Tyr Lys Ile Leu Glu Asn Ile Leu Ile Ile Leu Arg<br>                   75                       80                       85 | 954 |
| AAC ATG GGC TAT CTC AAG CCA CGT GGC AGT TTT GAA ACC ACA GCC GAT<br>Asn Met Gly Tyr Leu Lys Pro Arg Gly Ser Phe Glu Thr Thr Ala Asp<br>                   90                       95                      100 | 1002 |
| GAC ATC ATC GAC TCC CTG TTT GTC CTC TCC CTG CTT GGC TCC ATC TTC<br>Asp Ile Ile Asp Ser Leu Phe Val Leu Ser Leu Leu Gly Ser Ile Phe<br>                  105                     110                     115 | 1050 |

FIG. 3B

```
AGC CTG TCT GTG ATT GCT GCG GAC CGC TAC ATC ACC ATC TTC CAC GCA    1098
Ser Leu Ser Val Ile Ala Ala Asp Arg Tyr Ile Thr Ile Phe His Ala
120                 125                 130                 135

CTG CGG TAC CAC AGC ATC GTG ACC ATG CGC CGC ACT GTG GTG GTG CTT    1146
Leu Arg Tyr His Ser Ile Val Thr Met Arg Arg Thr Val Val Val Leu
                140                 145                 150

ACG GTC ATC TGG ACG TTC TGC ACG GGG ACT GGC ATC ACC ATG GTG ATC    1194
Thr Val Ile Trp Thr Phe Cys Thr Gly Thr Gly Ile Thr Met Val Ile
                155                 160                 165

TTC TCC CAT CAT GTG CCC ACA GTG ATC ACC TTC ACG TCG CTG TTC CCG    1242
Phe Ser His His Val Pro Thr Val Ile Thr Phe Thr Ser Leu Phe Pro
            170                 175                 180

CTG ATG CTG GTC TTC ATC CTG TGC CTC TAT GTG CAC ATG TTC CTG CTG    1290
Leu Met Leu Val Phe Ile Leu Cys Leu Tyr Val His Met Phe Leu Leu
        185                 190                 195

GCT CGA TCC CAC ACC AGG AAG ATC TCC ACC CTC CCC AGA GCC AAC ATG    1338
Ala Arg Ser His Thr Arg Lys Ile Ser Thr Leu Pro Arg Ala Asn Met
200                 205                 210                 215

AAA GGG GCC ATC ACA CTG ACC ATC CTG CTC GGG GTC TTC ATC TTC TGC    1386
Lys Gly Ala Ile Thr Leu Thr Ile Leu Leu Gly Val Phe Ile Phe Cys
                220                 225                 230

TGG GCC CCC TTT GTG CTT CAT GTC CTC TTG ATG ACA TTC TGC CCA AGT    1434
Trp Ala Pro Phe Val Leu His Val Leu Leu Met Thr Phe Cys Pro Ser
                235                 240                 245

AAC CCC TAC TGC GCC TGC TAC ATG TCT CTC TTC CAG GTG AAC GGC ATG    1482
Asn Pro Tyr Cys Ala Cys Tyr Met Ser Leu Phe Gln Val Asn Gly Met
            250                 255                 260

TTG ATC ATG TGC AAT GCC GTC ATT GAC CCC TTC ATA TAT GCC TTC CGG    1530
Leu Ile Met Cys Asn Ala Val Ile Asp Pro Phe Ile Tyr Ala Phe Arg
        265                 270                 275

AGC CCA GAG CTC AGG GAC GCA TTC AAA AAG ATG ATC TTC TGC AGC AGG    1578
Ser Pro Glu Leu Arg Asp Ala Phe Lys Lys Met Ile Phe Cys Ser Arg
280                 285                 290                 295

TAC TGG TAGAATGGCT GATCCCTGGT TTTAGAATCC ATGGGAATAA CGTTGCCAAG     1634
Tyr Trp

TGCCAGAATA GTGTAACATT CCAACAAATG CCAGTGCTCC TCACTGGCCT TCCTTCCCTA  1694
ATGGATGCAA GGATGACCCA CCAGCTAGTG TTTCTGAATA CTATGGCCAG GAACAGTCTA  1754
TTGTAGGGGC AACTCTATTT GTGACTGGAC AGATAAAACG TGTAGTAAAA GAAGGATAGA  1814
ATACAAAGTA TTAGGTACAA AAGTAATTAG GTTTGCATTA CTTATGACAA ATGCATTACT  1874
TTTGCACCAA TCTAGTAAAA CAGCAATAAA AATTCAAGGG CTTTGGGCTA AGGCAAAGAC  1934
TTGCTTTCCT GTGGACATTA ACAAGCCAGT TCTGAGGCGG CCTTTCCAGG TGGAGGCCAT  1994
TGCAGCCAAT TTCAGAGT                                                2012
```

FIG. 4A

```
GGGGCCAGAA AGTTCCTGCT TCAGAGCAGA AGATCTTCAG CAAGAACTAC AAAGAAGAAA         60

AGATTCTGGA GAATCAATCA AGTTTCCTGT CAAGTTCCAG TAACGTTTCT GTCTTAACTG        120

CACACAGGAA AG ATG AAA CAC ATT CTC AAT CTG TAT GAA AAC ATC AAC           168
              Met Lys His Ile Leu Asn Leu Tyr Glu Asn Ile Asn
                1           5                       10

AGT ACA GCA AGA AAT AAC TCA GAC TGT CCT GCT GTG ATT TTG CCA GAA         216
Ser Thr Ala Arg Asn Asn Ser Asp Cys Pro Ala Val Ile Leu Pro Glu
            15                  20                  25

GAG ATA TTT TTC ACA GTA TCC ATT GTT GGG GTT TTG GAG AAC CTG ATG         264
Glu Ile Phe Phe Thr Val Ser Ile Val Gly Val Leu Glu Asn Leu Met
        30                  35                  40

GTC CTT CTG GCT GTG GCC AAG AAT AAG AGT CTT CAG TCG CCC ATG TAC         312
Val Leu Leu Ala Val Ala Lys Asn Lys Ser Leu Gln Ser Pro Met Tyr
45                  50                  55                  60

TTT TTC ATC TGC AGC TTG GCT ATT TCC GAT ATG CTG GGG AGC CTG TAC         360
Phe Phe Ile Cys Ser Leu Ala Ile Ser Asp Met Leu Gly Ser Leu Tyr
                65                  70                  75

AAG ATT TTG GAA AAC GTT CTG ATC ATG TTC AAA AAC ATG GGT TAC CTC         408
Lys Ile Leu Glu Asn Val Leu Ile Met Phe Lys Asn Met Gly Tyr Leu
            80                  85                  90

GAG CCT CGA GGC AGT TTT GAA AGC ACA GCA GAT GAT GTG GTG GAC TCC         456
Glu Pro Arg Gly Ser Phe Glu Ser Thr Ala Asp Asp Val Val Asp Ser
        95                  100                 105

CTG TTC ATC CTC TCC CTT CTC GGC TCC ATC TGC AGC CTG TCT GTG ATT         504
Leu Phe Ile Leu Ser Leu Leu Gly Ser Ile Cys Ser Leu Ser Val Ile
110                 115                 120

GCC GCT GAC CGC TAC ATC ACA ATC TTC CAC GCT CTG CAG TAC CAC CGC         552
Ala Ala Asp Arg Tyr Ile Thr Ile Phe His Ala Leu Gln Tyr His Arg
125                 130                 135                 140

ATC ATG ACC CCC GCA CCG TGC CCT CGT CAT CTG ACG GTC CTC TGG GCA         600
Ile Met Thr Pro Ala Pro Cys Pro Arg His Leu Thr Val Leu Trp Ala
                145                 150                 155

GGC TGC ACA GGC AGT GGC ATT ACC ATC GTG ACC TTC TCC CAT CAC GTC         648
Gly Cys Thr Gly Ser Gly Ile Thr Ile Val Thr Phe Ser His His Val
            160                 165                 170

CCC ACA GTG ATC GCC TTC ACA GCG CTG TTC CCG CTG ATG CTG GCC TTC         696
Pro Thr Val Ile Ala Phe Thr Ala Leu Phe Pro Leu Met Leu Ala Phe
        175                 180                 185

ATC CTG TGC CTC TAC GTG CAC ATG TTC CTG CTG GCC CGC TCC CAC ACC         744
Ile Leu Cys Leu Tyr Val His Met Phe Leu Leu Ala Arg Ser His Thr
190                 195                 200

AGG AGG ACC CCC TCC CTT CCC AAA GCC AAC ATG AGA GGG GCC GTC ACA         792
Arg Arg Thr Pro Ser Leu Pro Lys Ala Asn Met Arg Gly Ala Val Thr
205                 210                 215                 220
```

FIG. 4B

```
CTG ACT GTC CTG CTC GGG GTC TTC ATT TTC TGT TGG GCA CCC TTT GTC        840
Leu Thr Val Leu Leu Gly Val Phe Ile Phe Cys Trp Ala Pro Phe Val
            225                 230                 235

CTT CAT GTC CTC TTG ATG ACA TTC TGC CCA GCT GAC CCC TAC TGT GCC        888
Leu His Val Leu Leu Met Thr Phe Cys Pro Ala Asp Pro Tyr Cys Ala
            240                 245                 250

TGC TAC ATG TCC CTC TTC CAG GTG AAT GGT GTG TTG ATC ATG TGT AAT        936
Cys Tyr Met Ser Leu Phe Gln Val Asn Gly Val Leu Ile Met Cys Asn
            255                 260                 265

GCC ATC ATC GAC CCC TTC ATA TAT GCC TTT CGG AGC CCA GAG CTC AGG        984
Ala Ile Ile Asp Pro Phe Ile Tyr Ala Phe Arg Ser Pro Glu Leu Arg
            270                 275                 280

GTC GCA TTC AAA AAG ATG GTT ATC TGC AAC TGT TAC CAG TAGAATGATT        1033
Val Ala Phe Lys Lys Met Val Ile Cys Asn Cys Tyr Gln
285                 290                 295

GGTCCCTGAT TTTAGGAGCC ACAGGGATAT ACTGTCAGGG ACAGAGTAGC GTGACAGACC      1093

AACAACACTA GGACT                                                        1108
```

FIG. 5A

| | | | | | |
|---|---|---|---|---|---|
| GGCTGTAACT | GTAGCAACCG | GTGTTGGGTG | GGGATGAGAA | GAGACCAGAG | AGAGAGAGGG | 60
| TCAGAGCGAC | AGGGGATGAG | ACAGGCTGGT | CAGAGTCTGC | ACTGATTGTT | GGAGACGCAA | 120
| AGGAAAGTTT | TTTCTATGTC | TCCAACCTCC | CCCTCCTCCC | CCGTTTCTCT | CTGGAGAAAC | 180
| TAAAATCTAG | ACTGGACAGC | ATCCACAAGA | GAAGCACCTA | GAAGAAGATT | TTTTTTTCCC | 240
| AGCAGCTTGC | TCAGGACCCT | GCAGGAGCTG | CAGCCGGAAC | TGGTCCCGCC | GATAACC | 297

```
ATG AAC TCT TCC TGC TGC CCG TCC TCC TCT TAT CCG ACG CTG CCT AAC       345
Met Asn Ser Ser Cys Cys Pro Ser Ser Ser Tyr Pro Thr Leu Pro Asn
 1               5                   10                  15

CTC TCC CAG CAC CCT GCA GCC CCC TCT GCC AGC AAC CGG AGT GGC AGT       393
Leu Ser Gln His Pro Ala Ala Pro Ser Ala Ser Asn Arg Ser Gly Ser
             20                  25                  30

GGG TTC TGC GAG CAG GTT TTC ATC AAG CCA GAG GTC TTC CTG GCA CTG       441
Gly Phe Cys Glu Gln Val Phe Ile Lys Pro Glu Val Phe Leu Ala Leu
         35                  40                  45

GGC ATC GTC AGT CTG ATG GAA AAC ATC CTG GTG ATC CTG GCT GTG GTG       489
Gly Ile Val Ser Leu Met Glu Asn Ile Leu Val Ile Leu Ala Val Val
     50                  55                  60

AGG AAC GGC AAC CTG CAC TCC CCC ATG TAC TTC TTC CTG CTG AGC CTG       537
Arg Asn Gly Asn Leu His Ser Pro Met Tyr Phe Phe Leu Leu Ser Leu
 65                  70                  75                  80

CTG CAG GCC GAC ATG CTG GTG AGC CTG TCC AAC TCC CTG GAG ACC ATC       585
Leu Gln Ala Asp Met Leu Val Ser Leu Ser Asn Ser Leu Glu Thr Ile
             85                  90                  95

ATG ATC GTG GTT ATC AAC AGC GAC TCC CTG ACC TTG GAG GAC CAA TTC       633
Met Ile Val Val Ile Asn Ser Asp Ser Leu Thr Leu Glu Asp Gln Phe
         100                 105                 110

ATC CAG CAC ATG GAC AAC ATC TTC GAC TCT ATG ATC TGC ATC TCC CTG       681
Ile Gln His Met Asp Asn Ile Phe Asp Ser Met Ile Cys Ile Ser Leu
     115                 120                 125

GTG GCC TCC ATC TGC AAC CTC CTG GCC ATC GCC GTG GAC AGG TAC GTC       729
Val Ala Ser Ile Cys Asn Leu Leu Ala Ile Ala Val Asp Arg Tyr Val
 130                 135                 140

ACC ATC TTC TAT GCC CTC CGT TAC CAC AGC ATC ATG ACG GTT AGG AAA       777
Thr Ile Phe Tyr Ala Leu Arg Tyr His Ser Ile Met Thr Val Arg Lys
145                 150                 155                 160

GCC CTC TCC TTG ATC GTG GCC ATC TGG GTC TGC TGT GGC ATC TGC GGC       825
Ala Leu Ser Leu Ile Val Ala Ile Trp Val Cys Cys Gly Ile Cys Gly
             165                 170                 175

GTG ATG TTC ATC GTC TAC TCC GAG AGC AAG ATG GTC ATC GTG TGC CTC       873
Val Met Phe Ile Val Tyr Ser Glu Ser Lys Met Val Ile Val Cys Leu
         180                 185                 190
```

FIG. 5B

```
ATC ACC ATG TTC TTC GCC ATG GTG CTC CTC ATG GGC ACC CTG TAC ATC        921
Ile Thr Met Phe Phe Ala Met Val Leu Leu Met Gly Thr Leu Tyr Ile
        195                 200                 205

CAC ATG TTC CTC TTC GCC AGG CTG CAC GTC CAG CGC ATC GCG GCA CTG        969
His Met Phe Leu Phe Ala Arg Leu His Val Gln Arg Ile Ala Ala Leu
    210                 215                 220

CCA CCT GCT GAC GGG GTA GCC CCG CAG CAG CAC TCG TGC ATG AAG GGG       1017
Pro Pro Ala Asp Gly Val Ala Pro Gln Gln His Ser Cys Met Lys Gly
225                 230                 235                 240

GCC GTC ACC ATC ACC ATC CTG CTG GGG GTT TTC ATC TTC TGC TGG GCG       1065
Ala Val Thr Ile Thr Ile Leu Leu Gly Val Phe Ile Phe Cys Trp Ala
                245                 250                 255

CCT TTC TTC CTC CAC CTG GTC CTC ATC ATC ACC TGC CCC ACC AAC CCC       1113
Pro Phe Phe Leu His Leu Val Leu Ile Ile Thr Cys Pro Thr Asn Pro
            260                 265                 270

TAC TGC ATC TGC TAC ACG GCG CAC TTC AAC ACC TAC CTG GTT CTC ATC       1161
Tyr Cys Ile Cys Tyr Thr Ala His Phe Asn Thr Tyr Leu Val Leu Ile
        275                 280                 285

ATG TGC AAC TCT GTC ATC GAC CCC CTC ATC TAC GCC TTC CGC AGC CTG       1209
Met Cys Asn Ser Val Ile Asp Pro Leu Ile Tyr Ala Phe Arg Ser Leu
    290                 295                 300

GAG CTG CGA AAC ACC TTC AAG GAG ATT CTC TGC GGT TGC AAT GGC ATG       1257
Glu Leu Arg Asn Thr Phe Lys Glu Ile Leu Cys Gly Cys Asn Gly Met
305                 310                 315                 320

AAC GTG GGC TAGGAACCCC CGAGGAGGTG TTCCACGGCT AGCCAAGAGA               1306
Asn Val Gly

GAAAAGCAAT GCTCAGGTGA GACACAGAAG GG                                   1338
```

FIG. 6A

```
AGCTTCCGAG AGGCAGCCGA TGTGAGCATG TGCGCACAGA TTCGTCTCCC AATGGCATGG      60

CAGCTTCAAG GAAAATTATT TTGAACAGAC TTGAATGCAT AAGATTAAAG TTAAAGCAGA     120

AGTGAGAACA AGAAAGCAAA GAGCAGACTC TTTCAACTGA GAATGAATAT TTTGAAGCCC     180

AAGATTTTAA AGTGATGATG ATTAGAGTCG TACCTAAAAG AGACTAAAAA CTCCATGTCA     240

AGCTCTGGAC TTGTGACATT TACTCACAGC AGGCATGGCA ATTTTAGCCT CACAACTTTC     300

AGACAGATAA AGACTTGGAG GAAATAACTG AGACGACTCC CTGACCCAGG AGGTTAAATC     360

AATTCAGGGG GACACTGGAA TTCTCCTGCC AGC ATG GTG AAC TCC ACC CAC CGT     414
                                   Met Val Asn Ser Thr His Arg
                                    1               5
```

| | | | | | | | | | | | | | | | | |
|---|---|---|---|---|---|---|---|---|---|---|---|---|---|---|---|---|
| GGG | ATG | CAC | ACT | TCT | CTG | CAC | CTC | TGG | AAC | CGC | AGC | AGT | TAC | AGA | CTG | 462 |
| Gly | Met | His | Thr | Ser | Leu | His | Leu | Trp | Asn | Arg | Ser | Ser | Tyr | Arg | Leu | |
| | | 10 | | | | | 15 | | | | | 20 | | | | |
| CAC | AGC | AAT | GCC | AGT | GAG | TCC | CTT | GGA | AAA | GGC | TAC | TCT | GAT | GGA | GGG | 510 |
| His | Ser | Asn | Ala | Ser | Glu | Ser | Leu | Gly | Lys | Gly | Tyr | Ser | Asp | Gly | Gly | |
| | | 25 | | | | 30 | | | | | 35 | | | | | |
| TGC | TAC | GAG | CAA | CTT | TTT | GTC | TCT | CCT | GAG | GTG | TTT | GTG | ACT | CTG | GGT | 558 |
| Cys | Tyr | Glu | Gln | Leu | Phe | Val | Ser | Pro | Glu | Val | Phe | Val | Thr | Leu | Gly | |
| 40 | | | | 45 | | | | | 50 | | | | | | 55 | |
| GTG | ATC | AGC | TTG | TTG | GAG | AAT | ATC | TTA | GTG | ATT | GTG | GCA | ATA | GCC | AAG | 606 |
| Val | Ile | Ser | Leu | Leu | Glu | Asn | Ile | Leu | Val | Ile | Val | Ala | Ile | Ala | Lys | |
| | | | | 60 | | | | | 65 | | | | | | 70 | |
| AAC | AAG | AAT | CTG | CAT | TCA | CCC | ATG | TAC | TTT | TTC | ATC | TGC | AGC | TTG | GCT | 654 |
| Asn | Lys | Asn | Leu | His | Ser | Pro | Met | Tyr | Phe | Phe | Ile | Cys | Ser | Leu | Ala | |
| | | | 75 | | | | 80 | | | | | 85 | | | | |
| GTG | GCT | GAT | ATG | CTG | GTG | AGC | GTT | TCA | AAT | GGA | TCA | GAA | ACC | ATT | ATC | 702 |
| Val | Ala | Asp | Met | Leu | Val | Ser | Val | Ser | Asn | Gly | Ser | Glu | Thr | Ile | Ile | |
| | | 90 | | | | 95 | | | | | 100 | | | | | |
| ATC | ACC | CTA | TTA | AAC | AGT | ACA | GAT | ACG | GAT | GCA | CAG | AGT | TTC | ACA | GTG | 750 |
| Ile | Thr | Leu | Leu | Asn | Ser | Thr | Asp | Thr | Asp | Ala | Gln | Ser | Phe | Thr | Val | |
| | 105 | | | | | 110 | | | | | 115 | | | | | |
| AAT | ATT | GAT | AAT | GTC | ATT | GAC | TCG | GTG | ATC | TGT | AGC | TCC | TTG | CTT | GCA | 798 |
| Asn | Ile | Asp | Asn | Val | Ile | Asp | Ser | Val | Ile | Cys | Ser | Ser | Leu | Leu | Ala | |
| 120 | | | | 125 | | | | | 130 | | | | | | 135 | |
| TCC | ATT | TGC | AGC | CTG | CTT | TCA | ATT | GCA | GTG | GAC | AGG | TAC | TTT | ACT | ATC | 846 |
| Ser | Ile | Cys | Ser | Leu | Leu | Ser | Ile | Ala | Val | Asp | Arg | Tyr | Phe | Thr | Ile | |
| | | | | 140 | | | | | 145 | | | | | | 150 | |
| TTC | TAT | GCT | CTC | CAG | TAC | CAT | AAC | ATT | ATG | ACA | GTT | AAG | CGG | GTT | GGG | 894 |
| Phe | Tyr | Ala | Leu | Gln | Tyr | His | Asn | Ile | Met | Thr | Val | Lys | Arg | Val | Gly | |
| | | | | 155 | | | | | 160 | | | | | 165 | | |
| ATC | AGC | ATA | AGT | TGT | ATC | TGG | GCA | GCT | TGC | ACG | GTT | TCA | GGC | ATT | TTG | 942 |
| Ile | Ser | Ile | Ser | Cys | Ile | Trp | Ala | Ala | Cys | Thr | Val | Ser | Gly | Ile | Leu | |
| | | 170 | | | | | 175 | | | | | 180 | | | | |

FIG. 6B

```
TTC ATC ATT TAC TCA GAT AGT AGT GCT GTC ATC ATC TGC CTC ATC ACC         990
Phe Ile Ile Tyr Ser Asp Ser Ser Ala Val Ile Ile Cys Leu Ile Thr
    185             190             195

ATG TTC TTC ACC ATG CTG GCT CTC ATG GCT TCT CTC TAT GTC CAC CTG        1038
Met Phe Phe Thr Met Leu Ala Leu Met Ala Ser Leu Tyr Val His Leu
200             205             210             215

TTC CTG ATG GCC AGG CTT CAC ATT AAG AGG ATT GCT GTC CTC CCC GGC        1086
Phe Leu Met Ala Arg Leu His Ile Lys Arg Ile Ala Val Leu Pro Gly
            220             225             230

ACT GGT GCC ATC CGC CAA GGT GCC AAT ATG AAG GGA GCG ATT ACC TTG        1134
Thr Gly Ala Ile Arg Gln Gly Ala Asn Met Lys Gly Ala Ile Thr Leu
                235             240             245

ACC ATC CTG ATT GGC GTC TTT GTT GTC TGC TGG GCC CCA TTC TTC CTC        1182
Thr Ile Leu Ile Gly Val Phe Val Val Cys Trp Ala Pro Phe Phe Leu
        250             255             260

CAC TTA ATA TTC TAC ATC TCT TGT CCT CAG AAT CCA TAT TGT GTG TGC        1230
His Leu Ile Phe Tyr Ile Ser Cys Pro Gln Asn Pro Tyr Cys Val Cys
265             270             275

TTC ATG TCT CAC TTT AAC TTG TAT CTC ATA CTG ATC ATG TGT AAT TCA        1278
Phe Met Ser His Phe Asn Leu Tyr Leu Ile Leu Ile Met Cys Asn Ser
280             285             290             295

ATC ATC GAT CCT CTG ATT TAT GCA CTC CGG AGT CAA GAA CTG AGG AAA        1326
Ile Ile Asp Pro Leu Ile Tyr Ala Leu Arg Ser Gln Glu Leu Arg Lys
            300             305             310

ACC TTC AAA GAG ATC ATC TCT TCC TAT CCC CTG GGA GGC TTT TGT GAC        1374
Thr Phe Lys Glu Ile Ile Ser Ser Tyr Pro Leu Gly Gly Leu Cys Asp
                315             320             325

TTG TCT AGC AGA TAT TAAATGGGGA CAGAGCACGC AATATAGGAA CATCCATAAG       1429
Leu Ser Ser Arg Tyr
            330

AGACTTTTTC ACTCTTACCC TACCTGAATA TTCTACTTCT GCAACAGCTT TCTCTTCCGT     1489

GTAGGGTACT GGTTGAGATA TCCATTGTGT AAATTTAAGC CTATGATTTT TAATGAGAAA     1549

AAATGCCCAG TCTCTGTATT ATTTCCAATC TCATGCTACT TTTTTGGCCA TAAAATATGA     1609

ATCTATGTTA TAGGTTGTAG GCACTGTGGA TTTACAAAAA GAAAAGTCCT TATTAAAAGC     1669

| | |
|---|---|
| ATG AAC TCC TCC TCC ACC CTG ACT GTA TTG AAT CTT ACC CTG AAC GCC<br>Met Asn Ser Ser Ser Thr Leu Thr Val Leu Asn Leu Thr Leu Asn Ala<br>1                         5                        10                     15 | 48 |
| TCA GAG GAT GGC ATT TTA GGA TCA AAT GTC AAG AAC AAG TCT TTG GCC<br>Ser Glu Asp Gly Ile Leu Gly Ser Asn Val Lys Asn Lys Ser Leu Ala<br>                   20                       25                     30 | 96 |
| TGT GAA GAA ATG GGC ATT GCC GTG GAG GTG TTC CTG ACC CTG GGT CTC<br>Cys Glu Glu Met Gly Ile Ala Val Glu Val Phe Leu Thr Leu Gly Leu<br>         35                       40                       45 | 144 |
| GTC AGC CTC TTA GAG AAC ATC CTG GTC ATT GGG GCC ATA GTA AAG AAC<br>Val Ser Leu Leu Glu Asn Ile Leu Val Ile Gly Ala Ile Val Lys Asn<br>      50                       55                     60 | 192 |
| AAA AAC CTG CAC TCA CCC ATG TAC TTC TTT GTG GGC AGC TTA GCC GTG<br>Lys Asn Leu His Ser Pro Met Tyr Phe Phe Val Gly Ser Leu Ala Val<br>65                       70                       75                     80 | 240 |
| GCC GAC ATG CTG GTG AGC ATG TCC AAT GCC TGG GAG ACT GTC ACC ATA<br>Ala Asp Met Leu Val Ser Met Ser Asn Ala Trp Glu Thr Val Thr Ile<br>                   85                       90                     95 | 288 |
| TAC TTG CTA AAT AAT AAA CAC CTG GTG ATA GCC GAC ACC TTT GTG CGA<br>Tyr Leu Leu Asn Asn Lys His Leu Val Ile Ala Asp Thr Phe Val Arg<br>              100                    105                  110 | 336 |
| CAC ATC GAC AAC GTG TTC GAC TCC ATG ATC TGC ATC TCT GTG GTG GCC<br>His Ile Asp Asn Val Phe Asp Ser Met Ile Cys Ile Ser Val Val Ala<br>            115                    120                  125 | 384 |
| TCG ATG TGC AGT TTG CTG GCC ATT GCG GTG GAT AGG TAC ATC ACC ATC<br>Ser Met Cys Ser Leu Leu Ala Ile Ala Val Asp Arg Tyr Ile Thr Ile<br>     130                    135                    140 | 432 |
| TTC TAT GCC TTG CGC TAC CAC CAC ATC ATG ACC GCG AGG CGC TCG GGG<br>Phe Tyr Ala Leu Arg Tyr His His Ile Met Thr Ala Arg Arg Ser Gly<br>145                    150                    155                  160 | 480 |
| GTG ATC ATC GCC TGC ATT TGG ACC TTC TGC ATA AGC TGC GGC ATT GTT<br>Val Ile Ile Ala Cys Ile Trp Thr Phe Cys Ile Ser Cys Gly Ile Val<br>              165                    170                  175 | 528 |
| TTC ATC ATC TAC TAT GAG TCC AAG TAT GTG ATC ATT TGC CTC ATC TCC<br>Phe Ile Ile Tyr Tyr Glu Ser Lys Tyr Val Ile Ile Cys Leu Ile Ser<br>              180                    185                  190 | 576 |
| ATG TTC TTC ACC ATG CTG TTC TTC ATG GTG TCT CTG TAT ATA CAC ATG<br>Met Phe Phe Thr Met Leu Phe Phe Met Val Ser Leu Tyr Ile His Met<br>     195                    200                    205 | 624 |
| TTC CTC CTG GCC CGG AAC CAT GTC AAG CGG ATA GCA GCT TCC CCC AGA<br>Phe Leu Leu Ala Arg Asn His Val Lys Arg Ile Ala Ala Ser Pro Arg<br>210                    215                    220 | 672 |
| TAC AAC TCC GTG AGG CAA AGG ACC AGC ATG AAG GGG GCT ATT ACC CTC<br>Tyr Asn Ser Val Arg Gln Arg Thr Ser Met Lys Gly Ala Ile Thr Leu<br>225                    230                    235                  240 | 720 |

FIG. 7B

```
ACC ATG CTA CTG GGG ATT TTC ATT GTC TGC TGG TCT CCC TTC TTT CTT       768
Thr Met Leu Leu Gly Ile Phe Ile Val Cys Trp Ser Pro Phe Phe Leu
            245                 250                 255

CAC CTT ATC TTA ATG ATC TCC TGC CCT CAG AAC GTC TAC TGC TCT TGC       816
His Leu Ile Leu Met Ile Ser Cys Pro Gln Asn Val Tyr Cys Ser Cys
            260                 265                 270

TTT ATG TCT TAC TTC AAC ATG TAC CTT ATA CTC ATC ATG TGC AAC TCC       864
Phe Met Ser Tyr Phe Asn Met Tyr Leu Ile Leu Ile Met Cys Asn Ser
        275                 280                 285

GTG ATC GAT CCT CTC ATC TAC GCC CTC CGC AGC CAA GAG ATG CGG AGG       912
Val Ile Asp Pro Leu Ile Tyr Ala Leu Arg Ser Gln Glu Met Arg Arg
    290                 295                 300

ACC TTT AAG GAG ATC GTC TGT TGT CAC GGA TTC CGG CGA CCT TGT AGG       960
Thr Phe Lys Glu Ile Val Cys Cys His Gly Phe Arg Arg Pro Cys Arg
305                 310                 315                 320

CTC CTT GGC GGG TAT TAA                                               978
Leu Leu Gly Gly Tyr  *
            325
```

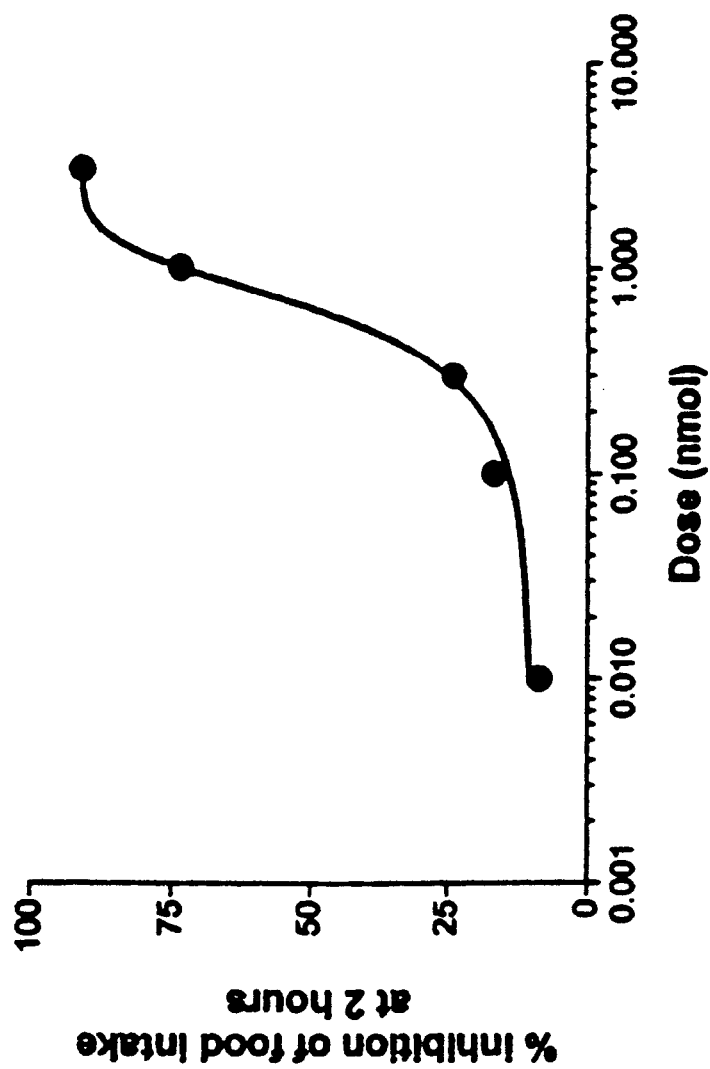

```
                         SEQUENCE LISTING (1) GENERAL INFORMATION:

(iii) NUMBER OF SEQUENCES: 19

(2) INFORMATION FOR SEQ ID NO:1:

(i) SEQUENCE CHARACTERISTICS:
         (A) LENGTH: 35 base pairs
         (B) TYPE: nucleic acid
         (C) STRANDEDNESS: single
         (D) TOPOLOGY: linear (ii) MOLECULE TYPE: DNA (genomic)

(ix) FEATURE:
         (A) NAME/KEY: misc_feature
         (B) LOCATION: 1..35
         (D) OTHER INFORMATION: /function = "Degenerate
             oligonucleotide primer (sense)"
             /note= "The residue at positions 24 and 24 are
             inosine"

(xi) SEQUENCE DESCRIPTION: SEQ ID NO:1:

GAGTCGACCT GTGYGYSATY RCNNTKGACM GSTAC                                35

(2) INFORMATION FOR SEQ ID NO:2:

(i) SEQUENCE CHARACTERISTICS:
         (A) LENGTH: 32 base pairs
         (B) TYPE: nucleic acid
         (C) STRANDEDNESS: single
         (D) TOPOLOGY: linear (ii) MOLECULE TYPE: DNA (genomic)

(ix) FEATURE:
         (A) NAME/KEY: misc_feature
         (B) LOCATION: 1..32
         (D) OTHER INFORMATION: /function = "Degenerate
             oligonucleotide primer (antisense)"
             /note= "The residue at position 18 is inosine"

(xi) SEQUENCE DESCRIPTION: SEQ ID NO:2:

CAGAATTCAG WAGGGCANCC AGCAGASRYG AA                                   32

(2) INFORMATION FOR SEQ ID NO:3:

(i) SEQUENCE CHARACTERISTICS:
         (A) LENGTH: 1260 base pairs
         (B) TYPE: nucleic acid
         (C) STRANDEDNESS: single
         (D) TOPOLOGY: linear (ii) MOLECULE TYPE: cDNA to mRNA (ix) FEATURE:
         (A) NAME/KEY: 5'UTR
         (B) LOCATION: 1..14

(ix) FEATURE:
         (A) NAME/KEY: CDS
         (B) LOCATION: 15..959
```

(ix) FEATURE:
    (A) NAME/KEY: 3'UTR
    (B) LOCATION: 960..1260

(xi) SEQUENCE DESCRIPTION: SEQ ID NO:3:

```
TTCCTGACAA GACT ATG TCC ACT CAG GAG CCC CAG AAG AGT CTT CTG GGT       50
               Met Ser Thr Gln Glu Pro Gln Lys Ser Leu Leu Gly
                1               5                  10

TCT CTC AAC TCC AAT GCC ACC TCT CAC CTT GGA CTG GCC ACC AAC CAG       98
Ser Leu Asn Ser Asn Ala Thr Ser His Leu Gly Leu Ala Thr Asn Gln
         15              20                  25

TCA GAG CCT TGG TGC CTG TAT GTG TCC ATC CCA GAT GGC CTC TTC CTC      146
Ser Glu Pro Trp Cys Leu Tyr Val Ser Ile Pro Asp Gly Leu Phe Leu
     30              35                  40

AGC CTA GGG CTG GTG AGT CTG GTG GAG AAT GTG CTG GTT GTG ATA GCC      194
Ser Leu Gly Leu Val Ser Leu Val Glu Asn Val Leu Val Val Ile Ala
 45              50                  55                      60

ATC ACC AAA AAC CGC AAC CTG CAC TCG CCC ATG TAT TAC TTC ATC TGC      242
Ile Thr Lys Asn Arg Asn Leu His Ser Pro Met Tyr Tyr Phe Ile Cys
                 65              70                  75

TGC CTG GCC CTG TCT GAC CTG ATG GTA AGT GTC AGC ATC GTG CTG GAG      290
Cys Leu Ala Leu Ser Asp Leu Met Val Ser Val Ser Ile Val Leu Glu
             80                  85                  90

ACT ACT ATC ATC CTG CTG CTG GAG GTG GGC ATC CTG GTG GCC AGA GTG      338
Thr Thr Ile Ile Leu Leu Leu Glu Val Gly Ile Leu Val Ala Arg Val
         95                 100                 105

GCT TTG GTG CAG CAG CTG GAC AAC CTC ATT GAC GTG CTC ATC TGT GGC      386
Ala Leu Val Gln Gln Leu Asp Asn Leu Ile Asp Val Leu Ile Cys Gly
     110                 115                 120

TCC ATG GTG TCC AGT CTC TGC TTC CTG GGC ATC ATT GCT ATA GAC CGC      434
Ser Met Val Ser Ser Leu Cys Phe Leu Gly Ile Ile Ala Ile Asp Arg
125             130                 135                     140

TAC ATC TCC ATC TTC TAT GCG CTG CGT TAT CAC AGC ATC GTG ACG CTG      482
Tyr Ile Ser Ile Phe Tyr Ala Leu Arg Tyr His Ser Ile Val Thr Leu
                 145                 150                 155

CCC AGA GCA CGA CGG GCT GTC GTG GGC ATC TGG ATG GTC AGC ATC GTC      530
Pro Arg Ala Arg Arg Ala Val Val Gly Ile Trp Met Val Ser Ile Val
             160                 165                 170

TCC AGC ACC CTC TTT ATC ACC TAC TAC AAG CAC ACA GCC GTT CTG CTC      578
Ser Ser Thr Leu Phe Ile Thr Tyr Tyr Lys His Thr Ala Val Leu Leu
         175                 180                 185

TGC CTC GTC ACT TTC TTT CTA GCC ATG CTG GCA CTC ATG GCG ATT CTG      626
Cys Leu Val Thr Phe Phe Leu Ala Met Leu Ala Leu Met Ala Ile Leu
     190                 195                 200

TAT GCC CAC ATG TTC ACG AGA GCG TGC CAG CAC GTC CAG GGC ATT GCC      674
Tyr Ala His Met Phe Thr Arg Ala Cys Gln His Val Gln Gly Ile Ala
205                 210                 215                 220

CAG CTC CAC AAA AGG CGG CGG TCC ATC CGC CAA GGC TTC TGC CTC AAG      722
Gln Leu His Lys Arg Arg Arg Ser Ile Arg Gln Gly Phe Cys Leu Lys
             225                 230                 235

GGT GCT GCC ACC CTT ACT ATC CTT CTG GGG ATT TTC TTC CTG TGC TGG      770
Gly Ala Ala Thr Leu Thr Ile Leu Leu Gly Ile Phe Phe Leu Cys Trp
         240                 245                 250

GGC CCC TTC TTC CTG CAT CTC TTG CTC ATC GTC CTC TGC CCT CAG CAC      818
Gly Pro Phe Phe Leu His Leu Leu Leu Ile Val Leu Cys Pro Gln His
     255                 260                 265

CCC ACC TGC AGC TGC ATC TTC AAG AAC TTC AAC CTC TTC CTC CTC      866
Pro Thr Cys Ser Cys Ile Phe Lys Asn Phe Asn Leu Phe Leu Leu Leu
270                 275                 280

ATC GTC CTC AGC TCC ACT GTT GAC CCC CTC ATC TAT GCT TTC CGC AGC      914
```

```
Ile Val Leu Ser Ser Thr Val Asp Pro Leu Ile Tyr Ala Phe Arg Ser
285                 290                 295                 300

CAG GAG CTC CGC ATG ACA CTC AAG GAG GTG CTG CTG TGC TCC TGG            959
Gln Glu Leu Arg Met Thr Leu Lys Glu Val Leu Leu Cys Ser Trp
            305                 310                 315

TGATCAGAGG GCGCTGGGCA GAGGGTGACA GTGATATCCA GTGGCCTGCA TCTGTGAGAC      1019

CACAGGTACT CATCCCTTCC TGATCTCCAT TTGTCTAAGG GTCGACAGGA TGAGCTTTAA      1079

AATAGAAACC CAGAGTGCCT GGGGCCAGGA GAAAGGGTAA CTGTGACTGC AGGGCTCACC      1139

CAGGGCAGCT ACGGGAAGTG GAGGAGACAG GGATGGGAAC TCTAGCCCTG AGCAAGGGTC      1199

AGACCACAGG CTCCTGAAGA GCTTCACCTC TCCCCACCTA CAGGCAACTC CTGCTCAAGC      1259

C                                                                      1260
```

(2) INFORMATION FOR SEQ ID NO:4:

(i) SEQUENCE CHARACTERISTICS:
        (A) LENGTH: 315 amino acids
        (B) TYPE: amino acid
        (D) TOPOLOGY: linear (ii) MOLECULE TYPE: protein (xi) SEQUENCE DESCRIPTION: SEQ ID NO:4:

```
Met Ser Thr Gln Glu Pro Gln Lys Ser Leu Leu Gly Ser Leu Asn Ser
 1               5                  10                  15

Asn Ala Thr Ser His Leu Gly Leu Ala Thr Asn Gln Ser Glu Pro Trp
                20                  25                  30

Cys Leu Tyr Val Ser Ile Pro Asp Gly Leu Phe Leu Ser Leu Gly Leu
            35                  40                  45

Val Ser Leu Val Glu Asn Val Leu Val Ile Ala Ile Thr Lys Asn
        50                  55                  60

Arg Asn Leu His Ser Pro Met Tyr Tyr Phe Ile Cys Cys Leu Ala Leu
65                  70                  75                  80

Ser Asp Leu Met Val Ser Val Ser Ile Val Leu Glu Thr Thr Ile Ile
                85                  90                  95

Leu Leu Leu Glu Val Gly Ile Leu Val Ala Arg Val Ala Leu Val Gln
                100                 105                 110

Gln Leu Asp Asn Leu Ile Asp Val Leu Ile Cys Gly Ser Met Val Ser
            115                 120                 125

Ser Leu Cys Phe Leu Gly Ile Ile Ala Ile Asp Arg Tyr Ile Ser Ile
130                 135                 140

Phe Tyr Ala Leu Arg Tyr His Ser Ile Val Thr Leu Pro Arg Ala Arg
145                 150                 155                 160

Arg Ala Val Val Gly Ile Trp Met Val Ser Ile Val Ser Ser Thr Leu
                165                 170                 175

Phe Ile Thr Tyr Tyr Lys His Thr Ala Val Leu Leu Cys Leu Val Thr
                180                 185                 190

Phe Phe Leu Ala Met Leu Ala Leu Met Ala Ile Leu Tyr Ala His Met
            195                 200                 205

Phe Thr Arg Ala Cys Gln His Val Gln Gly Ile Ala Gln Leu His Lys
        210                 215                 220

Arg Arg Arg Ser Ile Arg Gln Gly Phe Cys Leu Lys Gly Ala Ala Thr
225                 230                 235                 240

Leu Thr Ile Leu Leu Gly Ile Phe Phe Leu Cys Trp Gly Pro Phe Phe
                245                 250                 255
```

```
Leu His Leu Leu Leu Ile Val Leu Cys Pro Gln His Pro Thr Cys Ser
        260                 265                 270

Cys Ile Phe Lys Asn Phe Asn Leu Phe Leu Leu Ile Val Leu Ser
        275                 280                 285

Ser Thr Val Asp Pro Leu Ile Tyr Ala Phe Arg Ser Gln Glu Leu Arg
        290                 295                 300

Met Thr Leu Lys Glu Val Leu Cys Ser Trp
305                 310                 315

(2) INFORMATION FOR SEQ ID NO:5:

(i) SEQUENCE CHARACTERISTICS:
        (A) LENGTH: 1633 base pairs
        (B) TYPE: nucleic acid
        (C) STRANDEDNESS: single
        (D) TOPOLOGY: linear (ii) MOLECULE TYPE: cDNA to mRNA (ix) FEATURE:
        (A) NAME/KEY: 5'UTR
        (B) LOCATION: 1..461

(ix) FEATURE:
        (A) NAME/KEY: CDS
        (B) LOCATION: 462..1415

(ix) FEATURE:
        (A) NAME/KEY: 3'UTR
        (B) LOCATION: 1416..1633

(xi) SEQUENCE DESCRIPTION: SEQ ID NO:5:
```

| | |
|---|---|
| CCCGCATGTG GCCGCCCTCA ATGGAGGGCT CTGAGAACGA CTTTTAAAAC GCAGAGAAAA | 60 |
| AGCTCCATTC TTCCCAGACC TCAGCGCAGC CCTGGCCCAG GAAGGGAGGA GACAGAGGCC | 120 |
| AGGACGGTCC AGAGGTGTCG AAATGTCCTG GGAACCTGAG CAGCAGCCAC CAGGGAAGAG | 180 |
| GCAGGGAGGG AGCTGAGGAC CAGGCTTGGT TGTGAGAATC CCTGAGCCCA GGCGGTTGAT | 240 |
| GCCAGGAGGT GTCTGGACTG GCTGGGCCAT GCCTGGGCTG ACCTGTCCAG CCAGGGAGAG | 300 |
| GGTGTGAGGG CAGATCTGGG GGTGCCCAGA TGGAAGGAGG CAGGCATGGG GACACCCAAG | 360 |
| GCCCCCTGGC AGCACCATGA ACTAAGCAGG ACACCTGGAG GGGAAGAACT GTGGGGACCT | 420 |
| GGAGGCCTCC AACGACTCCT TCCTGCTTCC TGGACAGGAC T ATG GCT GTG CAG | 473 |
|                                                          Met Ala Val Gln<br>                                                             1 | |
| GGA TCC CAG AGA AGA CTT CTG GGC TCC CTC AAC TCC ACC CCC ACA GCC<br>Gly Ser Gln Arg Arg Leu Leu Gly Ser Leu Asn Ser Thr Pro Thr Ala<br> 5                     10                 15                 20 | 521 |
| ATC CCC CAG CTG GGG CTG GCT GCC AAC CAG ACA GGA GCC CGG TGC CTG<br>Ile Pro Gln Leu Gly Leu Ala Ala Asn Gln Thr Gly Ala Arg Cys Leu<br>               25                          30                         35 | 569 |
| GAG GTG TCC ATC TCT GAC GGG CTC TTC CTC AGC CTG GGG CTG GTG AGC<br>Glu Val Ser Ile Ser Asp Gly Leu Phe Leu Ser Leu Gly Leu Val Ser<br>               40                          45                         50 | 617 |
| TTG GTG GAG AAC GCG CTG GTG GTG GCC ACC ATC GCC AAG AAC CGG AAC<br>Leu Val Glu Asn Ala Leu Val Val Ala Thr Ile Ala Lys Asn Arg Asn<br>     55                         60                         65 | 665 |
| CTG CAC TCA CCC ATG TAC TGC TTC ATC TGC TGC CTG GCC TTG TCG GAC<br>Leu His Ser Pro Met Tyr Cys Phe Ile Cys Cys Leu Ala Leu Ser Asp<br>     70                         75                         80 | 713 |
| CTG CTG GTG AGC GGG ACG AAC GTG CTG GAG ACG GCC GTC ATC CTC CTG<br>Leu Leu Val Ser Gly Thr Asn Val Leu Glu Thr Ala Val Ile Leu Leu<br>85                      90                         95                      100 | 761 |

-continued

```
CTG GAG GCC GGT GCA CTG GTG GCC CGG GCT GCG GTG CTG CAG CAG CTG          809
Leu Glu Ala Gly Ala Leu Val Ala Arg Ala Ala Val Leu Gln Gln Leu
                105                 110                 115

GAC AAT GTC ATT GAC GTG ATC ACC TGC AGC TCC ATG CTG TCC AGC CTC          857
Asp Asn Val Ile Asp Val Ile Thr Cys Ser Ser Met Leu Ser Ser Leu
            120                 125                 130

TGC TTC CTG GGC GCC ATC GCC GTG GAC CGC TAC ATC TCC ATC TTC TAC          905
Cys Phe Leu Gly Ala Ile Ala Val Asp Arg Tyr Ile Ser Ile Phe Tyr
                135                 140                 145

GCA CTG CGC TAC CAC AGC ATC GTG ACC CTG CCG CGG GCG CCG CGA GCC          953
Ala Leu Arg Tyr His Ser Ile Val Thr Leu Pro Arg Ala Pro Arg Ala
        150                 155                 160

GTT GCG GCC ATC TGG GTG GCC AGT GTC GTC TTC AGC ACG CTC TTC ATC         1001
Val Ala Ala Ile Trp Val Ala Ser Val Val Phe Ser Thr Leu Phe Ile
165                 170                 175                 180

GGC TAC TAC GAC CAC GTG GCC GTC CTG CTG TGC CTC GTG GTC TTC TTC         1049
Gly Tyr Tyr Asp His Val Ala Val Leu Leu Cys Leu Val Val Phe Phe
                185                 190                 195

CTG GCT ATG CTG GTG CTC ATG GCC GTG CTG GAC GTC CAC ATG CTG GCC         1097
Leu Ala Met Leu Val Leu Met Ala Val Leu Asp Val His Met Leu Ala
                200                 205                 210

CGG GCC TGC CAG CAC GCC CAG GGC ATC GCC CGG CTC CAC AAG AGG CAG         1145
Arg Ala Cys Gln His Ala Gln Gly Ile Ala Arg Leu His Lys Arg Gln
                215                 220                 225

CGC CCG GTC CAC CAG GGC TTT GGC CTT AAA GGC GCT GTC ACC CTC ACC         1193
Arg Pro Val His Gln Gly Phe Gly Leu Lys Gly Ala Val Thr Leu Thr
        230                 235                 240

ATC CTG CTG GGC ATT TTC TTC CTC TGC TGG GGC CCC TTC TTC CTG CAT         1241
Ile Leu Leu Gly Ile Phe Phe Leu Cys Trp Gly Pro Phe Phe Leu His
245                 250                 255                 260

CTC ACA CTC ATC GTC CTC TGC CCC GAG CAC CCC ACG TGC GGC TGC ATC         1289
Leu Thr Leu Ile Val Leu Cys Pro Glu His Pro Thr Cys Gly Cys Ile
                265                 270                 275

TTC AAG AAC TTC AAC CTC TTT CTC GCC CTC ATC ATC TGC AAT GCC ATC         1337
Phe Lys Asn Phe Asn Leu Phe Leu Ala Leu Ile Ile Cys Asn Ala Ile
                280                 285                 290

ATC GAC CCC CTC ATC TAC GCC TTC CAC AGC CAG GAG CTC CGC AGG ACG         1385
Ile Asp Pro Leu Ile Tyr Ala Phe His Ser Gln Glu Leu Arg Arg Thr
                295                 300                 305

CTC AAG GAG GTG CTG ACA TGC TCC TGG TGA GCGCGGTGCA CGCGCTTTAA           1435
Leu Lys Glu Val Leu Thr Cys Ser Trp *
310                 315

GTGTGCTGGG CAGAGGGAGG TGGTGATATT GTGGTCTGGT TCCTGTGTGA CCCTGGGCAG       1495

TTCCTTACCT CCCTGGTCCC CGTTTGTCAA AGAGGATGGA CTAAATGATC TCTGAAAGTG       1555

TTGAAGCGCG GACCCTTCTG GGCAGGGAGG GGTCCTGCAA AACTCCAGGC AGGACTTCTC       1615

ACCAGCAGTC GTGGGAAC                                                    1633
```

(2) INFORMATION FOR SEQ ID NO:6:

(i) SEQUENCE CHARACTERISTICS:
        (A) LENGTH: 317 amino acids
        (B) TYPE: amino acid
        (D) TOPOLOGY: linear (ii) MOLECULE TYPE: protein (xi) SEQUENCE DESCRIPTION: SEQ ID NO:6:

```
Met Ala Val Gln Gly Ser Gln Arg Arg Leu Leu Gly Ser Leu Asn Ser
1               5                   10                  15
```

-continued

```
Thr Pro Thr Ala Ile Pro Gln Leu Gly Leu Ala Ala Asn Gln Thr Gly
         20                  25                  30

Ala Arg Cys Leu Glu Val Ser Ile Ser Asp Gly Leu Phe Leu Ser Leu
         35                  40                  45

Gly Leu Val Ser Leu Val Glu Asn Ala Leu Val Val Ala Thr Ile Ala
         50                  55                  60

Lys Asn Arg Asn Leu His Ser Pro Met Tyr Cys Phe Ile Cys Cys Leu
 65                  70                  75                  80

Ala Leu Ser Asp Leu Leu Val Ser Gly Thr Asn Val Leu Glu Thr Ala
                 85                  90                  95

Val Ile Leu Leu Leu Glu Ala Gly Ala Leu Val Ala Arg Ala Ala Val
                100                 105                 110

Leu Gln Gln Leu Asp Asn Val Ile Asp Val Ile Thr Cys Ser Ser Met
        115                 120                 125

Leu Ser Ser Leu Cys Phe Leu Gly Ala Ile Ala Val Asp Arg Tyr Ile
        130                 135                 140

Ser Ile Phe Tyr Ala Leu Arg Tyr His Ser Ile Val Thr Leu Pro Arg
145                 150                 155                 160

Ala Pro Arg Ala Val Ala Ala Ile Trp Val Ala Ser Val Val Phe Ser
                165                 170                 175

Thr Leu Phe Ile Gly Tyr Tyr Asp His Val Ala Val Leu Leu Cys Leu
                180                 185                 190

Val Val Phe Phe Leu Ala Met Leu Val Leu Met Ala Val Leu Asp Val
                195                 200                 205

His Met Leu Ala Arg Ala Cys Gln His Ala Gln Gly Ile Ala Arg Leu
        210                 215                 220

His Lys Arg Gln Arg Pro Val His Gln Gly Phe Gly Leu Lys Gly Ala
225                 230                 235                 240

Val Thr Leu Thr Ile Leu Leu Gly Ile Phe Phe Leu Cys Trp Gly Pro
                245                 250                 255

Phe Phe Leu His Leu Thr Leu Ile Val Leu Cys Pro Glu His Pro Thr
                260                 265                 270

Cys Gly Cys Ile Phe Lys Asn Phe Asn Leu Phe Leu Ala Leu Ile Ile
        275                 280                 285

Cys Asn Ala Ile Ile Asp Pro Leu Ile Tyr Ala Phe His Ser Gln Glu
        290                 295                 300

Leu Arg Arg Thr Leu Lys Glu Val Leu Thr Cys Ser Trp
305                 310                 315

(2) INFORMATION FOR SEQ ID NO:7:

(i) SEQUENCE CHARACTERISTICS:
        (A) LENGTH: 2012 base pairs
        (B) TYPE: nucleic acid
        (C) STRANDEDNESS: single
        (D) TOPOLOGY: linear (ii) MOLECULE TYPE: cDNA to mRNA (ix) FEATURE:
         (A) NAME/KEY: 5'UTR
         (B) LOCATION: 1..693

(ix) FEATURE:
         (A) NAME/KEY: CDS
         (B) LOCATION: 694..1587

(ix) FEATURE:
         (A) NAME/KEY: 3'UTR
         (B) LOCATION: 1588..2012
```

(xi) SEQUENCE DESCRIPTION: SEQ ID NO:7:

```
ACAACACTTT ATATATATTT TTATAAATGT AAGGGGTACA AAGGTGCCAT TTTGTTACAT      60

GGATATACCG TGTAGTGGTG AAGCCTGGGC TTTTAGTGTA TCTGTCATCA GAATAACATA     120

CGTGTTACCC ATAGGAATTT CTCATCACCC GCCCCCTCCA CCCTTCGAGT CTCCAATGTC     180

CATTCCACAC TCTATATCCA CGTGTATGCA TATAGCTCCA CATATAAGTG AGAACATGTA     240

GTATTTGACT TCCTCTTTCT GAGTTATTTC ACTTTGATAA TGGCCTCCAC TTCCATCCAT     300

GTTGCTGCAA AAGACATGAC CTTATTCTTT TTGATAGCTG GGGAGTACTC CATTGTGTAT     360

ATGTACCACA TTTCTTTATC CATTCACCCA TTGAGAACAC TTAGTTGATT CCATATCTTT     420

GCTATTGTCA CTAGTGCTGC AATAAACATA CATGTGCAGG CTCCTTCTAA TATACTGATT     480

TATATTTTAT GGAGAGAGAT AGAGTTCTTA GCGAGTGTGC TGTTTATTTC TAGTGTACTT     540

GCAACTAATA TTCTGTATAC TCCCTTTAGG TGATTGGAGA TTTAACTTAG ATCTCCAGCA     600

AGTGCTACAA GAAGAAAAGA TCCTGAAGAA TCAATCAAGT TTCCGTGAAG TCAAGTCCAA     660

GTAACATCCC CGCCTTAACC ACAAGCAGGA GAA ATG AAG CAC ATT ATC AAC TCG     714
                                  Met Lys His Ile Ile Asn Ser
                                    1               5

TAT GAA AAC ATC AAC AAC ACA GCA AGA AAT AAT TCC GAC TGT CCT CGT     762
Tyr Glu Asn Ile Asn Asn Thr Ala Arg Asn Asn Ser Asp Cys Pro Arg
         10                  15                  20

TGT GTT TTG CCG GAG GAG ATA TTT TTC ACA ATT TCC ATT GTT GGA GTT     810
Cys Val Leu Pro Glu Glu Ile Phe Phe Thr Ile Ser Ile Val Gly Val
     25                  30                  35

TTG GAG AAT CTG ATC GTC CTG CTG GCT GTG TTC AAG AAT AAG AAT CTC     858
Leu Glu Asn Leu Ile Val Leu Leu Ala Val Phe Lys Asn Lys Asn Leu
 40                  45                  50                  55

CAG GCA CCC ATG TAC TTT TTC ATC TGT AGC TTG GCC ATA TCT GAT ATG     906
Gln Ala Pro Met Tyr Phe Phe Ile Cys Ser Leu Ala Ile Ser Asp Met
                 60                  65                  70

CTG GGC AGC CTA TAT AAG ATC TTG GAA AAT ATC CTG ATC ATA TTG AGA     954
Leu Gly Ser Leu Tyr Lys Ile Leu Glu Asn Ile Leu Ile Ile Leu Arg
             75                  80                  85

AAC ATG GGC ATA CTC AAG CCA CGT GGC AGT TTT GAA ACC ACA GCC CAT    1002
Asn Met Gly Ile Leu Lys Pro Arg Gly Ser Phe Glu Thr Thr Ala His
         90                  95                 100

GAC ATC ATC GAC TCC CTG TTT CTG CTC TCC CGT CTT GGC TCC ATC TTC    1050
Asp Ile Ile Asp Ser Leu Phe Leu Leu Ser Arg Leu Gly Ser Ile Phe
     105                 110                 115

GAC CTG CTC GTG ATT GCT GCG GAC CGC TAC ATC ACC ATC TTC CAC GCA    1098
Asp Leu Leu Val Ile Ala Ala Asp Arg Tyr Ile Thr Ile Phe His Ala
120                 125                 130                 135

CTG CGG TAC CAC AGC ATC GTG ACC ATG CGC CGC ACT GTG GTG GTG CTT    1146
Leu Arg Tyr His Ser Ile Val Thr Met Arg Arg Thr Val Val Val Leu
                140                 145                 150

ACG GTC ATC TGG ACG TTC TGC ACG GGG ACT GGC ATC ACC ATG GTG ATC    1194
Thr Val Ile Trp Thr Phe Cys Thr Gly Thr Gly Ile Thr Met Val Ile
            155                 160                 165

TTC TCC CAT CAT GTG CCC CAC GTG ATC ACC TTC ACG TCG CTG TTC CCG    1242
Phe Ser His His Val Pro His Val Ile Thr Phe Thr Ser Leu Phe Pro
        170                 175                 180

CTG ATG CTG GTC TTC ATC CTG TGC CTC TAT GTG CAC ATG TTC CTG CTG    1290
Leu Met Leu Val Phe Ile Leu Cys Leu Tyr Val His Met Phe Leu Leu
    185                 190                 195

GCT CGA TGG CAC ACC AGG AAG ATC TCC ACC CTC CCC AGA GCC AAC ATG    1338
Ala Arg Trp His Thr Arg Lys Ile Ser Thr Leu Pro Arg Ala Asn Met
```

```
                200                 205                 210                 215
AAA GGG GCC ATG ACA CTG ACC ATC CTG CTC GGG GTC TTC ATC TTC TGC                1386
Lys Gly Ala Met Thr Leu Thr Ile Leu Leu Gly Val Phe Ile Phe Cys
                    220                 225                 230

TGG GCC CCC TTT GTG CTT CAT GTC CTC TTG ATG ACA TTC TGC CCA AGT                1434
Trp Ala Pro Phe Val Leu His Val Leu Leu Met Thr Phe Cys Pro Ser
            235                 240                 245

AAC CCC TAC TGC GCC TGC TAC ATG TCT CTC TTC CAG GTG AAC GGC ATG                1482
Asn Pro Tyr Cys Ala Cys Tyr Met Ser Leu Phe Gln Val Asn Gly Met
        250                 255                 260

TTG ATC ATG TGC AAT GCC GTC ATT GAC CCC TTC ATA TAT GCC TTC CGG                1530
Leu Ile Met Cys Asn Ala Val Ile Asp Pro Phe Ile Tyr Ala Phe Arg
    265                 270                 275

AGC CCA GAG CTC AGG GAC GCA TTC AAA AAG ATG ATC TTC TGC AGC AGG                1578
Ser Pro Glu Leu Arg Asp Ala Phe Lys Lys Met Ile Phe Cys Ser Arg
280                 285                 290                 295

TAC TGG TAG AATGGCTGAT CCCTGGTTTT AGAATCCATG GGAATAACGT                        1627
Tyr Trp *

TGCCAAGTGC CAGAATAGTG TAACATTCCA ACAAATGCCA GTGCTCCTCA CTGGCCTTCC              1687

TTCCCTAATG GATGCAAGGA TGACCCACCA GCTAGTGTTT CTGAATACTA TGGCCAGGAA              1747

CAGTCTATTG TAGGGGCAAC TCTATTTGTG ACTGGACAGA TAAAACGTGT AGTAAAAGAA              1807

GGATAGAATA CAAAGTATTA GGTACAAAAG TAATTAGGTT TGCATTACTT ATGACAAATG              1867

CATTACTTTT GCACCAATCT AGTAAAACAG CAATAAAAAT TCAAGGGCTT TGGGCTAAGG              1927

CAAAGACTTG CTTTCCTGTG GACATTAACA AGCCAGTTCT GAGGCGGCCT TTCCAGGTGG              1987

AGGCCATTGC AGCCAATTTC AGAGT                                                    2012

(2) INFORMATION FOR SEQ ID NO:8:

(i) SEQUENCE CHARACTERISTICS:
        (A) LENGTH: 297 amino acids
        (B) TYPE: amino acid
        (D) TOPOLOGY: linear (ii) MOLECULE TYPE: protein (xi) SEQUENCE DESCRIPTION: SEQ ID NO:8:

Met Lys His Ile Ile Asn Ser Tyr Glu Asn Ile Asn Asn Thr Ala Arg
 1               5                  10                  15

Asn Asn Ser Asp Cys Pro Arg Cys Val Leu Pro Glu Glu Ile Phe Phe
                20                  25                  30

Thr Ile Ser Ile Val Gly Val Leu Glu Asn Leu Ile Val Leu Leu Ala
            35                  40                  45

Val Phe Lys Asn Lys Asn Leu Gln Ala Pro Met Tyr Phe Phe Ile Cys
        50                  55                  60

Ser Leu Ala Ile Ser Asp Met Leu Gly Ser Leu Tyr Lys Ile Leu Glu
65                  70                  75                  80

Asn Ile Leu Ile Ile Leu Arg Asn Met Gly Ile Leu Lys Pro Arg Gly
                85                  90                  95

Ser Phe Glu Thr Thr Ala His Asp Ile Ile Asp Ser Leu Phe Leu Leu
                100                 105                 110

Ser Arg Leu Gly Ser Ile Phe Asp Leu Leu Val Ile Ala Ala Asp Arg
            115                 120                 125

Tyr Ile Thr Ile Phe His Ala Leu Arg Tyr His Ser Ile Val Thr Met
        130                 135                 140

Arg Arg Thr Val Val Val Leu Thr Val Ile Trp Thr Phe Cys Thr Gly
```

```
                    145                 150                 155                 160

Thr Gly Ile Thr Met Val Ile Phe Ser His His Val Pro His Val Ile
                    165                 170                 175

Thr Phe Thr Ser Leu Phe Pro Leu Met Leu Val Phe Ile Leu Cys Leu
                    180                 185                 190

Tyr Val His Met Phe Leu Leu Ala Arg Trp His Thr Arg Lys Ile Ser
                    195                 200                 205

Thr Leu Pro Arg Ala Asn Met Lys Gly Ala Met Thr Leu Thr Ile Leu
                    210                 215                 220

Leu Gly Val Phe Ile Phe Cys Trp Ala Pro Phe Val Leu His Val Leu
    225                 230                 235                 240

Leu Met Thr Phe Cys Pro Ser Asn Pro Tyr Cys Ala Cys Tyr Met Ser
                    245                 250                 255

Leu Phe Gln Val Asn Gly Met Leu Ile Met Cys Asn Ala Val Ile Asp
                    260                 265                 270

Pro Phe Ile Tyr Ala Phe Arg Ser Pro Glu Leu Arg Asp Ala Phe Lys
                    275                 280                 285

Lys Met Ile Phe Cys Ser Arg Tyr Trp
                    290                 295

(2) INFORMATION FOR SEQ ID NO:9:

(i) SEQUENCE CHARACTERISTICS:
        (A) LENGTH: 1108 base pairs
        (B) TYPE: nucleic acid
        (C) STRANDEDNESS: single
        (D) TOPOLOGY: linear (ii) MOLECULE TYPE: cDNA to mRNA (ix) FEATURE:
        (A) NAME/KEY: 5'UTR
        (B) LOCATION: 1..132

(ix) FEATURE:
        (A) NAME/KEY: CDS
        (B) LOCATION: 133..1026

(ix) FEATURE:
        (A) NAME/KEY: 3'UTR
        (B) LOCATION: 1027..1106

(xi) SEQUENCE DESCRIPTION: SEQ ID NO:9:

GGGGCCAGAA AGTTCCTGCT TCAGAGCAGA AGATCTTCAG CAAGAACTAC AAAGAAGAAA        60

AGATTCTGGA GAATCAATCA AGTTTCCTGT CAAGTTCCAG TAACGTTTCT GTCTTAACTG       120

CACACAGGAA AG ATG AAA CAC ATT CTC AAT CTG TAT GAA AAC CTC AAC          168
              Met Lys His Ile Leu Asn Leu Tyr Glu Asn Leu Asn
                1               5                   10

AGT ACA GCA AGA AAT AAC TCA GAC TGT CCT GCT GTG ATT TTG CCA GAA        216
Ser Thr Ala Arg Asn Asn Ser Asp Cys Pro Ala Val Ile Leu Pro Glu
            15                  20                  25

GAG ATA TTT TTC ACA GTA TCC ATT GTT GGG GTT TTG GAG AAC CTG ATG        264
Glu Ile Phe Phe Thr Val Ser Ile Val Gly Val Leu Glu Asn Leu Met
        30                  35                  40

GTC CTT CTG GCT GTG GCC AAG AAT AAG ATG CTT CAG TCG CCC ATG TAC        312
Val Leu Leu Ala Val Ala Lys Asn Lys Met Leu Gln Ser Pro Met Tyr
45                  50                  55                  60

TTT TTC ATC TGC AGC TTG GCT ATT TCC GAT ATG CTG GGG AGC ATG TAC        360
Phe Phe Ile Cys Ser Leu Ala Ile Ser Asp Met Leu Gly Ser Met Tyr
                65                  70                  75

AAG ATT TTG GAA AAC GTT CTG ATC ATG TTC AAA AAC ATG GGT TAC CTC        408
```

```
                                                        -continued

Lys Ile Leu Glu Asn Val Leu Ile Met Phe Lys Asn Met Gly Tyr Leu
            80                  85                  90

GAG CCT CGA GGC AGT TTT GAA AGC ACA GCA GAT GAT GTG GTG GAC TCC      456
Glu Pro Arg Gly Ser Phe Glu Ser Thr Ala Asp Asp Val Val Asp Ser
            95                 100                 105

CTG TTC ATC CTC TCC CTT CTC GGC TCC ATC TGC AGC CTG TCT GTG ATT      504
Leu Phe Ile Leu Ser Leu Leu Gly Ser Ile Cys Ser Leu Ser Val Ile
   110                 115                 120

GCC GCT GAC CGC TAC ACT ACA ATC TTC CAC GCT CTG CAG TAC CAC CGC      552
Ala Ala Asp Arg Tyr Thr Thr Ile Phe His Ala Leu Gln Tyr His Arg
125                 130                 135                 140

ATC ATG ACC CCC GCA CCG TGC CCT CGT CAT CTG ACG GTC CTC TGG CGA      600
Ile Met Thr Pro Ala Pro Cys Pro Arg His Leu Thr Val Leu Trp Arg
                145                 150                 155

GGC TGC ACA GGC AGT GGC ATT ACC ATC GTG ACC TTC TCC CAT CAC GTC      648
Gly Cys Thr Gly Ser Gly Ile Thr Ile Val Thr Phe Ser His His Val
            160                 165                 170

CCC ACA GTG ATC GCC TTC ACA GCG CTG TTC CCG CTG ATG CTG GCC TTC      696
Pro Thr Val Ile Ala Phe Thr Ala Leu Phe Pro Leu Met Leu Ala Phe
       175                 180                 185

ATC CTG TGC CTC TAC GTG CAC ATG TTC CTG CTG GCC CGC TCC CAC ACC      744
Ile Leu Cys Leu Tyr Val His Met Phe Leu Leu Ala Arg Ser His Thr
   190                 195                 200

AGG AGG ACC CCC TCC CTT CCC AAA GCC AAC ATG AGA GGG GCC GTC ACA      792
Arg Arg Thr Pro Ser Leu Pro Lys Ala Asn Met Arg Gly Ala Val Thr
205                 210                 215                 220

CTG ACT GTC CTG CTC GGG GTC TTC ATT TTC TGT TGG GCA CCC TTT GTC      840
Leu Thr Val Leu Leu Gly Val Phe Ile Phe Cys Trp Ala Pro Phe Val
                225                 230                 235

CTT CAT GTC CTC TTG ATG ACA TTC TGC CCA GCT GAC CCC TAC TGT GCC      888
Leu His Val Leu Leu Met Thr Phe Cys Pro Ala Asp Pro Tyr Cys Ala
            240                 245                 250

TGC TAC ATG TCC CTC TTC CAG GTG AAT GGT GTG TTG ATC ATG TGT AAT      936
Cys Tyr Met Ser Leu Phe Gln Val Asn Gly Val Leu Ile Met Cys Asn
       255                 260                 265

GCC ATC ATC GAC CCC TTC ATA TAT GCC TTT CGG AGC CCA GAG CTC AGG      984
Ala Ile Ile Asp Pro Phe Ile Tyr Ala Phe Arg Ser Pro Glu Leu Arg
   270                 275                 280

GTC GCA TTC AAA AAG ATG GTT ATC TGC AAC TGT TAC CAG TAG              1026
Val Ala Phe Lys Lys Met Val Ile Cys Asn Cys Tyr Gln *
285                 290                 295

AATGATTGGT CCCTGATTTT AGGAGCCACA GGGATATACT GTCAGGGACA GAGTAGCGTG   1086

ACAGACCAAC AACACTAGGA CT                                            1108

(2) INFORMATION FOR SEQ ID NO:10:

(i) SEQUENCE CHARACTERISTICS:
        (A) LENGTH: 297 amino acids
        (B) TYPE: amino acid
        (D) TOPOLOGY: linear (ii) MOLECULE TYPE: protein (xi) SEQUENCE DESCRIPTION: SEQ ID NO:10:

Met Lys His Ile Leu Asn Leu Tyr Glu Asn Leu Asn Ser Thr Ala Arg
  1               5                  10                  15

Asn Asn Ser Asp Cys Pro Ala Val Ile Leu Pro Glu Glu Ile Phe Phe
               20                  25                  30

Thr Val Ser Ile Val Gly Val Leu Glu Asn Leu Met Val Leu Leu Ala
           35                  40                  45
```

```
Val Ala Lys Asn Lys Met Leu Gln Ser Pro Met Tyr Phe Phe Ile Cys
         50                  55                  60

Ser Leu Ala Ile Ser Asp Met Leu Gly Ser Met Tyr Lys Ile Leu Glu
 65                  70                  75                  80

Asn Val Leu Ile Met Phe Lys Asn Met Gly Tyr Leu Glu Pro Arg Gly
                     85                  90                  95

Ser Phe Glu Ser Thr Ala Asp Asp Val Val Asp Ser Leu Phe Ile Leu
                100                 105                 110

Ser Leu Leu Gly Ser Ile Cys Ser Leu Ser Val Ile Ala Ala Asp Arg
                115                 120                 125

Tyr Thr Thr Ile Phe His Ala Leu Gln Tyr His Arg Ile Met Thr Pro
            130                 135                 140

Ala Pro Cys Pro Arg His Leu Thr Val Leu Trp Arg Gly Cys Thr Gly
145                 150                 155                 160

Ser Gly Ile Thr Ile Val Thr Phe Ser His His Val Pro Thr Val Ile
                165                 170                 175

Ala Phe Thr Ala Leu Phe Pro Leu Met Leu Ala Phe Ile Leu Cys Leu
            180                 185                 190

Tyr Val His Met Phe Leu Leu Ala Arg Ser His Thr Arg Arg Thr Pro
            195                 200                 205

Ser Leu Pro Lys Ala Asn Met Arg Gly Ala Val Thr Leu Thr Val Leu
210                 215                 220

Leu Gly Val Phe Ile Phe Cys Trp Ala Pro Phe Val Leu His Val Leu
225                 230                 235                 240

Leu Met Thr Phe Cys Pro Ala Asp Pro Tyr Cys Ala Cys Tyr Met Ser
                245                 250                 255

Leu Phe Gln Val Asn Gly Val Leu Ile Met Cys Asn Ala Ile Ile Asp
                260                 265                 270

Pro Phe Ile Tyr Ala Phe Arg Ser Pro Glu Leu Arg Val Ala Phe Lys
            275                 280                 285

Lys Met Val Ile Cys Asn Cys Tyr Gln
290                 295

(2) INFORMATION FOR SEQ ID NO:11:

(i) SEQUENCE CHARACTERISTICS:
        (A) LENGTH: 1338 base pairs
        (B) TYPE: nucleic acid
        (C) STRANDEDNESS: single
        (D) TOPOLOGY: linear (ii) MOLECULE TYPE: cDNA to mRNA (ix) FEATURE:
        (A) NAME/KEY: 5'UTR
        (B) LOCATION: 1..297

(ix) FEATURE:
        (A) NAME/KEY: CDS
        (B) LOCATION: 298..1269

(ix) FEATURE:
        (A) NAME/KEY: 3'UTR
        (B) LOCATION: 1270..1338

(xi) SEQUENCE DESCRIPTION: SEQ ID NO:11:

GGCTGTAACT GTAGCAACCG GTGTTGGGTG GGGATGAGAA GAGACCAGAG AGAGAGAGGG        60

TCAGAGCGAC AGGGGATGAG ACAGGCTGGT CAGAGTCTGC ACTGATTGTT GGAGACGCAA       120

AGGAAAGTTT TTTCTATGTC TCCAACCTCC CCCTCCTCCC CCGTTTCTCT CTGGAGAAAC       180
```

```
TAAAATGTAG ACTGGACAGC ATCCACAAGA GAAGCACCTA AAGAAGATT TTTTTTTCCC       240

AGCAGCTTGC TCAGGACCCT GCAGGAGCTG CAGCCGGAAC TGGTCCCGCC GATAACC        297

ATG AAC TCT TCC TGC TGC CCG TCC TCC TCT TAT CCG ACG CTG CCT AAC      345
Met Asn Ser Ser Cys Cys Pro Ser Ser Ser Tyr Pro Thr Leu Pro Asn
 1               5                  10                  15

CTC TCC CAG CAC CCT GCA GCC CCC TCT GCC AGC AAC CGG AGT GGC AGT      393
Leu Ser Gln His Pro Ala Ala Pro Ser Ala Ser Asn Arg Ser Gly Ser
                 20                  25                  30

GGG TTC TGC GAG CAG GTT TTC ATC AAG CCA GAG GTC TTC CTG GCA CTG      441
Gly Phe Cys Glu Gln Val Phe Ile Lys Pro Glu Val Phe Leu Ala Leu
             35                  40                  45

GGC ATC GTC AGT CTG ATG GAA AAC ATC CTG GTG ATC CTG GCT GTG GTG      489
Gly Ile Val Ser Leu Met Glu Asn Ile Leu Val Ile Leu Ala Val Val
 50                  55                  60

AGG AAC GGC AAC CTG CAC TCC CCC ATG TAC TTC TTC CTG CTG AGC CTG      537
Arg Asn Gly Asn Leu His Ser Pro Met Tyr Phe Phe Leu Leu Ser Leu
 65                  70                  75                  80

CTG CAG GCC GAC CTG CTG GTG AGC CTG TCC AAC TCC CTG GAG ACC ATC      585
Leu Gln Ala Asp Leu Leu Val Ser Leu Ser Asn Ser Leu Glu Thr Ile
                 85                  90                  95

ATG ATC GTG GTT ATC AAC AGC GAC TCC CTG ACC TTG GAG GAC CAA TTC      633
Met Ile Val Val Ile Asn Ser Asp Ser Leu Thr Leu Glu Asp Gln Phe
                100                 105                 110

ATC CAG CAC ATG GAC AAC ATC TTC GAC TCT ATG ATC TGC ATC TCC CTG      681
Ile Gln His Met Asp Asn Ile Phe Asp Ser Met Ile Cys Ile Ser Leu
             115                 120                 125

GTG GCC TCC ATC TGC AAC CTC CTG GCC ATC GCC GTG GAC AGG TAC GTC      729
Val Ala Ser Ile Cys Asn Leu Leu Ala Ile Ala Val Asp Arg Tyr Val
130                 135                 140

ACC ATC TTC TAT GCC CTC CGT TAC CAC AGC ATC ATG ACG GTT AGG AAA      777
Thr Ile Phe Tyr Ala Leu Arg Tyr His Ser Ile Met Thr Val Arg Lys
145                 150                 155                 160

GCC CTC TCC TTG ATC GTG GCC ATC TGG GTC TGC TGT GGC ATC TGC GGC      825
Ala Leu Ser Leu Ile Val Ala Ile Trp Val Cys Cys Gly Ile Cys Gly
                165                 170                 175

GTG ATG TTC ATC GTC TAC TCC GAG AGC AAG ATG GTC ATC GTG TGC CTC      873
Val Met Phe Ile Val Tyr Ser Glu Ser Lys Met Val Ile Val Cys Leu
            180                 185                 190

ATC ACC ATG TTC TTC GCC ATG GTG CTC CTC ATG GGC ACC CTG TAC ATC      921
Ile Thr Met Phe Phe Ala Met Val Leu Leu Met Gly Thr Leu Tyr Ile
        195                 200                 205

CAC ATG TTC CTC TTC GCC AGG CTG CAC GTC CAG CGC ATC GCG GCA CTG      969
His Met Phe Leu Phe Ala Arg Leu His Val Gln Arg Ile Ala Ala Leu
    210                 215                 220

CCA CCT GCT GAC GGG CTA GCC CCG CAG CAG CAC TCG TGC ATG AAG GGG     1017
Pro Pro Ala Asp Gly Leu Ala Pro Gln Gln His Ser Cys Met Lys Gly
225                 230                 235                 240

GCC GTC ACC ATC ACC ATC CTG CTG GGG GTT TTC ATC TTC TGC TGG GCG     1065
Ala Val Thr Ile Thr Ile Leu Leu Gly Val Phe Ile Phe Cys Trp Ala
                245                 250                 255

CCT TTC TTC CTC CAC CTG GTC CTC ATC ATC ACC TGC CCC ACC AAC CCC     1113
Pro Phe Phe Leu His Leu Val Leu Ile Ile Thr Cys Pro Thr Asn Pro
            260                 265                 270

TAC TGC ATC TGC TAC ACG GCG CAC TTC AAC ACC TAC CTG GTT CTC ATC     1161
Tyr Cys Ile Cys Tyr Thr Ala His Phe Asn Thr Tyr Leu Val Leu Ile
        275                 280                 285

ATG TGC AAC TCT GTC ATC GAC CCC CTC ATC TAC GCC TTC CGC AGC CTG     1209
Met Cys Asn Ser Val Ile Asp Pro Leu Ile Tyr Ala Phe Arg Ser Leu
```

```
                290                 295                 300
GAG CTG CGA AAC ACC TTC AAG GAG ATT CTC TGC GGT TGC AAT GGC ATG     1257
Glu Leu Arg Asn Thr Phe Lys Glu Ile Leu Cys Gly Cys Asn Gly Met
305                 310                 315                 320

AAC GTG GGC TAG GAACCCCCGA GGAGGTGTTC CACGGCTAGC CAAGAGAGAA         1309
Asn Val Gly *

AAGCAATGCT CAGGTGAGAC ACAGAAGGG                                     1338
```

(2) INFORMATION FOR SEQ ID NO:12:

(i) SEQUENCE CHARACTERISTICS:
        (A) LENGTH: 323 amino acids
        (B) TYPE: amino acid
        (D) TOPOLOGY: linear (ii) MOLECULE TYPE: protein (xi) SEQUENCE DESCRIPTION: SEQ ID NO:12:

```
Met Asn Ser Ser Cys Cys Pro Ser Ser Tyr Pro Thr Leu Pro Asn
1               5                   10                  15

Leu Ser Gln His Pro Ala Ala Pro Ser Ala Ser Asn Arg Ser Gly Ser
                20                  25                  30

Gly Phe Cys Glu Gln Val Phe Ile Lys Pro Glu Val Phe Leu Ala Leu
            35                  40                  45

Gly Ile Val Ser Leu Met Glu Asn Ile Leu Val Ile Leu Ala Val Val
        50                  55                  60

Arg Asn Gly Asn Leu His Ser Pro Met Tyr Phe Phe Leu Leu Ser Leu
65                  70                  75                  80

Leu Gln Ala Asp Leu Leu Val Ser Leu Ser Asn Ser Leu Glu Thr Ile
                85                  90                  95

Met Ile Val Val Ile Asn Ser Asp Ser Leu Thr Leu Glu Asp Gln Phe
            100                 105                 110

Ile Gln His Met Asp Asn Ile Phe Asp Ser Met Ile Cys Ile Ser Leu
        115                 120                 125

Val Ala Ser Ile Cys Asn Leu Leu Ala Ile Ala Val Asp Arg Tyr Val
    130                 135                 140

Thr Ile Phe Tyr Ala Leu Arg Tyr His Ser Ile Met Thr Val Arg Lys
145                 150                 155                 160

Ala Leu Ser Leu Ile Val Ala Ile Trp Val Cys Cys Gly Ile Cys Gly
                165                 170                 175

Val Met Phe Ile Val Tyr Ser Glu Ser Lys Met Val Ile Val Cys Leu
            180                 185                 190

Ile Thr Met Phe Phe Ala Met Val Leu Leu Met Gly Thr Leu Tyr Ile
        195                 200                 205

His Met Phe Leu Phe Ala Arg Leu His Val Gln Arg Ile Ala Ala Leu
    210                 215                 220

Pro Pro Ala Asp Gly Leu Ala Pro Gln Gln His Ser Cys Met Lys Gly
225                 230                 235                 240

Ala Val Thr Ile Thr Ile Leu Leu Gly Val Phe Ile Phe Cys Trp Ala
                245                 250                 255

Pro Phe Phe Leu His Leu Val Leu Ile Ile Thr Cys Pro Thr Asn Pro
            260                 265                 270

Tyr Cys Ile Cys Tyr Thr Ala His Phe Asn Thr Tyr Leu Val Leu Ile
        275                 280                 285

Met Cys Asn Ser Val Ile Asp Pro Leu Ile Tyr Ala Phe Arg Ser Leu
    290                 295                 300
```

```
Glu Leu Arg Asn Thr Phe Lys Glu Ile Leu Cys Gly Cys Asn Gly Met
305                 310                 315                 320

Asn Val Gly
```

(2) INFORMATION FOR SEQ ID NO:13:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..30
        (D) OTHER INFORMATION: /function = "Degenerate
            oligonucleotide primer (sense)"

(xi) SEQUENCE DESCRIPTION: SEQ ID NO:13:

```
GAGTCGACCR CCCATGTAYT DYTTCATCTG                                    30
```

(2) INFORMATION FOR SEQ ID NO:14:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..30
        (D) OTHER INFORMATION: /function = "Degenerate
            oligonucleotide primer (sense)"

(xi) SEQUENCE DESCRIPTION: SEQ ID NO:14:

```
CAGAATTCGG AARGCRTAKA TGARGGGGTC                                    30
```

(2) INFORMATION FOR SEQ ID NO:15:

(i) SEQUENCE CHARACTERISTICS:
        (A) LENGTH: 1671 base pairs
        (B) TYPE: nucleic acid
        (C) STRANDEDNESS: single
        (D) TOPOLOGY: linear (ii) MOLECULE TYPE: cDNA to mRNA (ix) FEATURE:
        (A) NAME/KEY: 5'UTR
        (B) LOCATION: 1..393

(ix) FEATURE:
        (A) NAME/KEY: CDS
        (B) LOCATION: 394..1389

(ix) FEATURE:
        (A) NAME/KEY: 3'UTR
        (B) LOCATION: 1390..1671

(xi) SEQUENCE DESCRIPTION: SEQ ID NO:15:

```
AGCTTCCGAG AGGCAGCCGA TGTGAGCATG TGCGCACAGA TTCGTCTCCC AATGGCATGG    60

CAGCTTCAAG GAAAATTATT TTGAACAGAC TTGAATGCAT AAGATTAAAG TTAAAGCAGA   120

AGTGAGAACA AGAAAGCAAA GAGCAGACTC TTTCAACTGA GAATGAATAT TTTGAAGCCC   180
```

-continued

```
AAGATTTTAA CGTGATGATG ATTAGAGTCG TACCTAAAAG AGACTAAAAA CTCCATGTCA      240

AGCTCTGGAC TTGTGACATT TACTCACAGC AGGCATGGCA ATTTTAGCCT CACAACTTTC      300

AGACAGATAA AGACTTGGAG GAAATAACTG AGACGACTCC CTGACCCAGG AGGTTAAATC      360

AATTCAGGGG GACACTGGAA TTCTCCTGCC AGC ATG GTG AAC TCC ACC CAC CGT      414
                                    Met Val Asn Ser Thr His Arg
                                      1               5

GGG ATG CAC ACT TCT CTG CAC CTC TGG AAC CGC AGC AGT TAC AGA CTG        462
Gly Met His Thr Ser Leu His Leu Trp Asn Arg Ser Ser Tyr Arg Leu
         10                  15                  20

CAC AGC AAT GCC AGT GAG TCC CTT GGA AAA GGC TAC TCT GAT GGA GGG        510
His Ser Asn Ala Ser Glu Ser Leu Gly Lys Gly Tyr Ser Asp Gly Gly
     25                  30                  35

TGC TAC GCG CAA CTT TTT GTC TCT CCT GAG GTG TTT GTG ACT CTG GGT        558
Cys Tyr Ala Gln Leu Phe Val Ser Pro Glu Val Phe Val Thr Leu Gly
 40                  45                  50                  55

GTG ATC AGC TTG TTG GAG AAT ATC TTA GAG ATT GTG GCA ATA GCC AAG        606
Val Ile Ser Leu Leu Glu Asn Ile Leu Glu Ile Val Ala Ile Ala Lys
                 60                  65                  70

AAC AAG AAT CTG CAT TCA CCC ATG TAC TTT TTC ATC TGC AGC TTG GCT        654
Asn Lys Asn Leu His Ser Pro Met Tyr Phe Phe Ile Cys Ser Leu Ala
             75                  80                  85

GTG GCT GAT ATG CTG GTG AGC GTT TCA AAT GGA TCA GAA ACC ATT ATC        702
Val Ala Asp Met Leu Val Ser Val Ser Asn Gly Ser Glu Thr Ile Ile
         90                  95                 100

ATC ACC CTA TTA AAC CGT ACA GAT ACG GAT GCA CAG AGT TTC ACA GTG        750
Ile Thr Leu Leu Asn Arg Thr Asp Thr Asp Ala Gln Ser Phe Thr Val
    105                 110                 115

AAT ATT GAT AAT GTC ATT GAC TCG GTG ATC TGT AGC TCC TTG CTT GCA        798
Asn Ile Asp Asn Val Ile Asp Ser Val Ile Cys Ser Ser Leu Leu Ala
120                 125                 130                 135

TCC ATT TGC AGC CTG CTT TCA ATT GCA GTG GAC AGG TAC TTT ACT ATC        846
Ser Ile Cys Ser Leu Leu Ser Ile Ala Val Asp Arg Tyr Phe Thr Ile
                140                 145                 150

TTC TAT GCT CTC CAG TAC CAT AAC ATT ATG ACA GTT AAG CGG GTT GGG        894
Phe Tyr Ala Leu Gln Tyr His Asn Ile Met Thr Val Lys Arg Val Gly
            155                 160                 165

ATC AGC ATA AGT TGT ATC TGG GCA GCT TGC ACG GTT TCA GGT ATT TTG        942
Ile Ser Ile Ser Cys Ile Trp Ala Ala Cys Thr Val Ser Gly Ile Leu
        170                 175                 180

TTC ATC ATT TAC TCA GAT AGT AGT GCT GTC ATC ATC TGC CTC ATC ACC        990
Phe Ile Ile Tyr Ser Asp Ser Ser Ala Val Ile Ile Cys Leu Ile Thr
    185                 190                 195

ATG TTC TTC ACC ATG CTG GCT CTC ATG GCT TCT CTC TAT GTC CAC CTG       1038
Met Phe Phe Thr Met Leu Ala Leu Met Ala Ser Leu Tyr Val His Leu
200                 205                 210                 215

TTC CTG ATG GCC AGG CTT CAC ATT AAG AGG ATT GCT GTC CTC CCC GGC       1086
Phe Leu Met Ala Arg Leu His Ile Lys Arg Ile Ala Val Leu Pro Gly
                220                 225                 230

ACT GGT GCC ATC CGC CAA GGT GCC AAT ATG AAG GGA GCG ATT ACC TTG       1134
Thr Gly Ala Ile Arg Gln Gly Ala Asn Met Lys Gly Ala Ile Thr Leu
            235                 240                 245

ACC ATC CTG ATT GGC GTC TTT GTT GTC TGC TGG GCC CCA TTC TTC CTC       1182
Thr Ile Leu Ile Gly Val Phe Val Val Cys Trp Ala Pro Phe Phe Leu
        250                 255                 260

CAC TTA ATA TTC TAC ATC TCT TGT CCT CAG AAT CCA TAT TGT GTG TGC       1230
His Leu Ile Phe Tyr Ile Ser Cys Pro Gln Asn Pro Tyr Cys Val Cys
    265                 270                 275

TTC ATG TCT CAC TTT AAC TTG TAT CTC ATA CTG ATC ATG TGT AAT TCA       1278
```

```
Phe Met Ser His Phe Asn Leu Tyr Leu Ile Leu Ile Met Cys Asn Ser
280                 285                 290                 295

ATC ATC GAT CCT CTG ATT TAT GCA CTC CGG AGT CAA GAA CTG AGG AAA    1326
Ile Ile Asp Pro Leu Ile Tyr Ala Leu Arg Ser Gln Glu Leu Arg Lys
            300                 305                 310

ACC TTC AAA GAG ATC ATC TCT TCC TAT CCC CTG GGA GGC CTT TGT GAC    1374
Thr Phe Lys Glu Ile Ile Ser Ser Tyr Pro Leu Gly Gly Leu Cys Asp
            315                 320                 325

TTG TCT AGC AGA TAT TAAATGGGGA CAGAGCACGC AATATAGGAA CATCCATAAG    1429
Leu Ser Ser Arg Tyr
            330

AGACTTTTC ACTCTTACCC TACCTGAATA TTCTACTTCT GCAACAGCTT TCTCTTCCGT    1489

GTAGGGTACT GGTTGAGATA TCCATTGTGT AAATTTAAGC CTATGATTTT TAATGAGAAA    1549

AAATGCCCAG TCTCTGTATT ATTTCCAATC TCATGCTACT TTTTTGGCCA TAAAATATGA    1609

ATCTATGTTA TAGGTTGTAG GCACTGTGGA TTTACAAAAA GAAAAGTCCT TATTAAAAGA    1669

TT                                                                  1671

(2) INFORMATION FOR SEQ ID NO:16:

(i) SEQUENCE CHARACTERISTICS:
        (A) LENGTH: 332 amino acids
        (B) TYPE: amino acid
        (D) TOPOLOGY: linear (ii) MOLECULE TYPE: protein (xi) SEQUENCE DESCRIPTION: SEQ ID NO:16:

Met Val Asn Ser Thr His Arg Gly Met His Thr Ser Leu His Leu Trp
1               5                   10                  15

Asn Arg Ser Ser Tyr Arg Leu His Ser Asn Ala Ser Glu Ser Leu Gly
                20                  25                  30

Lys Gly Tyr Ser Asp Gly Gly Cys Tyr Ala Gln Leu Phe Val Ser Pro
            35                  40                  45

Glu Val Phe Val Thr Leu Gly Val Ile Ser Leu Leu Glu Asn Ile Leu
        50                  55                  60

Glu Ile Val Ala Ile Ala Lys Asn Lys Asn Leu His Ser Pro Met Tyr
65                  70                  75                  80

Phe Phe Ile Cys Ser Leu Ala Val Ala Asp Met Leu Val Ser Val Ser
                85                  90                  95

Asn Gly Ser Glu Thr Ile Ile Thr Leu Leu Asn Arg Thr Asp Thr
                100                 105                 110

Asp Ala Gln Ser Phe Thr Val Asn Ile Asp Asn Val Ile Asp Ser Val
            115                 120                 125

Ile Cys Ser Ser Leu Leu Ala Ser Ile Cys Ser Leu Leu Ser Ile Ala
130                 135                 140

Val Asp Arg Tyr Phe Thr Ile Phe Tyr Ala Leu Gln Tyr His Asn Ile
145                 150                 155                 160

Met Thr Val Lys Arg Val Gly Ile Ser Ile Ser Cys Ile Trp Ala Ala
                165                 170                 175

Cys Thr Val Ser Gly Ile Leu Phe Ile Ile Tyr Ser Asp Ser Ser Ala
            180                 185                 190

Val Ile Ile Cys Leu Ile Thr Met Phe Phe Thr Met Leu Ala Leu Met
        195                 200                 205

Ala Ser Leu Tyr Val His Leu Phe Leu Met Ala Arg Leu His Ile Lys
210                 215                 220
```

-continued

```
Arg Ile Ala Val Leu Pro Gly Thr Gly Ala Ile Arg Gln Gly Ala Asn
225                 230                 235                 240

Met Lys Gly Ala Ile Thr Leu Thr Ile Leu Ile Gly Val Phe Val Val
            245                 250                 255

Cys Trp Ala Pro Phe Phe Leu His Leu Ile Phe Tyr Ile Ser Cys Pro
            260                 265                 270

Gln Asn Pro Tyr Cys Val Cys Phe Met Ser His Phe Asn Leu Tyr Leu
        275                 280                 285

Ile Leu Ile Met Cys Asn Ser Ile Ile Asp Pro Leu Ile Tyr Ala Leu
    290                 295                 300

Arg Ser Gln Glu Leu Arg Lys Thr Phe Lys Glu Ile Ile Ser Ser Tyr
305                 310                 315                 320

Pro Leu Gly Gly Leu Cys Asp Leu Ser Ser Arg Tyr
                325                 330
```

(2) INFORMATION FOR SEQ ID NO:17:

(i) SEQUENCE CHARACTERISTICS:
        (A) LENGTH: 978 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..975

(xi) SEQUENCE DESCRIPTION: SEQ ID NO:17:

```
ATG AAC TCC TCC TCC ACC CTG ACT GTA TTG AAT CTT ACC CTG AAC GCC        48
Met Asn Ser Ser Ser Thr Leu Thr Val Leu Asn Leu Thr Leu Asn Ala
1               5                   10                  15

TCA GAG GAT GGC ATT TTA GGA TCA AAT GTC AAG AAC AAG TCT TTG GCC        96
Ser Glu Asp Gly Ile Leu Gly Ser Asn Val Lys Asn Lys Ser Leu Ala
            20                  25                  30

TGT GAA GAA ATG GGC ATT GCC GTG GAG GTG TTC CTG ACC CTG GGT CTC       144
Cys Glu Glu Met Gly Ile Ala Val Glu Val Phe Leu Thr Leu Gly Leu
        35                  40                  45

GTC AGC CTC TTA GAG AAC ATC CTG GTC ATT GGG GCC ATA GTA AAG AAC       192
Val Ser Leu Leu Glu Asn Ile Leu Val Ile Gly Ala Ile Val Lys Asn
    50                  55                  60

AAA AAC CTG CAC TCA CCC ATG TAC TTC TTT GTG GGC AGC TTA GCC GTG       240
Lys Asn Leu His Ser Pro Met Tyr Phe Phe Val Gly Ser Leu Ala Val
65                  70                  75                  80

GCC GAC ATG CTG GTG AGC ATG TCC AAT GCC TGG GAG ACT GTC ACC ATA       288
Ala Asp Met Leu Val Ser Met Ser Asn Ala Trp Glu Thr Val Thr Ile
                85                  90                  95

TAC TTG CTA AAT AAT AAA CAC CTG GTG ATA GCC GAC ACC TTT GTG CGA       336
Tyr Leu Leu Asn Asn Lys His Leu Val Ile Ala Asp Thr Phe Val Arg
            100                 105                 110

CAC ATC GAC AAC GTG TTC GAC TCC ATG ATC TGC ATC TCT GTG GTG GCC       384
His Ile Asp Asn Val Phe Asp Ser Met Ile Cys Ile Ser Val Val Ala
        115                 120                 125

TCG ATG TGC AGT TTG CTG GCC ATT GCG GTG GAT AGG TAC ATC ACC ATC       432
Ser Met Cys Ser Leu Leu Ala Ile Ala Val Asp Arg Tyr Ile Thr Ile
130                 135                 140

TTC TAT GCC TTG CGC TAC CAC CAC ATC ATG ACC GCG AGG CGC TCG GGG       480
Phe Tyr Ala Leu Arg Tyr His His Ile Met Thr Ala Arg Arg Ser Gly
145                 150                 155                 160

GTG ATC ATC GCC TGC ATT TGG ACC TTC TGC ATA AGC TGC GGC ATT GTT       528
```

```
Val Ile Ile Ala Cys Ile Trp Thr Phe Cys Ile Ser Cys Gly Ile Val
                165                 170                 175

TTC ATC ATC TAC TAT GAG TCC AAG TAT GTG ATC ATT TGC CTC ATC TCC        576
Phe Ile Ile Tyr Tyr Glu Ser Lys Tyr Val Ile Ile Cys Leu Ile Ser
        180                 185                 190

ATG TTC TTC ACC ATG CTG TTC TTC ATG GTG TCT CTG TAT ATA CAC ATG        624
Met Phe Phe Thr Met Leu Phe Phe Met Val Ser Leu Tyr Ile His Met
            195                 200                 205

TTC CTC CTG GCC CGG AAC CAT GTC AAG CGG ATA GCA GCT TCC CCC AGA        672
Phe Leu Leu Ala Arg Asn His Val Lys Arg Ile Ala Ala Ser Pro Arg
        210                 215                 220

TAC AAC TCC GTG AGG CAA AGG ACC AGC ATG AAG GGG GCT ATT ACC CTC        720
Tyr Asn Ser Val Arg Gln Arg Thr Ser Met Lys Gly Ala Ile Thr Leu
225                 230                 235                 240

ACC ATG CTA CTG GGG ATT TTC ATT GTC TGC TGG TCT CCC TTC TTT CTT        768
Thr Met Leu Leu Gly Ile Phe Ile Val Cys Trp Ser Pro Phe Phe Leu
                245                 250                 255

CAC CTT ATC TTA ATG ATC TCC TGC CCT CAG AAC GTC TAC TGC TCT TGC        816
His Leu Ile Leu Met Ile Ser Cys Pro Gln Asn Val Tyr Cys Ser Cys
            260                 265                 270

TTT ATG TCT TAC TTC AAC ATG TAC CTT ATA CTC ATC ATG TGC AAC TCC        864
Phe Met Ser Tyr Phe Asn Met Tyr Leu Ile Leu Ile Met Cys Asn Ser
        275                 280                 285

GTG ATC GAT CCT CTC ATC TAC GCC CTC CGC AGC CAA GAG ATG CGG AGG        912
Val Ile Asp Pro Leu Ile Tyr Ala Leu Arg Ser Gln Glu Met Arg Arg
    290                 295                 300

ACC TTT AAG GAG ATC GTC TGT TGT CAC GGA TTC CGG CGA CCT TGT AGG        960
Thr Phe Lys Glu Ile Val Cys Cys His Gly Phe Arg Arg Pro Cys Arg
305                 310                 315                 320

CTC CTT GGC GGG TAT TAA                                                978
Leu Leu Gly Gly Tyr
                325

(2) INFORMATION FOR SEQ ID NO:18:

(i) SEQUENCE CHARACTERISTICS:
        (A) LENGTH: 325 amino acids
        (B) TYPE: amino acid
        (D) TOPOLOGY: linear (ii) MOLECULE TYPE: protein (xi) SEQUENCE DESCRIPTION: SEQ ID NO:18:

Met Asn Ser Ser Ser Thr Leu Thr Val Leu Asn Leu Thr Leu Asn Ala
 1               5                  10                  15

Ser Glu Asp Gly Ile Leu Gly Ser Asn Val Lys Asn Lys Ser Leu Ala
                20                  25                  30

Cys Glu Glu Met Gly Ile Ala Val Glu Val Phe Leu Thr Leu Gly Leu
            35                  40                  45

Val Ser Leu Leu Glu Asn Ile Leu Val Ile Gly Ala Ile Val Lys Asn
        50                  55                  60

Lys Asn Leu His Ser Pro Met Tyr Phe Phe Val Gly Ser Leu Ala Val
65                  70                  75                  80

Ala Asp Met Leu Val Ser Met Ser Asn Ala Trp Glu Thr Val Thr Ile
                85                  90                  95

Tyr Leu Leu Asn Asn Lys His Leu Val Ile Ala Asp Thr Phe Val Arg
                100                 105                 110

His Ile Asp Asn Val Phe Asp Ser Met Ile Cys Ile Ser Val Val Ala
            115                 120                 125
```

```
Ser Met Cys Ser Leu Leu Ala Ile Ala Val Asp Arg Tyr Ile Thr Ile
    130                 135                 140
Phe Tyr Ala Leu Arg Tyr His His Ile Met Thr Ala Arg Arg Ser Gly
145                 150                 155                 160
Val Ile Ile Ala Cys Ile Trp Thr Phe Cys Ile Ser Cys Gly Ile Val
                165                 170                 175
Phe Ile Ile Tyr Tyr Glu Ser Lys Tyr Val Ile Ile Cys Leu Ile Ser
                180                 185                 190
Met Phe Phe Thr Met Leu Phe Phe Met Val Ser Leu Tyr Ile His Met
            195                 200                 205
Phe Leu Leu Ala Arg Asn His Val Lys Arg Ile Ala Ala Ser Pro Arg
        210                 215                 220
Tyr Asn Ser Val Arg Gln Arg Thr Ser Met Lys Gly Ala Ile Thr Leu
225                 230                 235                 240
Thr Met Leu Leu Gly Ile Phe Ile Val Cys Trp Ser Pro Phe Phe Leu
                245                 250                 255
His Leu Ile Leu Met Ile Ser Cys Pro Gln Asn Val Tyr Cys Ser Cys
                260                 265                 270
Phe Met Ser Tyr Phe Asn Met Tyr Leu Ile Leu Ile Met Cys Asn Ser
            275                 280                 285
Val Ile Asp Pro Leu Ile Tyr Ala Leu Arg Ser Gln Glu Met Arg Arg
        290                 295                 300
Thr Phe Lys Glu Ile Val Cys Cys His Gly Phe Arg Arg Pro Cys Arg
305                 310                 315                 320
Leu Leu Gly Gly Tyr
                325

(2) INFORMATION FOR SEQ ID NO:19:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..32
        (D) OTHER INFORMATION: /function = "Degenerate
            oligonucleotide primer (antisense)"

(xi) SEQUENCE DESCRIPTION: SEQ ID NO:19:

GAATTCGACG TCACAGTATG ACGGCCATGG                                    30
```

METHODS AND REAGENTS FOR DISCOVERING AND USING MAMMALIAN MELANOCORTIN RECEPTOR AGONISTS AND ANTAGONISTS TO MODULATE FEEDING BEHAVIOR IN ANIMALS

This application is a continuation-in-part of U.S. Ser. No. 08/466,906, filed Jun. 6, 1995, now U.S. Pat. No. 5,849,871 which is a divisional of U.S. Ser. No. 07/886,979, filed May. 21, 1992, now U.S. Pat. No. 5,270,605, issued Dec. 14 1993. This application is also a continuation-in-part of U.S. Ser. No. 08/478,992, filed Jun. 7, 1995, now U.S. Pat. No. 5,773,229, which is a divisional of U.S. Ser. No. 08/077,673, filed Jun. 15, 1993, now U.S. Pat. No. 5,554,729, which is a divisional of U.S. Ser. No. 07/866,560, filed Apr. 10, 1992, now U.S. Pat. No. 5,280,112, issued Jan. 18, 1994. This application is also a continuation-in-part of U.S. Ser. No. 08/044,812, filed Apr. 8, 1993, now U.S. Pat. No. 5,837,521.

This invention was made with government support under R29DK41921, R01DK43859, P01DK44239, AR42415 and HD30236 by the National Institutes of Health. The government has certain rights in the invention.

BACKGROUND OF THE INVENTION

1. Field of the Invention

The present invention relates to the cloning, expression and functional characterization of mammalian melanocortin receptor genes. The invention provides nucleic acid encoding mammalian melanocortin receptors, recombinant expression constructs comprising said nucleic acid, and mammalian cells into which said recombinant expression constructs have been introduced, and that express functional mammalian melanocortin receptors. The invention also provides a panel of such transformed mammalian cells expressing melanocortin receptors for screening compounds for receptor agonist and antagonist activity. The invention provides methods for using such panels of melanocortin receptor-expressing mammalian cells to specifically detect and identify agonists and antagonists for each melanocortin receptor, as well as patterns of agonist and antagonist activity of said compounds for the class of melanocortin receptors. Such screening methods provide a means for identifying compounds with patterns of melanocortin agonist and antagonist activity which are associated with the capacity to influence or modify physiological funtion and behavior, particularly metabolism and feeding behavior.

2. Background of the Invention

The proopiomelanocortin (POMC) gene product is processed to produce a large number of biologically active peptides. Two of these peptides, α-melanocyte stimulating hormone (αMSH), and adrenocorticotropic hormone (ACTH) have well understood roles in control of melanocyte and adrenocortical function, respectively. Both of these hormones are also found in a variety of forms with unknown functions, for example, γ-melanocyte stimulating hormone (γMSH), which has little or no ability to stimulate pigmentation (Ling et al., 1979, *Life Sci.* 25: 1773–1780; Slominski et al., 1992, *Life Sci.* 50: 1103–1108). A melanocortin receptor gene specific for each of the αMSH, ACTH and γMSH hormones has been discovered by some of the present inventors (see U.S. Pat. Nos. 5,280,112, 5,532,347 and U.S. application Ser. No. 08/044,812, incorporated by reference herein). In addition, two other melanocortin receptor genes have been discovered by some of the present inventors (see Lu et al, 1994, *Nature* 371: 799–802; Mountjoy et al, 1994, *Molec. Endocrinol.* 8: 1298–1308) and others (see Gantz et al., 1993, *J. Biol. Chem.* 268: 15174–15179 and Labbe et al., 1994, *Biochem.* 33: 4543–4549).

Along with the well-recognized activities of αMSH in melanocytes and ACTH in adrenal and pituitary glands, the melanocortin peptides also have a diverse array of biological activities in other tissues, including the brain and immune system, and bind to specific receptors in these tissues with a distinct pharmacology (see, Hanneman et al., in *Peptide Hormone as Prohormones*, G. Martinez, ed. (Ellis Horwood Ltd.: Chichester, UK) pp. 53–82; DeWied & Jolles, 1982, *Physiol. Rev.* 62: 976–1059 for reviews). A complete understanding of these peptides and their diverse biological activities requires the isolation and characterization of their corresponding receptors. Some biochemical studies have been reported in the prior art.

Shimuze, 1985, *Yale J. Biol. Med.* 58: 561–570 discusses the physiology of melanocyte stimulating hormone.

Tatro & Reichlin, 1987, *Endocrinology* 121: 1900–1907 disclose that MSH receptors are widely distributed in rodent tissues.

Sola et al., 1989, *J. Biol. Chem.* 264: 14277–14280 disclose the molecular weight characterization of mouse and human MSH receptors linked to radioactively and photoaffinity labeled MSH analogues.

Siegrist et al., 1991, *J. Receptor Res.* 11: 323–331 disclose the quantification of receptors on mouse melanoma tissue by receptor autoradiography.

Cone & Mountjoy, U.S. patent application Ser. No. 07/866,979, filed Apr. 10, 1992, disclose the isolation of human and mouse α-MSH receptor genes and uses thereof (incorporated herein by reference).

Cone & Mountjoy, U.S. patent application Ser. No. 07/866,560, filed Apr. 10, 1992, disclose the isolation of human and bovine ACTH receptor genes and uses thereof (incorporated herein by reference).

Mountjoy et al., 1992, *Science* 257: 1248–1251 disclose the isolation of cDNAs encoding mammalian ACTH and MSH receptor proteins.

POMC neurons are present in only two regions of the brain, the arcuate nucleus of the hypothalamus, and the nucleus of the solitary tract of the brain stem. Neurons from both sites project to a number of hypothalamic nuclei known to be important in feeding behavior, including the paraventricular nucleus, lateral hypothalamic area, and ventromedial hypothalamic nucleus. While previous reports have claimed both stimulatory and inhibitory effects of α-MSH on feeding behavior (see Shimizu et al., 1989, *Life Sci.* 45: 543–552; Tsujii et al., 1989, *Brian Res. Bull.* 23: 165–169), knowledge of specific melanocortin receptors, their location within the central nervous system and the necessary pharmacological tools were not sufficiently developed at that time to allow the resolution of this issue. The present inventors have shown herein that a novel antagonist of the MC-3 and MC-4 melanocortin receptors can substantially increase food consumption in animals engaged in normal or fast-induced feeding behavior. This is consistent with expression of both MC-3 and MC-4 receptor mRNAs at these sites in in situ hybridization studies (Roselli-Rehfuss et al., 1993, *Proc. Natl. Acad. Sci. USA* 90: 8856–8860; Mountjoy et al., 1994, Molec. Endocrinol. 8: 1298– 1308). Moreover, the regulation of arcuate nucleus POMC gene expression is consistent with an inhibitory role for POMC in feeding behavior. POMC mRNA levels are decreased following a fast (Bergendahl et al., 1992, *Neuroendocrinol.* 56: 913–920; Brady et al., 1990, *Neuroendocrinol.* 52: 441–447), and a significant diurnal variation in POMC mRNA levels in the arcuate nucleus is seen in rat, with the nadir occurring around the onset of nighttime feeding at 1800 hrs (Steiner et al., 1994, FASEB J. 8: 479–488).

Thus, the experimental evidence indicates that POMC neurons play an important role in tonic inhibition of feeding behavior, wherein obesity results from a chronic disruption of this inhibitory tone by antagonism of central melanocortin receptors in at least one animal model (agouti).

These results reveal for the first time a need in the art for a means for characterizing mammalian melanocortin receptor agonists and antagonists in vitro for the development of compounds that affect feeding behavior in animals.

SUMMARY OF THE INVENTION

The present invention provides a biological screening system for identifying and characterizing compounds that are agonists or antagonists of mammalian melanocortin receptors. The biological screening system of the invention comprises a panel of transformed mammalian cells comprising a recombinant expression construct encoding a mammalian melanocortin receptor, and expressing said receptor thereby. The invention provides such a panel of transformed mammalian cells wherein the panel comprises cells expressing each type of mammalian melanocortin receptor. Thus, the invention also provides nucleic acid encoding mammalian melanocortin receptors, recombinant expression constructs comprising said nucleic acid, and mammalian cells into which said recombinant expression constructs have been introduced, and that express functional mammalian melanocortin receptors. Methods for using such panels of melanocortin receptor-expressing mammalian cells to specifically detect and identify agonists and antagonists for each melanocortin receptor, as well as patterns of agonist and antagonist activity of said compounds for the class of melanocortin receptors, are also provided. Such screening methods provide a means for identifying compounds with patterns of melanocortin agonist and antagonist activity which are associated with the capacity to influence or modify metabolism and behavior in an animal, particularly feeding behavior.

Thus, the invention provides in a first aspect a biological screening panel for determining the melanocortin receptor agonist/antagonist profile of a test compound. The panel comprises a first mammalian cell comprising a recombinant expression construct encoding a mammalian melanocortin receptor that is the α-MSH (MC-1) receptor. The panel also comprises a second mammalian cell comprising a recombinant expression construct encoding a mammalian melanocortin receptor that is the ACTH (MC-2) receptor. The panel also comprises a third mammalian cell comprising a recombinant expression construct encoding a mammalian melanocortin receptor that is the MC-3 receptor. The panel also comprises a fourth mammalian cell comprising a recombinant expression construct encoding a mammalian melanocortin receptor that is the MC-4 receptor. The panel also comprises a fifth mammalian cell comprising a recombinant expression construct encoding a mammalian melanocortin receptor that is the MC-5 receptor. As provided by the invention, each mammalian cell expresses the melanocortin receptor encoded by the recombinant expression construct comprised by said cell.

In preferred embodiments, the melanocortin receptors encoded by the recombinant expression constructs comprising the transformed mammalian cells comprising the panel are mouse MC-1 receptor (SEQ ID Nos.: 3 and 4); human MC-1 receptor (SEQ ID Nos.: 5 and 6), human MC-2 (ACTH) receptor (SEQ ID Nos.: 7 and 8), bovine MC-2 receptor (SEQ ID Nos.: 9 and 10), rat MC-3 receptor (SEQ ID Nos.: 11 and 12), human MC-4 receptor (SEQ ID Nos.: 15 and 16) and human MC-5 receptor (SEQ ID Nos.: 17 and 18).

In a second aspect, the invention provides a method for using the melanocortin receptor panel to identify and characterize test compounds as melanocortin receptor agonists and/or antagonists. In this embodiment, the method provided by the invention identifies a melanocortin receptor agonist, and comprises the steps of contacting each of the cells of the panel with a test compound to be characterized as an agonist of a mammalian melanocortin receptor and detecting binding of the test compound to each of the mammalian melanocortin receptors by assaying for a metabolite produced in the cells that bind the compound. In a preferred embodiment, the detected metabolite is cAMP.

In a preferred embodiment of this method, each of the cells of the panel of mammalian cells expressing mammalian melanocortin receptors further comprises a recombinant expression construct encoding a cyclic AMP responsive element (CRE) transcription factor binding site that is operatively linked to a nucleic acid sequence encoding a protein capable of producing a detectable metabolite. In preferred embodiments, said protein is β-galactosidase, most preferably encoded by a nucleic acid comprising the recombinant expression construct identified as pCRE/β-galactosidase (as disclosed in Chen et al., 1994, Analyt. Biochem. 226: 349–354). As provided by the invention, expression of the protein that produces the detectable metabolite is dependent on binding of the test compound to the melanocortin receptor expressed by each cell in the panel and the intracellular production of cAMP as a result. In this embodiment, cAMP production results in expression of a protein capable of producing a detectable metabolite, the protein most preferably being β-galactosidase. In preferred embodiments, the detectable metabolite absorbs light to produce a colored product. Thus, this embodiment of the invention provides a panel of melanocortin receptor-expressing cells whereby melanocortin hormone binding results in the production of a colored product in proportion to the extent of cAMP production in the cell as a result of hormone receptor binding.

In another embodiment of this aspect of the invention is provided a method for characterizing a compound as an antagonist of a mammalian melanocortin receptor. In this embodiment, the method comprises the steps of contacting each of the cells of the panel with an agonist of the mammalian melanocortin receptor in an amount sufficient to produce a detectable amount of a metabolite produced in the cells that bind the agonist, in the presence or absence of a test compound to be characterized as an antagonist of a mammalian melanocortin receptor, and detecting the amount of the metabolite produced in each cell in the panel in the presence of the test compound with the amount of the metabolite produced in each cell in the panel in the absence of the test compound. As provided by the assay, inhibition of the production of the detectable metabolite is used as an indication that the tested compound is a melanocortin receptor antagonist, which is further characterized quantitatively by the extent of said inhibition.

In a preferred embodiment of this method, each of the cells of the panel of mammalian cells expressing mammalian melanocortin receptors further comprises a recombinant expression construct encoding a cyclic AMP responsive element (CRE) transcription factor binding site that is operatively linked to a nucleic acid sequence encoding a protein capable of producing a detectable metabolite. In preferred embodiments, said protein is β-galactosidase, most preferably encoded by a nucleic acid comprising the recombinant expression construct identified as pCRE/β-galactosidase. As provided by the invention, expression of the protein that produces the detectable metabolite is dependent on binding of the test compound to the melanocortin receptor expressed by each cell in the panel. In preferred embodiments, the detectable metabolite absorbs light to produce a colored product. Thus, this embodiment of the invention provides a panel of melanocortin receptor-expressing cells whereby melanocortin hormone binding results in the production of a colored product in proportion to the extent of cAMP production in the cell as a result of hormone receptor binding.

The invention also provides melanocortin receptor agonists identified by the methods and using the screening panel of the invention. In preferred embodiments, the agonist is an agonist of the MC-3 mammalian melanocortin receptor. In preferred embodiments, the agonist is an agonist of the MC-4 mammalian melanocortin receptor.

The invention provides melanocortin receptor antagonists identified by the methods and using the screening panel of the invention. In preferred embodiments, the antagonist is an antagonist of the MC-3 mammalian melanocortin receptor. In preferred embodiments, the antagonist is an antagonist of the MC-4 mammalian melanocortin receptor.

The invention also provides methods for characterizing mammalian melanocortin receptor agonists for the capacity to modify or influence metabolism and feeding behavior in an animal. In a first aspect, the invention provides a method for characterizing melanocortin receptor MC-3 or MC-4 agonists as inhibitors of feeding behavior in an animal, the method comprising the steps of providing food to an animal that has been deprived of food for at least 12 hours, with or without administering to the animal an MC-3 or MC-4 receptor agonist of the invention, and comparing the amount of food eaten by the animal after administration of the MC-3 or MC-4 receptor agonist with the amount of food eaten by the animal without administration of the MC-3 or MC-4 receptor agonist.

In another aspect, the invention provides a method for characterizing a melanocortin MC-3 or MC-4 receptor antagonist as a stimulator of feeding behavior in an animal. In this embodiment, the method comprises the steps of providing food to an animal not deprived of food for at least 12 hours, with or without administering to the animal an MC-3 or MC-4 receptor antagonist, immediately prior to the onset of darkness or nighttime, and comparing the amount of food eaten by the animal after administration of the MC-3 or MC-4 receptor antagonist with the amount of food eaten by the animal without administration of the MC-3 or MC-4 receptor antagonist.

Thus, the invention also provides methods for using certain of the melanocortin receptor agonists and antagonists for modifying feeding behavior in an animal. In a first aspect, the invention provides a method for stimulating feeding in an animal, the method comprising administering to the animal an MC-3 or MC-4 receptor antagonist. In a preferred embodiment, the antagonists are administered systemically. In additional embodiments, the antagonists are administered intracerebroventricularly.

In another aspect, the invention provides a method for inhibiting feeding in an animal, the method comprising administering to the animal an MC-3 or MC-4 receptor agonist. In a preferred embodiment, the agonists are administered systemically. In additional embodiments, the agonists are administered intracerebroventricularly.

In yet another aspect, the invention provides mammalian melanocortin receptor agonists having the general formula:

A-B-C-D-E-F-G-amide wherein A is an aliphatic amino acid residue, including for example Leu, Ile, Nle and Met, as well as analogues and substituted derivatives thereof; B is an acidic amino acid residue, including for example Asp and Glu; C is a basic amino acid residue, such as His; D is an aromatic amino acid residue having a D- conformation, including D-Phe, D-Tyr and substituted derivatives thereof; E is a basic amino acid residue, for example Arg, Lys, homoArg, homoLys, and analogues or substituted derivatives thereof; F is Trp or substituted derivatives thereof; and G is Lys, homoLys or a substituted derivative thereof. In the peptide embodiments of the melanocortin receptor agonists of the invention, the peptide is cyclized by the formation of an amide bond between the side chain carboxyl group of the Asp or Glu residue at position B in the peptide, and the side chain amino group of the Lys or homoLys residue at position G. In preferred embodiments, the melanocortin receptor agonists of the invention are agonists of the MC-3 or MC-4 receptor.

The invention also provides mammalian melanocortin receptor antagonists having the general formula:

A-B-C-D-E-F-G-amide wherein A is an aliphatic amino acid residue, including for example Leu, Ile, Nle and Met, as well as analogues and substituted derivatives thereof; B is an acidic amino acid residue, including for example Asp and Glu; C is a basic amino acid residue, such as His; D is an aromatic amino acid residue having a D- conformation, including D-Nal and substituted derivatives thereof; E is a basic amino acid residue, for example Arg, Lys, homoArg, homoLys, and analogues or substituted derivatives thereof; F is Trp or substituted derivatives thereof; and G is Lys, homoLys or a substituted derivative thereof. In the peptide embodiments of the melanocortin receptor antagonists of the invention, the peptide is cyclized by the formation of an amide bond between the side chain carboxyl group of the Asp or Glu residue at position B in the peptide, and the side chain amino group of the Lys or homoLys residue at position G. In preferred embodiments, the melanocortin receptor antagonists of the invention are agonists of the MC-3 or MC-4 receptor.

It is an advantage of the present invention that it provides an in vitro screening method for characterizing compounds having melanocortin receptor binding activities that relate to feeding behavior in animals. Specifically, the invention advantageously provides means and methods for identifying compounds having melanocortin receptor agonist and/or antagonist activity that have been associated with either stimulating or inhibiting feeding behavior when administered to an animal. The invention thus provides an economical first step in screening compounds for the capacity to affect feeding behavior, including synthetic, peptidomimetic or organomimetic derivatives of melanocortin receptor agonists or antagonists as disclosed herein or elsewhere.

Specific preferred embodiments of the present invention will become evident from the following more detailed description of certain preferred embodiments and the claims.

DESCRIPTION OF THE DRAWINGS

FIGS. 1A and 1B illustrate the nucleotide (SEQ ID No.: 3) and amino acid (SEQ ID No.: 4) sequence of the mouse melanocyte stimulating hormone receptor gene.

FIGS. 2A and 2B illustrate the nucleotide (SEQ ID No.: 5) and amino acid (SEQ ID No.: 6) sequence of the human melanocyte stimulating hormone receptor gene.

FIGS. 3A and 3B illustrate the nucleotide (SEQ ID No.: 7) and amino acid (SEQ ID No.: 8) sequence of the human adrenocorticotropic hormone receptor gene.

FIGS. 4A and 4B illustrate the nucleotide (SEQ ID No.: 9) and amino acid (SEQ ID No.: 10) sequence of the bovine adrenocorticotropic hormone receptor gene.

FIGS. 5A and 5B illustrate the nucleotide (SEQ ID No:11) and amino acid (SEQ ID No.:12) sequences of the rat melanocortin-3 receptor.

FIGS. 6A and 6B illustrate the nucleotide (SEQ ID No.: 15) and amino acid (SEQ ID No.: 16) sequence of the human melanocortin 4 receptor gene.

FIGS. 7A and 7B illustrate the nucleotide (SEQ ID No: 17) and amino acid (SEQ ID No.: 18) sequences of the rat melanocortin-5 receptor gene.

FIGS. 20A through 20C show the effect on food intake of intracerebroventricular administration of melanocortin analogue MTII in mice.

DETAILED DESCRIPTION OF THE PREFERRED EMBODIMENTS

Figure 8:
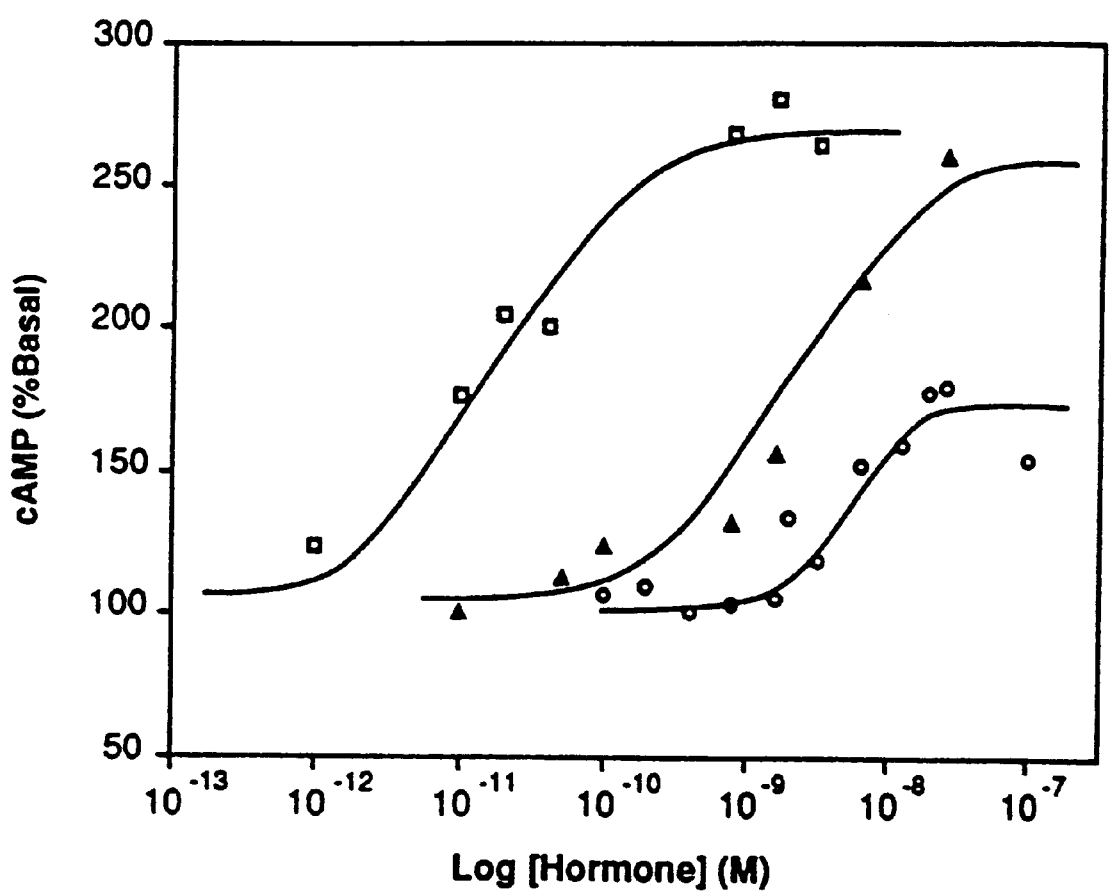
FIG. 8 shows a graph of intracellular cAMP accumulation resulting from melanocyte stimulating hormone receptor agonist binding in human 293 cells transfected with a MSH receptor-encoding recombinant expression construct.

The term "melanocortin receptor" as used herein refers to proteins having the biological activity of any of the disclosed melanocortin receptors, including the MC-1 (SEQ ID Nos.: 3, 4, 5 and 6), MC-2 (ACTH; SEQ ID Nos.: 7, 8, 9 and 10), MC-3 (SEQ ID Nos.: 11 and 12), MC-4 (SEQ ID Nos.: 15 and 16) or MC-5 (SEQ ID Nos.: 17 and 18) receptors, as well as naturally-occurring and genetically-engineered allelic variations in these sequences.

Cloned nucleic acid provided by the present invention may encode MC receptor protein of any species of origin, including, for example, mouse, rat, rabbit, cat, and human, but preferably the nucleic acid provided by the invention encodes MC receptors of mammalian, most preferably rodent and human, origin.

The production of proteins such as the MC receptors from cloned genes by genetic engineering means is well known in this art. The discussion which follows is accordingly intended as an overview of this field, and is not intended to reflect the full state of the art.

DNA which encodes MC receptors may be obtained, in view of the instant disclosure, by chemical synthesis, by screening reverse transcripts of mRNA from appropriate cells or cell line cultures, by screening genomic libraries from appropriate cells, or by combinations of these procedures, as illustrated below. Screening of mRNA or genomic DNA may be carried out with oligonucleotide probes generated from the MC receptor gene sequence information provided herein. Probes may be labeled with a detectable group such as a fluorescent group, a radioactive atom or a chemiluminescent group in accordance with know procedures and used in conventional hybridization assays, as described in greater detail in the Examples below. In the alternative, MC receptor gene sequences may be obtained by use of the polymerase chain reaction (PCR) procedure, with the PCR oligonucleotide primers being produced from the MC receptor gene sequences provided herein. See U.S. Pat. Nos. 4,683,195 to Mullis et al. and 4,683,202 to Mullis.

MC receptor proteins may be synthesized in host cells transformed with a recombinant expression construct comprising a nucleic acid encoding each of the receptors disclosed herein. Such a recombinant expression construct can also be comprised of a vector that is a replicable DNA construct. Vectors are used herein either to amplify DNA encoding an MC receptor and/or to express DNA which encodes an MC receptor. For the purposes of this invention, a recombinant expression construct is a replicable DNA construct in which a DNA sequence encoding an MC receptor is operably linked to suitable control sequences capable of effecting the expression of the receptor in a suitable host cell. The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation. Amplification vectors do not require expression control domains. All that is needed is the ability to replicate in a host, usually conferred by an origin of replication, and a selection gene to facilitate recognition of transformants. See, Sambrook et al., 1990, *Molecular Cloning: A Laboratory Manual* (Cold Spring Harbor Press: New York).

Also specifically provided by the invention are reporter expression constructs comprising a nucleic acid encoding a protein capable of expressing a detectable phenotype, such as the production of a detectable reporter molecule, in a cell expressing the construct. Such constructs can be used for producing recombinant mammalian cell lines in which the reporter construct is stably expressed. Most preferably, however, the reporter construct is provided and used to induce transient expression over an experimental period of from about 18 to 96 hrs in which detection of the reporter protein-produced detectable metabolite comprises an assay. Such reporter expression constructs are also provided wherein induction of expression of the reporter construct is controlled by a responsive element operatively linked to the coding sequence of the reporter protein, so that expression is induced only upon proper stimulation of the responsive element. Exemplary of such a responsive element is a cAMP responsive element (CRE), which induces expression of the reporter protein as a result of an increase in intracellular cAMP concentration. In the context of the present invention, such a stimulus is associated with melanocortin receptor binding, so that a reporter construct comprising one or more CREs is induced to express the reporter protein upon binding of a receptor agonist to a MC receptor in a recombinantly transformed mammalian cell. Production and use of such a reporter construct is illustrated below in Example 5.

Vectors useful for practicing the present invention include plasmids, viruses (including phage), retroviruses, and integratable DNA fragments (i.e., fragments integratable into the host genome by homologous recombination). The vector replicates and functions independently of the host genome, or may, in some instances, integrate into the genome itself. Suitable vectors will contain replicon and control sequences which are derived from species compatible with the intended expression host. A preferred vector is the plasmid pcDNA/neo I. Transformed host cells are cells which have been transformed or transfected with recombinant expression constructs made using recombinant DNA techniques and comprising mammalian MC receptor-encoding sequences. Preferred host cells are human 293 cells. Preferred host cells for the MC-2 (ACTH) receptor are Y1 cells (subclone OS3 or Y6). Transformed host cells are chosen that ordinarily express functional MC receptor protein introduced using the recombinant expression construct. When expressed, the mammalian MC receptor protein will typically be located in the host cell membrane. See, Sambrook et al., ibid.

Cultures of cells derived from multicellular organisms are a desirable host for recombinant MC receptor protein synthesis. In principal, any higher eukaryotic cell culture is workable, whether from vertebrate or invertebrate culture. However, mammalian cells are preferred, as illustrated in the Examples. Propagation of such cells in cell culture has become a routine procedure. See *Tissue Culture*, Academic Press, Kruse & Patterson, editors (1973). Examples of useful host cell lines are human 293 cells, VERO and HeLa cells, Chinese hamster ovary (CHO) cell lines, mouse Y1 (subclone OS3), and WI138, BHK, COS-7, CV, and MDCK cell lines. Human 293 cells are preferred.

Cells expressing mammalian MC receptor proteins made from cloned genes in accordance with the present invention may be used for screening agonist and antagonist compounds for MC receptor activity. Competitive binding assays are well known in the art and are described in the Examples below. Such assays are useful for drug screening of MC receptor agonist and antagonist compounds, as detected in receptor binding assays as described below.

One particular use of such screening assays is for developing drugs and other compounds useful in modifying or changing feeding behavior in mammals. The invention provides an assay system, comprising a panel of recombinant mammalian cells, heterologously expressing each of the MC receptors disclosed herein, wherein the panel is constructed of at least one cell line expressing an MC receptor. The invention provides such panels also comprising a detection means for detecting receptor agonist or antagonist binding, such as the reporter expression constructs described herein, using direct binding and competition binding assays as described in the Examples below. In the use of this panel, each MC receptor is assayed for agonist or antagonist patterns of binding a test compound, and a characteristic pattern of binding for all MC receptors is thereby determined for each test compound. This pattern is then compared with known MC receptor agonists and antagonists to identify new compounds having a pattern of receptor binding activity associated with a particular behavioral or physiological effect.

For example, provided herein is experimental evidence that MC-3 or MC-4 receptor antagonists are capable of stimulating feeding in sated animals, and that MC-3 or MC-4 agonists are capable of inhibiting feeding in animals otherwise stimulated to eat. The invention provides an in vitro assay to characterize MC-3 and MC-4 agonists/antagonists as a preliminary and economical step towards developing feeding behavior-modulating drugs for use in vivo.

These results on feeding behavior in vivo have been obtained with certain MC receptor binding analogues, SHU9119 and MTII. These compounds have the following chemical structure:

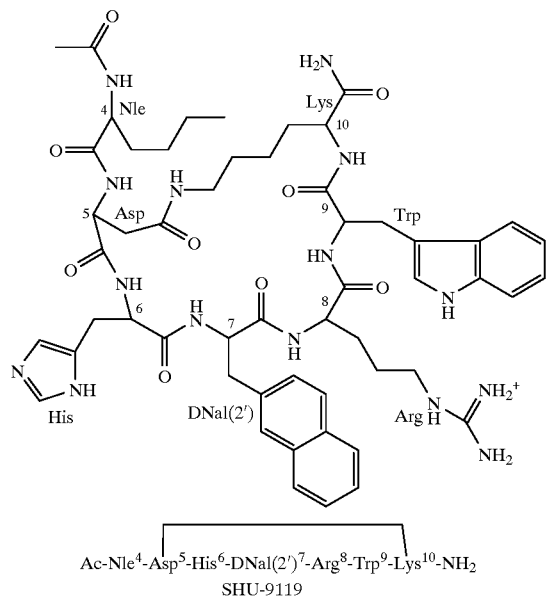

Ac-Nle$^4$-Asp$^5$-His$^6$-DNal(2')$^7$-Arg$^8$-Trp$^9$-Lys$^{10}$-NH$_2$
SHU-9119

-continued

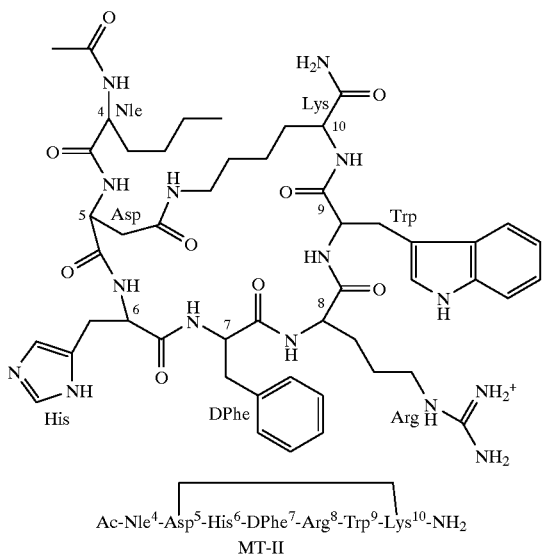

Ac-Nle[4]-Asp[5]-His[6]-DPhe[7]-Arg[8]-Trp[9]-Lys[10]-NH$_2$
MT-II (An additional analogue, SHU8914, has been tested in in vitro receptor binding assays; this compound is identical in structure to SHU9119, except that the amino acid analogue at position 7 is para-iodo-D-phenylalanine.)

Generally, those skilled in the art will recognize that peptides as described herein may be modified by a variety of chemical techniques to produce compounds having essentially the same activity as the unmodified peptide, and optionally having other desirable properties. For example, carboxylic acid groups of the peptide, whether carboxyl-terminal or sidechain, may be provided in the form of a salt of a pharmaceutically-acceptable cation or esterified to form a $C_1$–$C_{16}$ ester, or converted to an amide of formula $NR_1R_2$ wherein $R_1$ and $R_2$ are each independently H or $C_1$–$C_{16}$ alkyl, or combined to form a heterocyclic ring, such as 5- or 6-membered. Amino groups of the peptide, whether amino-terminal or sidechain, may be in the form of a pharmaceutically-acceptable acid addition salt, such as the HCl, HBr, acetic, benzoic, toluene sulfonic, maleic, tartaric and other organic salts, or may be modified to $C_1$–$C_{16}$ alkyl or dialkyl amino or further converted to an amide. Hydroxyl groups of the peptide sidechain may be converted to $C_1$–$C_{16}$ alkoxy or to a $C_1$–$C_{16}$ ester using well-recognized techniques. Phenyl and phenolic rings of the peptide sidechain may be substituted with one or more halogen atoms, such as fluorine, chlorine, bromine or iodine, or with $C_1$–$C_{16}$ alkyl, $C_1$–$C_{16}$ alkoxy, carboxylic acids and esters thereof, or amides of such carboxylic acids. Methylene groups of the peptide sidechains can be extended to homologous $C_2$–$C_4$ alkylenes. Thiols can be protected with any one of a number of well-recognized protecting groups, such as acetamide groups. Those skilled in the art will also recognize methods for introducing cyclic structures into the peptides of this invention to select and provide conformational constraints to the structure that result in enhanced binding and/or stability. For example, a carboxyl-terminal or amino-terminal cysteine residue can be added to the peptide, so that when oxidized the peptide will contain a disulfide bond, thereby generating a cyclic peptide. Other peptide cyclizing methods include the formation of thioethers and carboxyl- and amino-terminal amides and esters.

Peptidomimetic and organomimetic embodiments are also hereby explicitly declared to be within the scope of the present invention, whereby the three-dimensional arrangement of the chemical constituents of such peptido- and organomimetics mimic the three-dimensional arrangement of the peptide backbone and component amino acid sidechains in the peptide, resulting in such peptido- and organomimetics of the peptides of this invention having substantial biological activity. It is implied that a pharmacophore exists for the receptor agonist and antagonist properties of these and related MC receptor binding analogues. A pharmacophore is an idealized, three-dimensional definition of the structural requirements for biological activity. Peptido- and organomimetics can be designed to fit each pharmacophore with current computer modeling software (computer aided drug design). MC receptor binding analogues derived using such software and comprising peptido- and organomimetics of SHU9119 and MTII and related analogues are within the scope of the claimed invention.

The MC receptor binding analogues, in particular those analogues that are MC-3 or MC-4 receptor agonists or antagonists are provided to be used in methods of influencing, modifying or changing feeding behavior in mammals in vivo. Specific examples of uses for the MC receptor binding analogues of the invention include but are not limited to treatment of eating disorders such as anorexia and obesity, and other pathological weight and eating-related disorders. Other examples are failure to thrive disorders and disease-related cachexia, such as occurs in cancer patients. Also within the scope of the analogues of the invention is use for enhancing appearance, athletic ability, or adjuvant to other therapies to treat disorders such as high blood pressure, high serum cholesterol, vascular and heart disease, stroke, kidney disease, diabetes and other metabolic disorders.

The Examples which follow are illustrative of specific embodiments of the invention, and various uses thereof. They set forth for explanatory purposes only, and are not to be taken as limiting the invention.

EXAMPLE 1

Isolation of an αMSH Receptor Probe by Random PCR Amplification of Human Melanoma cDNA Using Degenerate Oligonucleotide Primers In order to clone novel G-protein coupled receptors, cDNA prepared from RNA from human melanoma cells was used as template for a polymerase chain reaction (PCR)-based random cloning experiment. PCR was performed using a pair of degenerate oligonucleotide primers corresponding to the putative third and sixth transmembrane regions of G-protein coupled receptors (Libert et al., 1989, Science 244: 569–72; Zhou et al., 1990, Nature 347: 76–80). The PCR products obtained in this experiment were characterized by nucleotide sequencing. Two novel sequences representing novel G-protein-coupled receptors were identified.

PCR amplification was performed as follows. Total RNA was isolated from a human melanoma tumor sample by the guanidinium thiocyanate method (Chirgwin et al., 1979, Biochemistry 18: 5294–5299). Double-stranded cDNA was synthesized from total RNA with murine reverse transcriptase (BRL, Gaithersburg, Md.) by oligo-dT priming (Sambrook et al., ibid.). The melanoma cDNA mixture was then subjected to 45 cycles of PCR amplification using 500 picomoles of degenerate oligonucleotide primers having the following sequence:

Primer III (sense):
GAGTCGACCTGTG(C/T)G(C/T)(C/G)AT(C/T)(A/G)CIIT(G/T)GAC(C/A)G(C/G)TAC    (SEQ ID NO:1)

and

Primer VI (antisense):
CAGAATTCAG(T/A)AGGGCAICCAGCAGAI(G/C)(G/A)(T/C)GAA                       (SEQ ID NO:2)

in 100 μl of a solution containing 50 mM Tris-HCl (pH 8.3), 2.5 mM MgCl$_2$, 0.01% gelatin, 200 μM each dNTP, and 2.5 units of Taq polymerase (Saiki et al., 1988, *Science* 239: 487–491). These primers were commercially synthesized by Research Genetics Inc. (Huntsville, Ala.). Each PCR amplification cycle consisted of incubations at 94° C. for 1 min (denaturation), 45° C. for 2 min (annealing), and 72° C. for 2 min (extension).

Amplified products of the PCR reaction were extracted with phenol/chloroform and precipitated with ethanol. After digestion with EcoRl and SalI, the PCR products were separated on a 1.2% agarose gel. A slice of this gel, corresponding to PCR products of 300 basepairs (bp) in size, was cut out and purified using glass beads and sodium iodide, and the insert was then cloned into a pBKS cloning vector (Stratagene, LaJolla, Calif.).

A total of 172 of such pBKS clones containing inserts were sequenced using Sequenase (U.S. Biochemical Corp., Cleveland, Ohio) by the dideoxynucleotide chain termination method (Sanger et al., 1977, *Proc. Natl. Acad. Sci. USA* 74: 5463–5467). Two types of sequences homologous to other G-protein coupled receptors were identified.

EXAMPLE 2A

Isolation of a Mouse αMSH (MC-1) Receptor cDNA

Probes isolated in Example 1 were used to screen a Cloudman melanoma cDNA library in order to isolate a full-length cDNA corresponding to the cloned probe. One clone was isolated from a library of 5×10$^6$ clones screened as described in co-owned U.S. Pat. No. 5,532,347, incorporated by reference. This clone contained an insert of 2.6 kilobases (kb). The nucleotide sequence of the complete coding region was determined (see co-owned U.S. Pat. No. 5,532,347, incorporated by reference); a portion of this cDNA comprising the coding region was sequenced and is shown in FIGS. 1A and 1B (SEQ ID Nos: 3 & 4).

EXAMPLE 2B

Isolation of a Human αMSH (MC-1) Receptor cDNA

In order to isolate a human counterpart of the murine melanocyte αMSH receptor gene disclosed in Example 2A and co-owned U.S. Pat. No. 5,532,347, a human genomic library was screened at high stringency (50% formamide, 42° C.) using the human PCR fragments isolated as described in Example 1. A genomic clone was determined to encode an human MSH receptor (SEQ ID NO:5.; FIGS. 2A and 2B). The human MSH receptor has a predicted amino acid sequence (SEQ ID NO:6) that is 75% identical and colinear with the mouse αMSH receptor cDNA sequence. The predicted molecular weight of the human MSH receptor is 34.7 kD.

EXAMPLE 2C

Isolation of a Human ACTH (MC-2) Receptor cDNA

For cloning the ACTH receptor (MC-2), a human genomic library was screened at high stringency (50% formamide, 1M NaCl, 50 nM Tris-HCl, pH 7.5, 0.1% sodium pyrophosphate, 0.2% sodium dodecyl sulfate, 100 μg/ml salmon sperm DNA, 10 ×Denhardt's solution, 42° C.), using the human PCR fragments isolated as described in Example 1 herein and U.S. Pat. No. 5,280,112, incorporated by reference. A genomic clone was isolated that encodes a highly related G-coupled receptor protein (SEQ ID No:7 and FIGS. 3A and 3B). The predicted amino acid sequence (SEQ ID NO:8) of this clone is 39% identical and also colinear, excluding the third intracellular loop and carboxy-terminal tail, with the human MSH receptor gene product. The predicted molecular weight of this putative ACTH receptor is 33.9 kilodaltons (kD). This clone was identified as encoding an MC-2 receptor based on its high degree of homology to the murine and human MSH receptors, and the pattern of expression in different tissue types, as described in Example 3 in U.S. Pat. No. 5,280,112, incorporated by reference herein.

EXAMPLE 2D

Isolation of a Bovine ACTH (MC-2) Receptor cDNA

A bovine genomic DNA clone encoding the bovine counterpart of the MC-2 (ACTH) receptor was isolated from a bovine genomic library, essentially as described in Example 2C above, and its nucleotide sequence determined (as shown in FIGS. 4A and 4B; SEQ ID Nos:9 & 10).

EXAMPLE 2E

Isolation of a Rat γ-MSH (MC-3) Receptor cDNA

The mouse αMSH receptor cDNA isolated as described in Example 2A and co-owned U.S. Pat. No. 5,532,347 was used to screen a rat hypothalamus cDNA library at low stringency (30% formamide, 5×SSC, 0.1% sodium pyrophosphate, 0.2% sodium dodecyl sulfate, 100 μg/ml salmon sperm DNA, and 10% Denhardt's solution) at 42° C. for 18 h. A 1 kb cDNA clone was isolated and sequenced as described in co-owned U.S. Pat. No. 5,532,347, and this clone used to re-screen the rat hypothalamus cDNA library at high stringency (same conditions as above except that formamide was present at 45%). A cDNA clone approximately 2.0 kb in length was isolated and analyzed as described in co-pending U.S. application Ser. No. 08/044, 812, incorporated by reference; a portion of this cDNA comprising the coding region was sequenced and is shown in FIGS. 5A and 5B (SEQ ID Nos:11 & 12).

EXAMPLE 2F

Isolation of a Human MC-4 Receptor DNA

For cloning the MC-4 receptor, a human genomic library was screened at moderate stringency (40% formamide, 1M NaCl, 50 mM Tris-HCl, pH 7.5, 0.1% sodium pyrophosphate, 0.2% sodium dodecyl sulfate, 100 μg/ml salmon sperm DNA, 10 ×Denhardt's solution, 42° C.), using rat PCR fragments isolated as described in Example 1 herein, with the exception that the following primers were used for PCR:

```
Primer II (sense):
GAGTCGACC(A/G)CCCATGTA(C/T)T(AGT)(C/T)TTCATCTG   (SEQ ID NO:13)

and

Primer VII (antisense):
CAGAATTCGGAA(A/G)GC(A/G)TA(G/T)ATGA(A/G)GGGGTC   (SEQ ID NO:14)
```

A genomic clone was isolated that encodes a highly related G-coupled receptor protein (SEQ ID NO:15 and FIGS. 6A and 6B) on a 1.9 kb HindIII fragment. The predicted amino acid sequence (SEQ ID NO:16) of this clone shares 55–61% sequence identity with human MC-3 and MC-5 receptors, and 46–47% sequence identity with the human MC-1 and MC-2 (ACTH) receptor.

EXAMPLE 2G

Isolation of a Mouse MC-5 Receptor DNA

One million clones from a mouse 129SVJ genomic library comprising 5,000,000 clones in the λFixII vector (Stratagene) were screened at low stringency (hybridization in 40% formamide at 42° C., washing performed in 0.5×SSC at 60° C., as described above in Example 2E) using radiolabeled probes from the rat MC-3 and MC-4 receptors, as described in Examples 2E and 2F. Positively-hybridizing clones were isolated and sequenced, and the sequences obtained were compared to previously-isolated melanocortin receptor clones. One clone, comprising a previously-unknown sequence, was determined to encode the MC-5 melanocortin receptor. The nucleotide and amino acid sequences of this receptor are shown in FIGS. 7A and 7B (SEQ ID No.: 17 & 18).

EXAMPLE 3

Construction of a Recombinant Expression Construct, DNA Transfection and Functional Expression of the MCR Gene Products In order to produce recombinant mammalian cells expressing each of the melanocortin receptors of Example 2, cDNA or the coding exons from genomic DNA from each receptor was cloned into a mammalian expression construct, the resulting recombinant expression construct transfected into human 293 cells, and cell lines generated that expressed the melanocortin receptor proteins in cellular membranes at the cell surface.

The mouse αMSH receptor was cloned by excising the entire coding region of the αMSH$^R$ (MC-1) cDNA insert comprising a 2.1 kb fragment and subcloning this fragment into the BamHI/XhoI sites of pcDNAI/neo expression vector (Invitrogen, San Diego, Calif.). The resulting plasmid was prepared in large-scale through one cycle of CsCl gradient ultracentrifugation, and 20 μg of the plasmid transfected into each 100 mm dish of 293 cells using the calcium phosphate method (see Chen & Okayama, 1987, *Mol. Cell. Biol.* 7: 2745–2752). After transfection, cells were cultured in DMEM media supplemented with 10% calf serum in a 3% $CO_2$ atmosphere at 37° C. Selection was performed with neomycin (G418; GIBCO) at a concentration of 1000 μg/mL; selection was started 72 hr after transfection and continued for 3 weeks.

The αMSH receptor is known to couple to G-proteins and thereby activate adenyl cyclase, increasing intracellular levels of cAMP (see Buckley & Ramachandran, 1981, *Proc. Natl. Acad. Sci. USA* 78: 7431–7435; Grahame-Smith et al., 1967, *J. Biol. Chem* 242: 5535–5541; Mertz & Catt, 1991, *Proc. Natl. Acad. Sci. USA* 88: 8525–8529; Pawalek et al., 1976, *Invest. Dermatol.* 66: 200–209). This property of cells expressing the αMSH receptor was used analyze expression of the αMSH receptor in cell colonies transfected with the expression vectors described herein as follows. Cells (~1× $10^6$) were plated in 6-well dishes, washed once with DMEM containing 1% bovine serum albumin (BSA) and 0.5 mM IBMX (a phosphodiesterase inhibitor), then incubated for 45 minutes at 37° C. with varying concentrations of the melanotropic peptides αMSH, βMSH, γMSH, the MSH peptide analogues Nle$^4$, D-Phe$^7$-αMSH (NDP-MSH), and ACTH. Following hormone treatment, the cells were washed twice with phosphate buffered saline and intracellular cAMP extracted by lysing the cells with 1 mL of 60% ethanol. Intracellular cAMP concentrations were determined using an assay (Amersham) which measures the ability of cAMP to displace (8-$^3$H) cAMP from a high affinity cAMP binding protein (see Gilman, 1970, *Proc. Natl. Acad. Sci. USA* 67: 305–312).

The results of these experiments are shown in FIG. 8. The abscissa indicates the concentration of each hormone and the ordinate indicates the percentage of basal intracellular cAMP concentration achieved by each treatment. Points indicate the mean of duplicate incubations; the standard error did not exceed 15% for any data point. None of the peptides tested induced any change in intracellular cAMP in cells containing the vector alone. Cells expressing the murine αMSH receptor responded to melanotropic peptides with a 2–3 fold elevation of intracellular cAMP, similar to levels of cAMP induced by these peptides in the Cloudman cell line (see Pawalek, 1985, *Yale J. Biol. Med.* 58: 571–578). The $EC_{50}$ values determined for αMSH ($2.0 \times 10^{-9}$M), ACTH ($8.0 \times 10^{-9}$M) and the superpotent MSH analogue NDP-MSH ($2.8 \times 10^{-11}$M) correspond closely to reported values (see Tatro et al., 1990, *Cancer Res.* 50: 1237–1242). As expected, the βMSH peptide had an $EC_{50}$ value comparable to αMSH, while γMSH had little or no activity (see Slominski et al., 1992, *Life Sci.* 50: 1103–1108), confirming the identity of this receptor as a melanocyte αMSH receptor.

Figure 9:
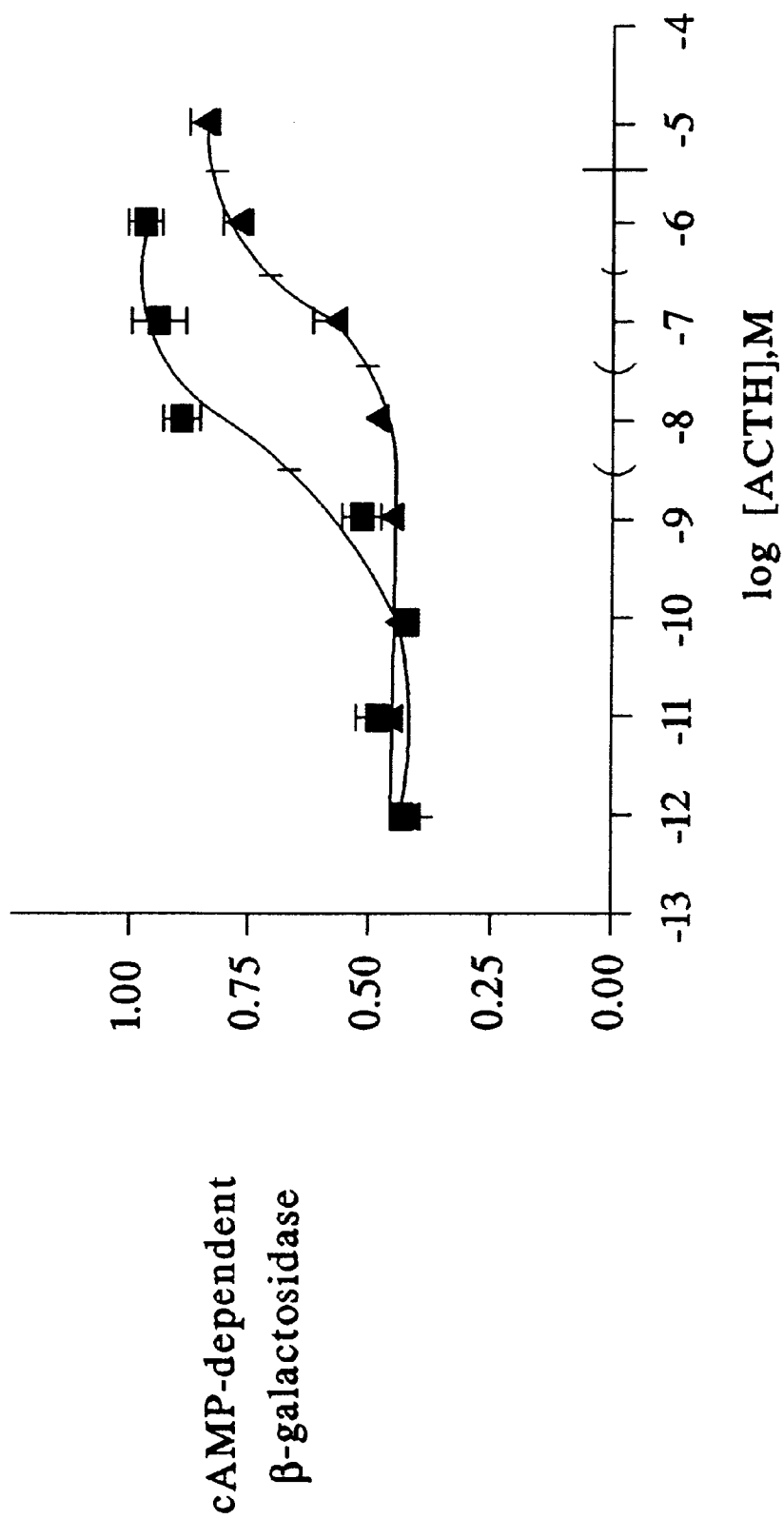
FIG. 9 illustrates the cAMP response of mouse Y1 cells to binding of melanocortin peptides to human melanocortin-2 (ACTH) receptor, as measured using the β-galactosidase assay described in Example 4.

A similar series of experiments were performed using mouse Y1 cells (subclone OS3; Schimmer et al., 1995, *J. Cell. Physiol.* 163: 164–171) expressing the human and bovine MC-2 (ACTH) receptor clones of Examples 2C and 2D. These results are shown in FIG. 9, where the extent of cAMP responsive element-linked β-galactosidase activity (see Example 4, below) is shown with increasing concentrations of ACTH.

The entire coding region of the MC-3 receptor cDNA insert, obtained as described above in the copending U.S. Ser. No. 08/044,812, was contained in a 2.0 kb restriction enzyme digestion fragment and was cloned into the BamHI/

XhoI sites of pcDNA/neo I expression vector (Invitrogen, San Diego, Calif.). The resulting plasmid was prepared in large-scale through one cycle of CsCl gradient ultracentrifugation and 20 μg pcDNA/MC-3 receptor DNA were transfected into each 100 mm dish of 293 cells using the calcium phosphate method (see Chen & Okayama, 1987, *Mol. Cell. Biol.* 7: 2745–2752). After transfection, cells were cultured in DMEM media supplemented with 10% calf serum in a 3% $CO_2$ atmosphere at 37° C. Selection was performed with neomycin (G418; GIBCO) at a concentration of 1000 μg/mL; selection was started 72 h after transfection and continued for 3 weeks.

Specific binding of melanocortin peptides to cells expressing the MC-3 receptor was demonstrated by competition experiments using $^{125}$I-labeled Nle$^4$-D-Phe$^7$-α-MSH (NDP-MSH, as described in Tatro et al., 1990, *Cancer Res.* 50: 1237–1242). Suspended cells (2×10$^5$) were incubated at 37° C. with 500,000 cpm of labeled peptide for 10 min in binding buffer (Ham's F10 media plus 10 mM HEPES, pH 7.2, 0.25% bovine serum albumin, 500K IU/mL aprotinin, 100 μg/mL bacitracin and 1 mM 1,10-phenanthroline) in the presence or absence of the indicated concentrations of peptides. Maximum labeling was achieved within 10 min.

Figure 10:
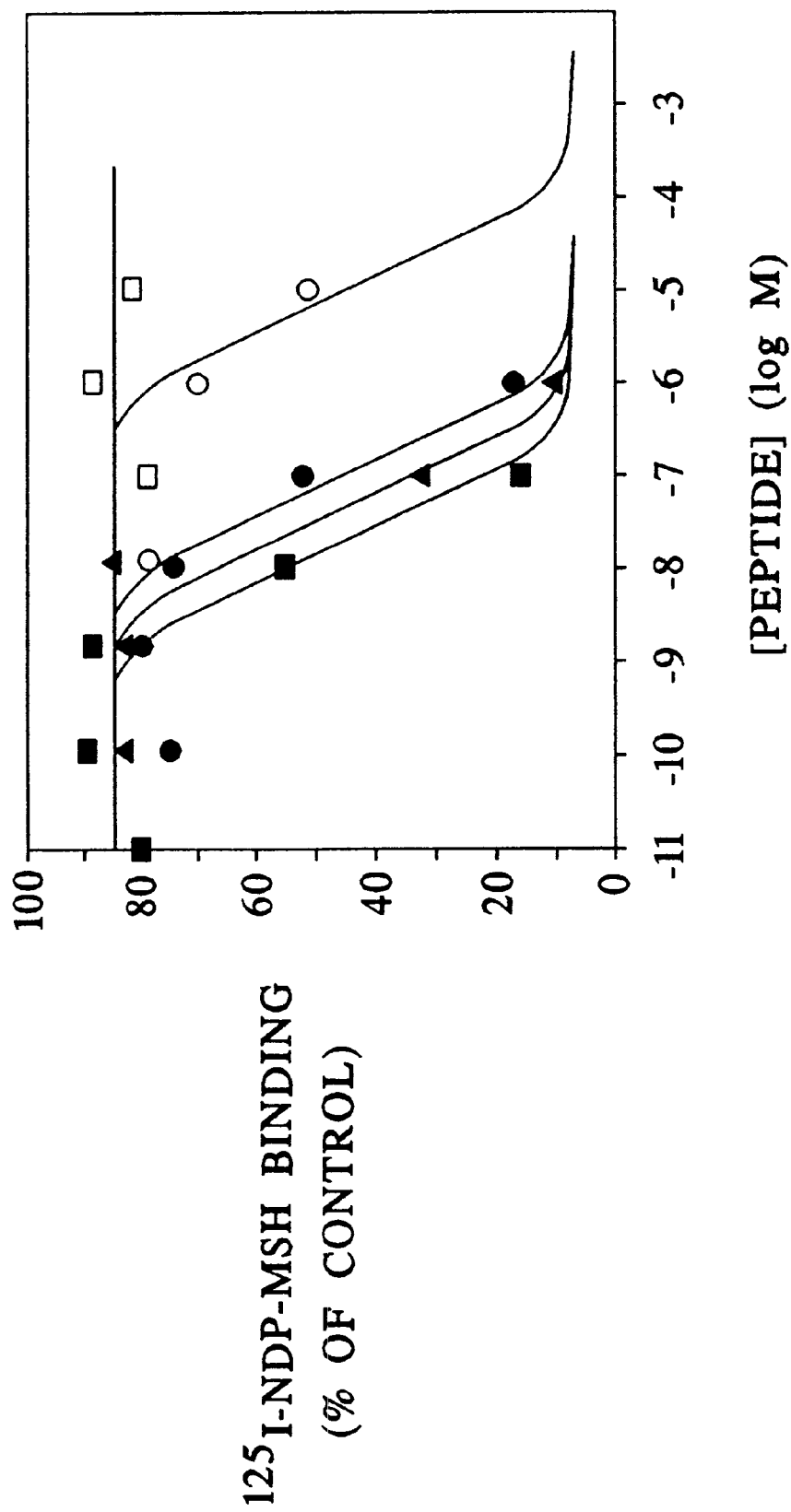
FIG. 10 illustrates the results of competition binding experiments of melanocortin peptides to cells expressing a recombinant expression construct encoding the rat melanocortin-3 receptor.

The results of these experiments are shown in FIG. 10. Labeled NDP-MSH binding to cells expressing the MC-3 receptor, produced as described above, is inhibited by competition with unlabeled peptides known to be melanocortin receptor agonists, having a relative order of potency as follows:

NDP-MSH>γ-MSH>α-MSH>ACTH$_{4-10}$>>>ORG2766.

Approximate $K_i$ values derived from this experiment are as shown in Table I:

TABLE I

| Agonist | $K_i$ (approx) |
|---|---|
| NDP-MSH | $2 \times 10^{-8}$ |
| γ-MSH | $5 \times 10^{-8}$ |
| α-MSH | $1 \times 10^{-7}$ |
| ACTH$_{4-10}$ | $8 \times 10^{-5}$ | cAMP production assays as described above were also used to analyze expression of MC-3R in cells transfected with the expression vectors described herein as follows. Cells (~5×10$^6$) were plated in 6-well dishes, washed once with DMEM containing 1% bovine serum albumin (BSA) and 0.5 mM IBMX (a phosphodiesterase inhibitor), then incubated for 1 h at 37° C. with varying concentrations of the melanotropic peptides αMSH, γ$_3$MSH, γMSH, the MSH peptide analogues Nle$^4$-D-Phe$^7$-αMSH (NDP-MSH), ACTH$_{4-10}$ and ACTH$_{1-39}$. Following hormone treatment, the cells were washed twice with phosphate buffered saline and intracellular cAMP extracted by lysing the cells with 1 mL of 60% ethanol. Intracellular cAMP concentrations were determined using an assay which measures the ability of cAMP to displace (8-$^3$H) cAMP from a high affinity cAMP binding protein (see Gilman, 1979, *Proc. Natl. Acad. Sci. USA* 67: 305–312).

Figure 11A:
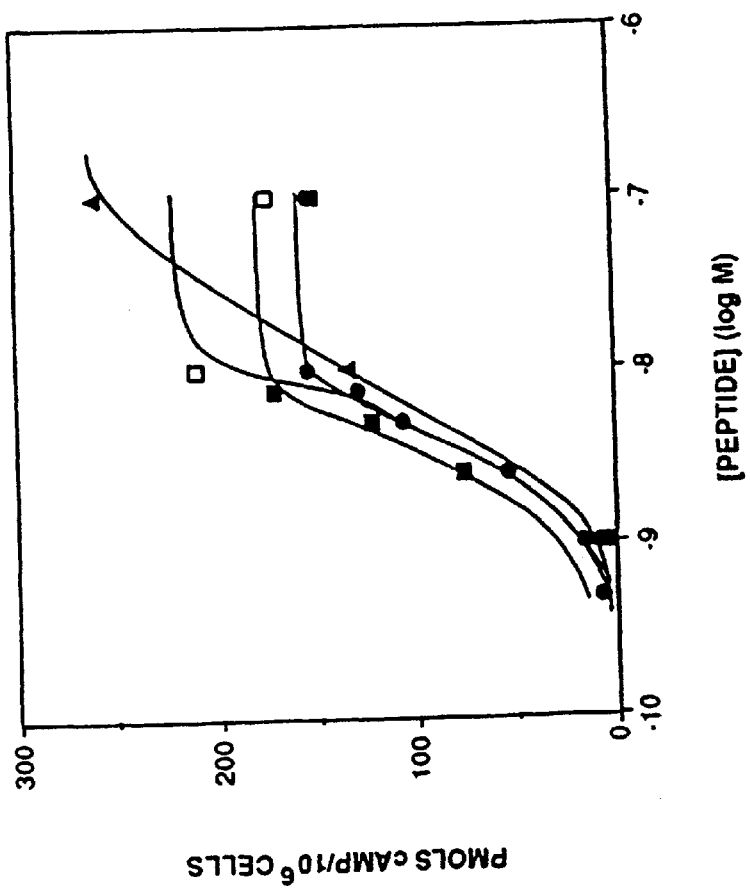
FIGS. 11A through 11C illustrate the results of experiments showing intracellular cAMP accumulation caused by receptor-ligand binding in human 293 cells expressing the MC-3 receptor.
Figure 11B:
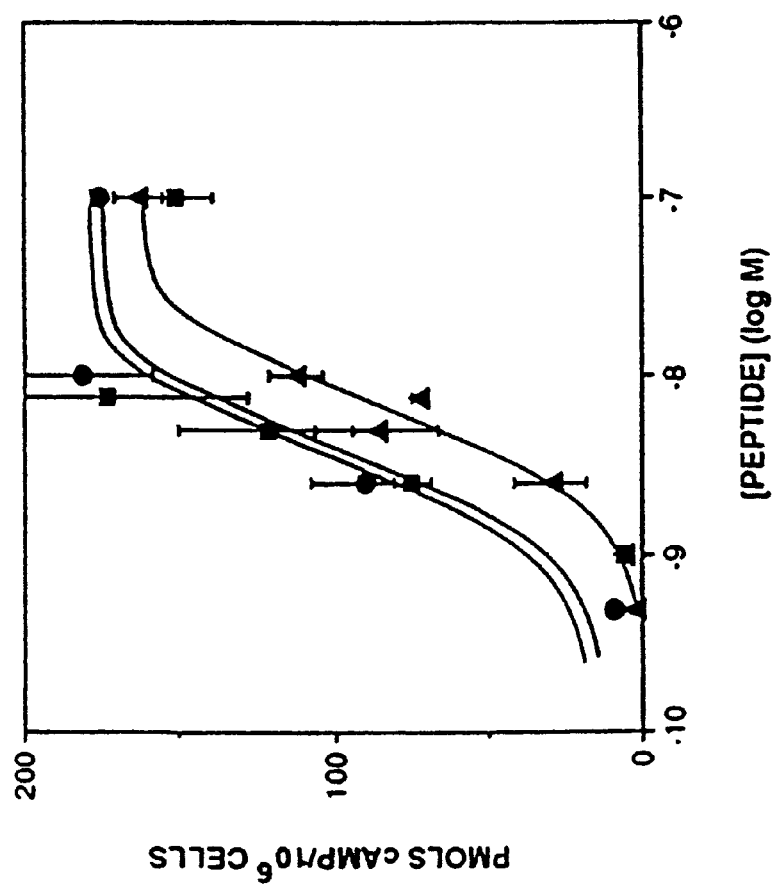
Figure 11C:
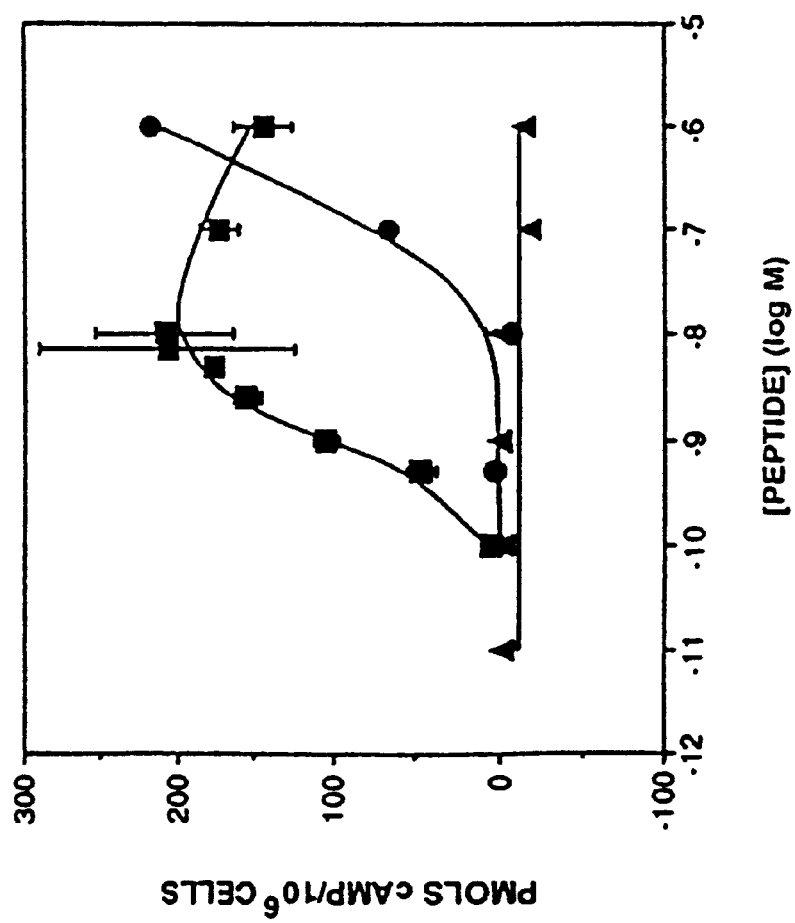

The results of these experiments are shown in FIGS. 11A through 11C. The abscissa indicates the concentration of each hormone and the ordinate indicates the percentage of basal intracellular cAMP concentration achieved by each treatment. Points indicate the mean of duplicate incubations; the standard error did not exceed 15% for any data point. FIG. 11A depicts the results of experiments using peptides found in vivo; FIG. 11B depicts results found with γ-MSH variants; and FIG. 11C shows results of synthetic melanocortin analogues. None of the peptides tested induced any change in intracellular cAMP in cells containing the vector alone. Cells expressing rat MC-3R responded strongly to every melanotropic peptide containing the MSH code sequence His-Phe-Arg-Trp, with up to a 60-fold elevation of intracellular cAMP levels. EC$_{50}$ values ranged from 1–50 nM. The most potent ligand and the one having the lowest EC$_{50}$ was found to be γMSH. The order of potency for the naturally occurring melanocortins was found to be:

γ$_2$-MSH=γMSH>αMSH=ACTH$_{1-39}$>γ$_3$-MSH>des-acetyl-αMSH>ACTH$_{4-10}$.

EC$_{50}$ values for these compounds are shown in Table II:

TABLE II

| Agonist | EC$_{50}$ |
|---|---|
| NDP-MSH | $1 \times 10^{-9}$ |
| γ$_1$-MSH | $3 \times 10^{-9}$ |
| γ$_2$-MSH | $3 \times 10^{-9}$ |
| α-MSH | $4 \times 10^{-9}$ |
| ACTH$_{1-39}$ | $4 \times 10^{-9}$ |
| γ$_3$-MSH | $6 \times 10^{-9}$ |
| desacetyl-αMSH | $8 \times 10^{-9}$ |
| ACTH$_{4-10}$ | $1 \times 10^{-7}$ |

Additionally, a synthetic melanocortin peptide (ORG2766), known to have the greatest activity in vivo in stimulation of retention of learned behavior and in stimulation of neural regeneration, was unable to stimulate MC-3R-mediated cAMP production, and was also inactive as an antagonist. The results strongly indicate that this peptide does not bind to MC-3R protein.

Figure 12:
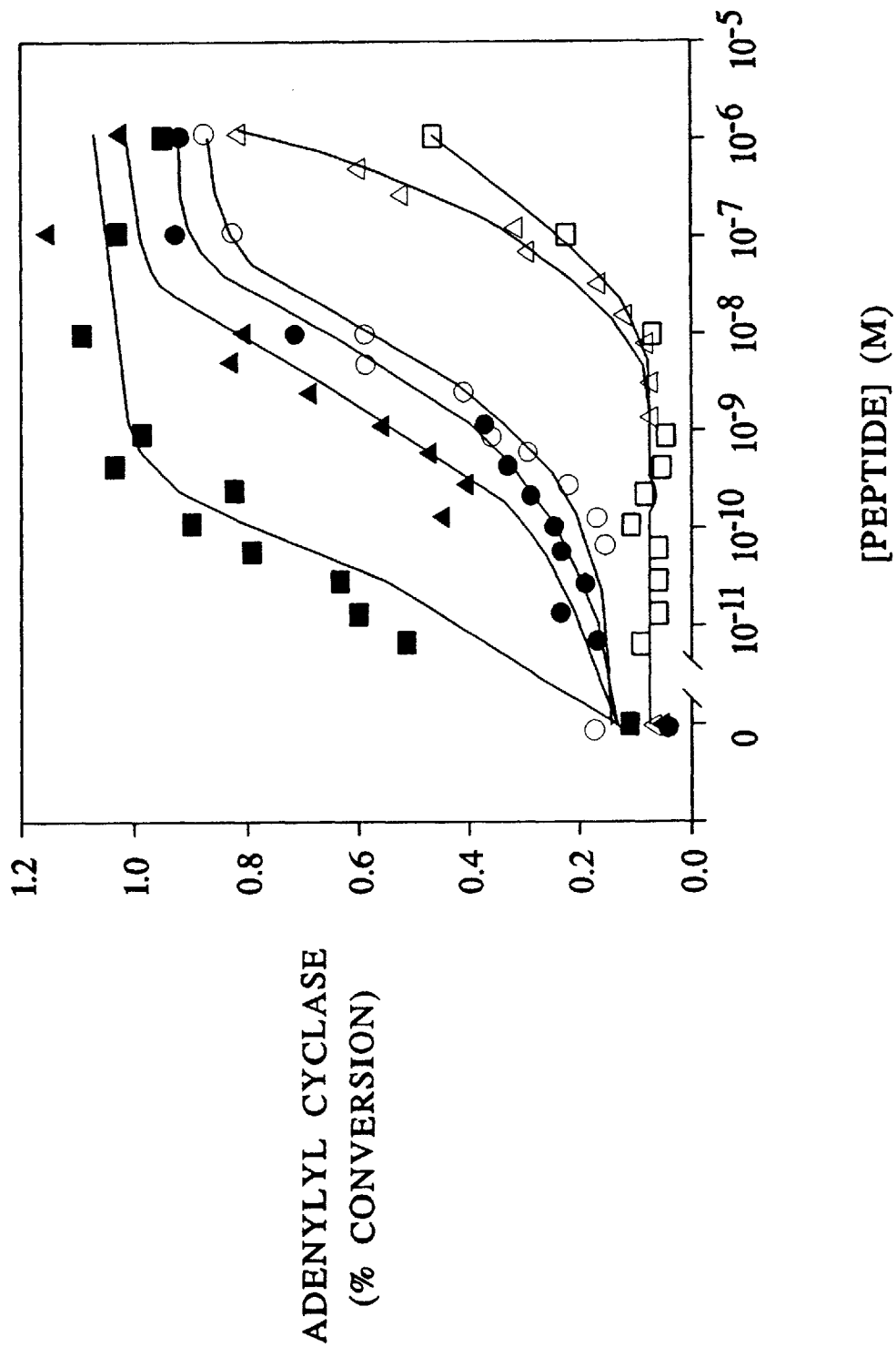
FIG. 12 shows a graph of intracellular cAMP accumulation resulting from peptides to human melanocortin-4 receptor agonist binding in human 293 cells transfected with a MC-4 receptor-encoding recombinant expression construct.

The MC-4 receptor was cloned in a 1.9 kb HindIII genomic DNA fragment after PCR amplification of a lambda phage clone into pcDNAI/Neo (Invitrogen). This plasmid was stably introduced into human 293 cells by calcium phosphate co-precipitation using standard techniques, and plasmid-containing cells selected in G418-containing media. Specificity of receptor-hormone binding was assayed using adenylate cylcase activity as described above. The MC-4 receptor was found to couple to adenylate cyclase activity having the following pattern of agonist affinity:

NDP-MSH>des-acetyl-α-MSH>/=ACTH$_{1-39}$>/=α-MSH>>γ$_2$-MSH=ACTH$_{4-10}$ whereas the synthetic ACTH$_{4-9}$ analogue ORG2766 showed no detectable binding to the MC-4 receptor. The results of adenylate cyclase activity assays are shown in FIG. 12. EC$_{50}$ values for each of the tested MC-4 receptor agonists are as shown in Table III:

TABLE III

| Agonist | EC$_{50}$ |
|---|---|
| NDP-MSH | $1.1 \times 10^{-11}$ M |
| desacetyl-αMSH | $4.9 \times 10^{-10}$ M |
| ACTH$_{1-39}$ | $6.8 \times 10^{-10}$ M |
| α-MSH | $1.5 \times 10^{-9}$ M |
| γ$_2$-MSH | $>10^{-7}$ M |
| ACTH$_{4-10}$ | $>10^{-7}$ M |

A 1.6 kb ApaI-HindIII fragment comprising the entire coding sequence of the mouse MC-5 melanocortin receptor disclosed in Example 2G above was cloned into the pcDNA/neo expression vector (Invitrogen) after PCR amplification of the lambda phage clone. This plasmid was stably introduced into human 293 cells by calcium phosphate co-precipitation using standard techniques, and plasmid-containing cells selected in G418 containing media. Specificity of receptor-hormone binding was assayed using adenylate cylcase activity as described above. The MC-5 receptor was found to couple to adenylate cyclase activity having the following pattern of agonist affinity:

α-MSH>βMSH>>γ-MSH

Figure 13:
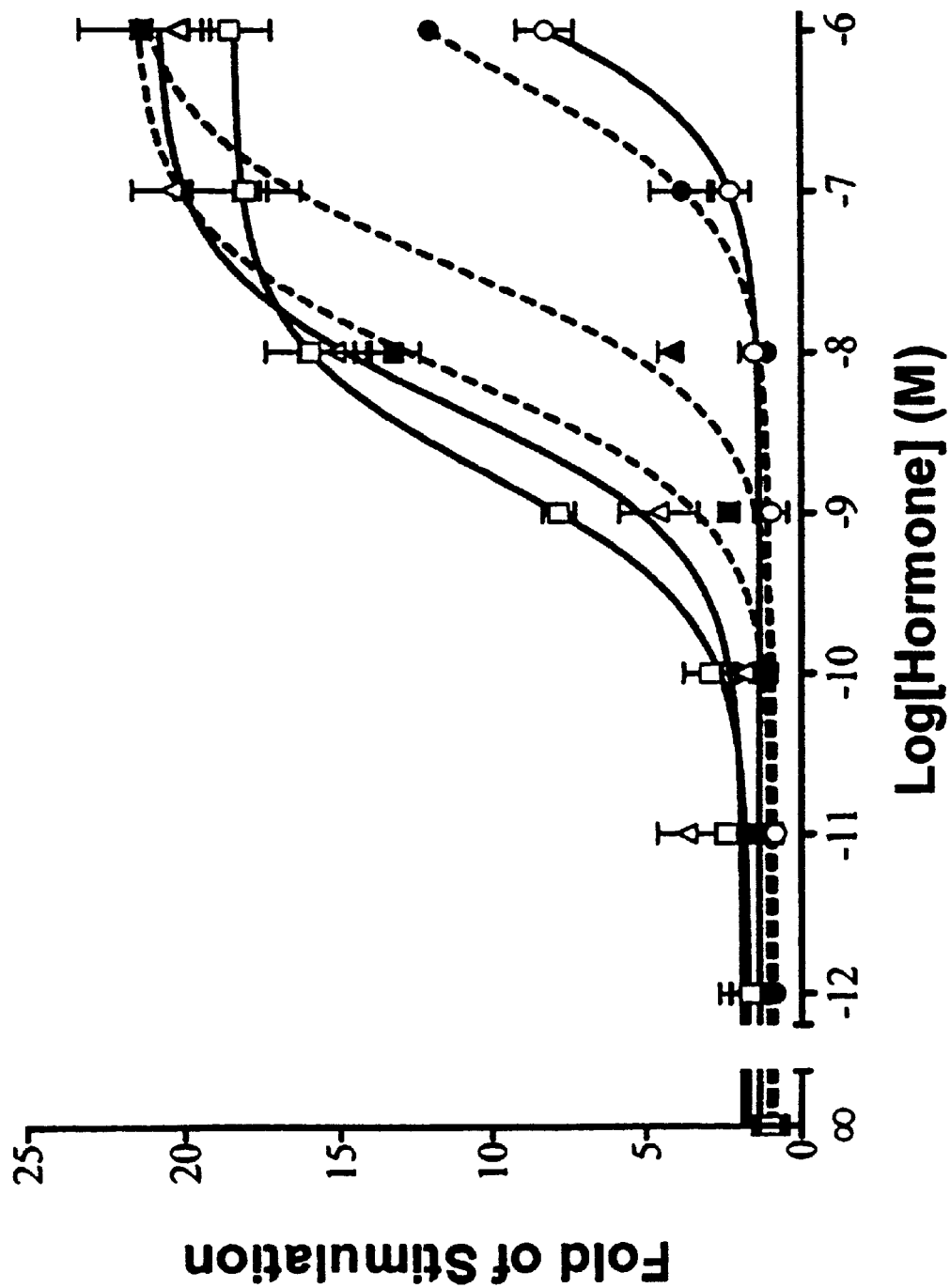
FIG. 13 illustrates the results of cAMP accumulation (AC) and cAMP-dependent β-galactosidase (β-gal) assays of melanocortin peptide binding to a rat melanocortin-5 receptor.

The results of adenylate cyclase activity assays (AC) and cAMP-dependent β-galactosidase (β-gal) assay are shown in FIG. 13. $EC_{50}$ values for each of the tested MC-5 receptor agonists are: α-MSH=$1.7 \times 10^{-9}$M; and βMSH=$5 \times 10^{-9}$M.

EXAMPLE 4

Melanocortin Analogue Binding to Mammalian Melanocortin Receptors

Recombinant cells prepared as described above in Example 3 were used to characterize receptor binding of two melanocortin analogues comprising cyclic lactam heptapeptides.

The melanocortin receptor analogue SHU9119 has the following chemical structure:

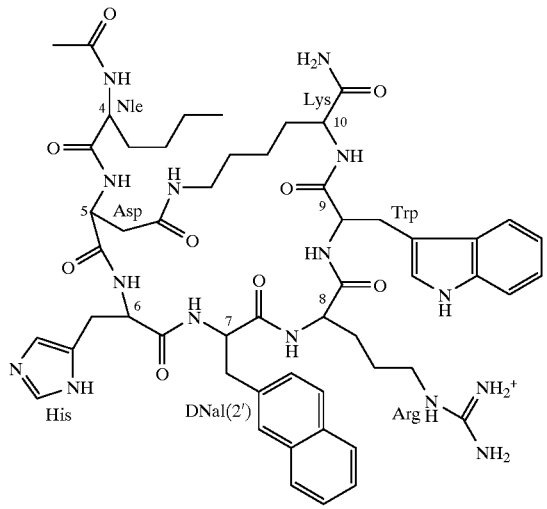

Ac-Nle$^4$-cyclo(Asp$^5$, D-Nal(2)$^7$, Lys$^{10}$)αMSH-(4-10)-amide

The melanocortin receptor analogue MTII has the following chemical structure:

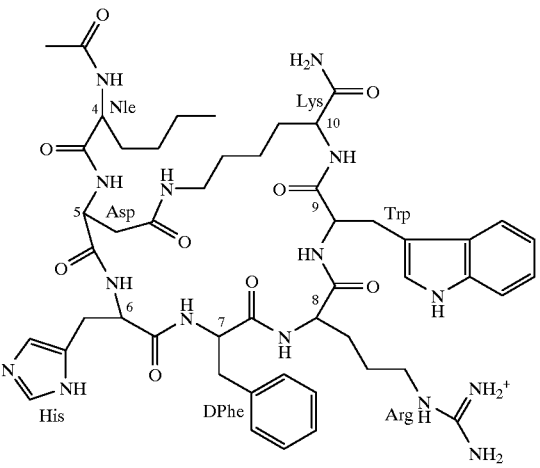

These analogues were prepared as described in Hruby et al. (1995, J. Med. Chem. 38: 3454–3461).

Figure 14:
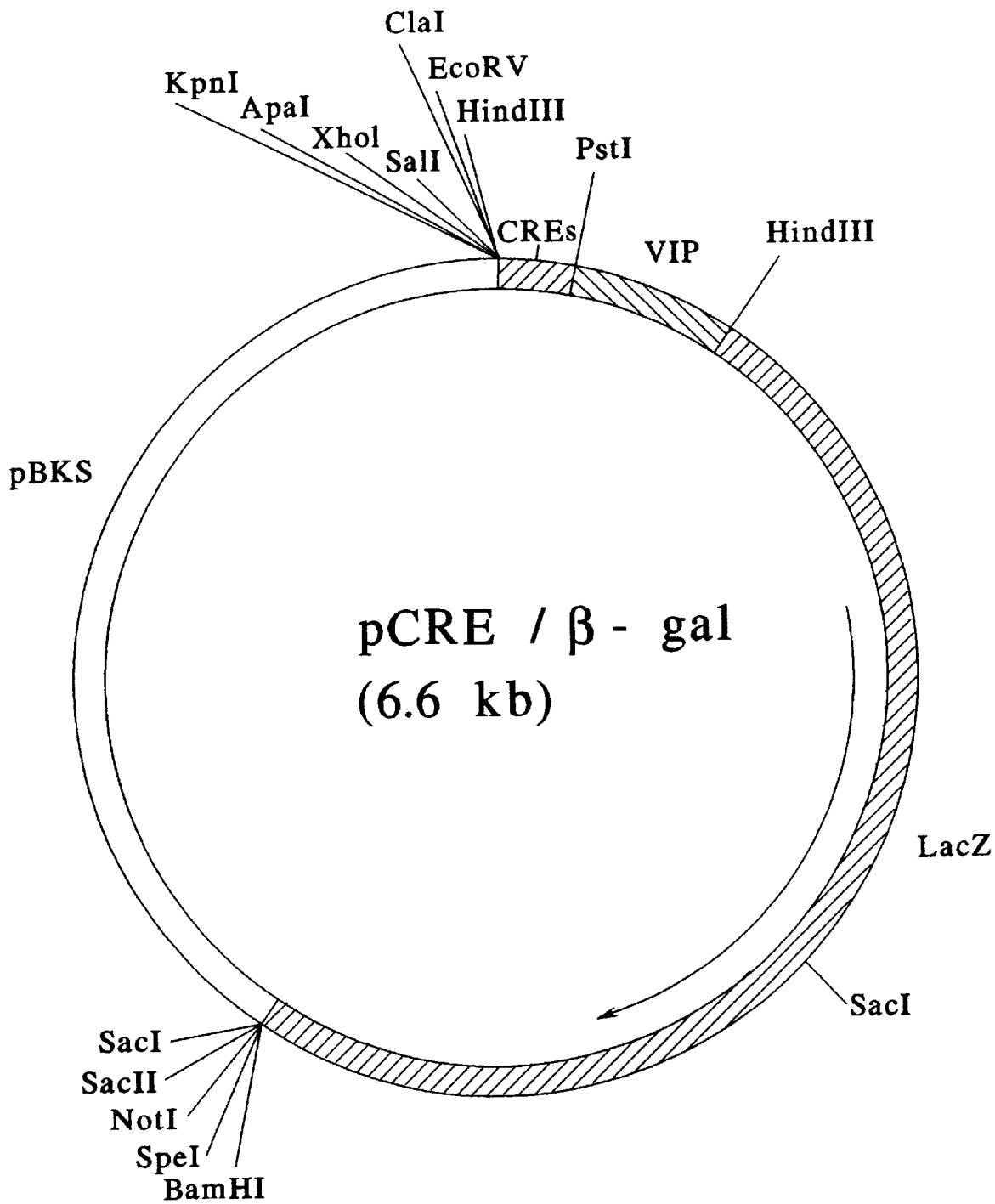
FIG. 14 illustrates the structure of the pCRE/β-gal plasmid.
Figure 15A:
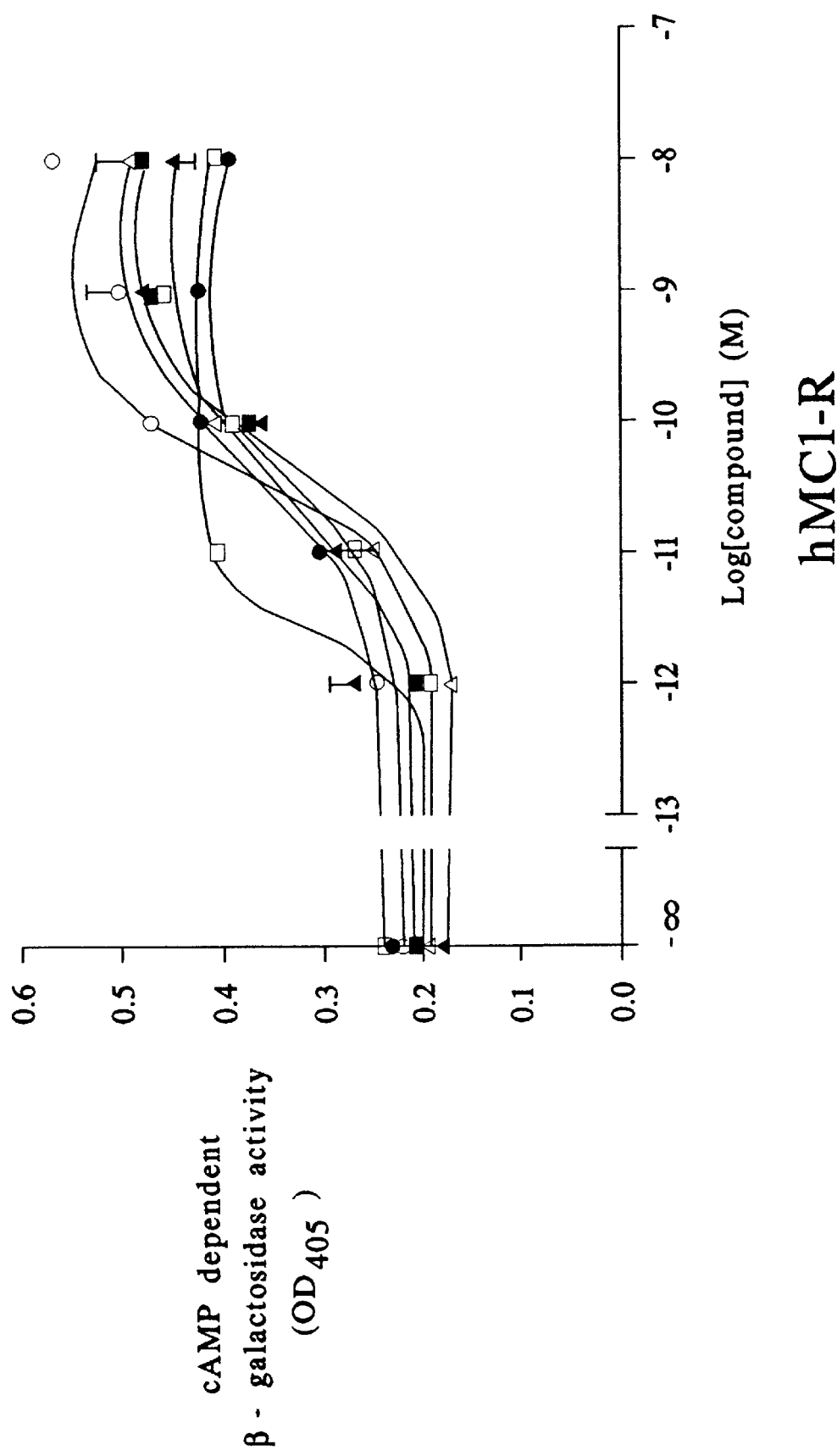
FIGS. 15A through 15D illustrates the results of the β-galactosidase-coupled, colorimetric melanocortin receptor binding assay using cells expressing each of the MC-1, MC-3, MC-4 or MC-5 receptors and contacted with αMSH or a variety of αMSH analogues.
Figure 15B:
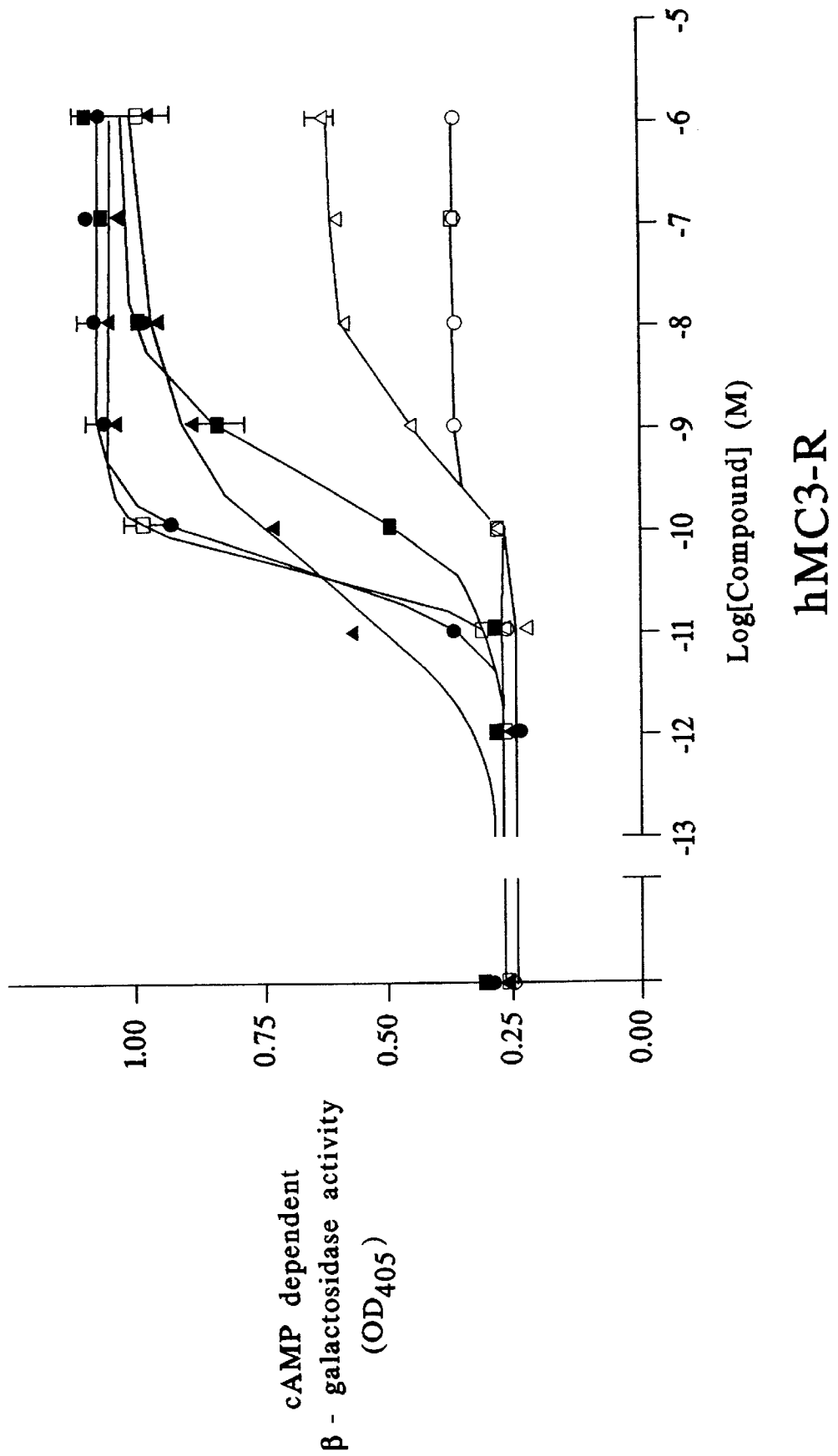
Figure 15C:
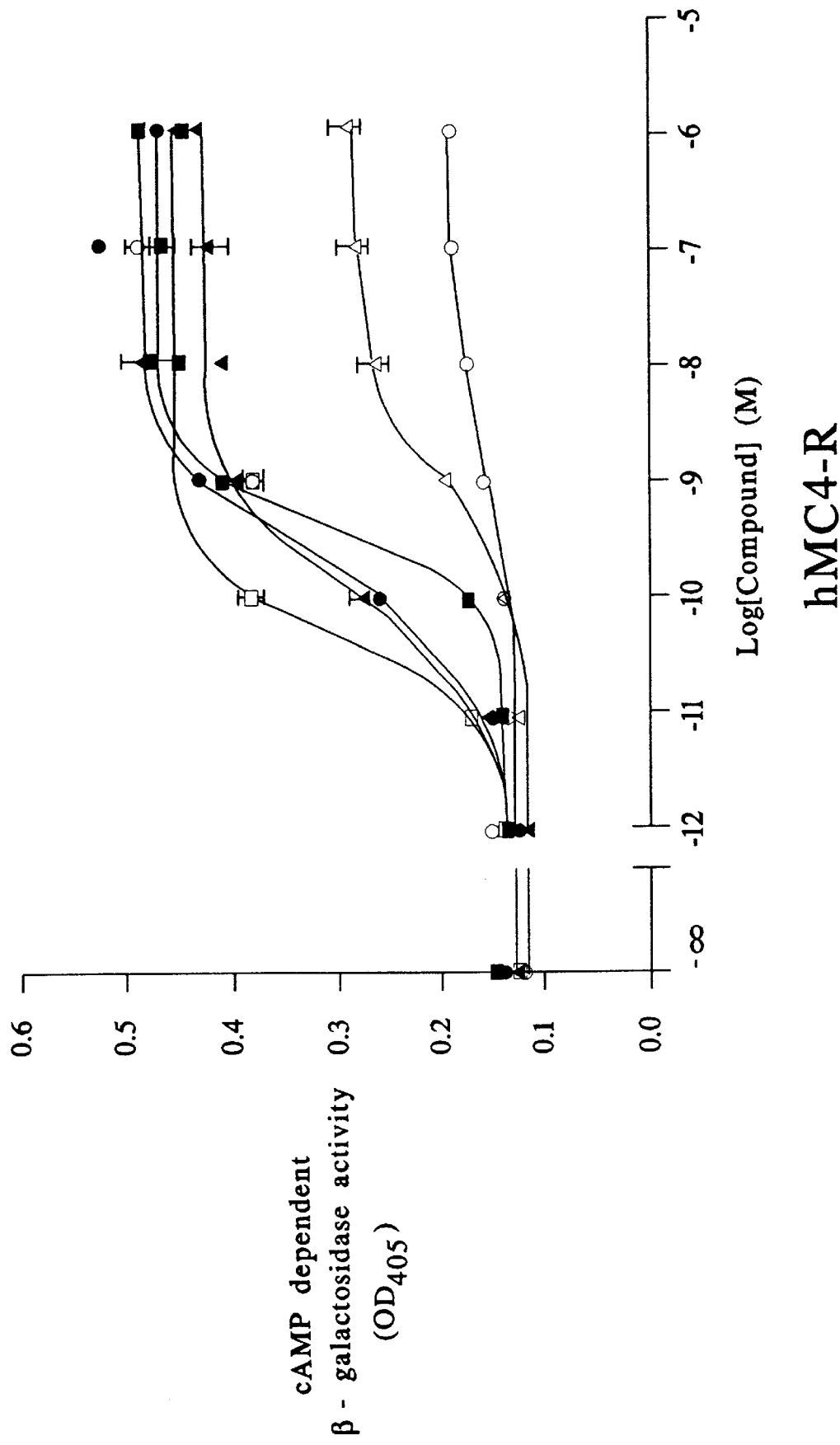
Figure 15D:
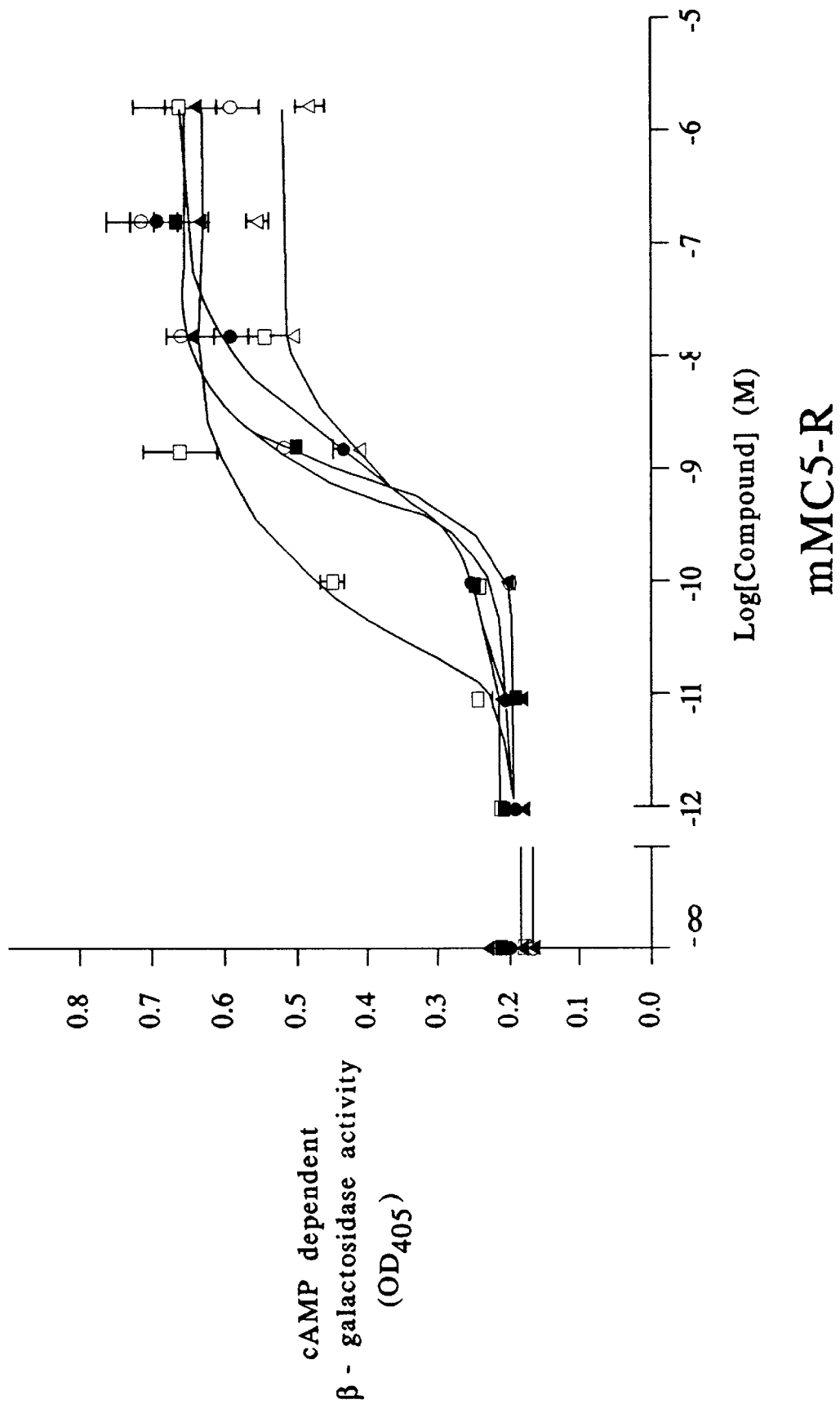
Figure 16A:
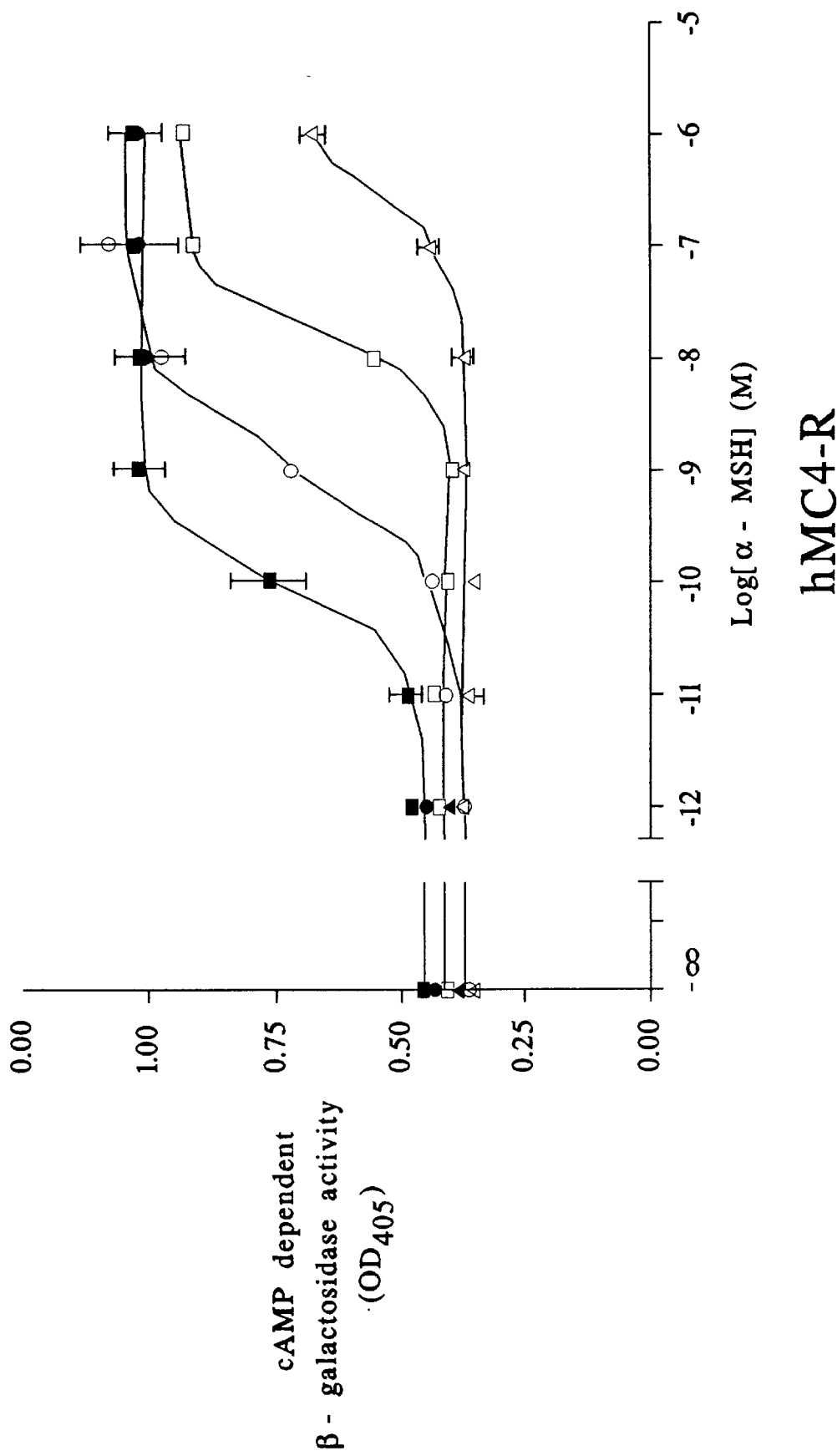
FIGS. 16A through 16D shows the results of the β-galactosidase-coupled, colorimetric melanocortin receptor binding assay to determine antagonist activity of melanocortin analogues SHU9119 and SHU8914 in cells expressing each of the melanocortin receptors MC-1, MC-3, MC-4 and MC-5.
Figure 16B:
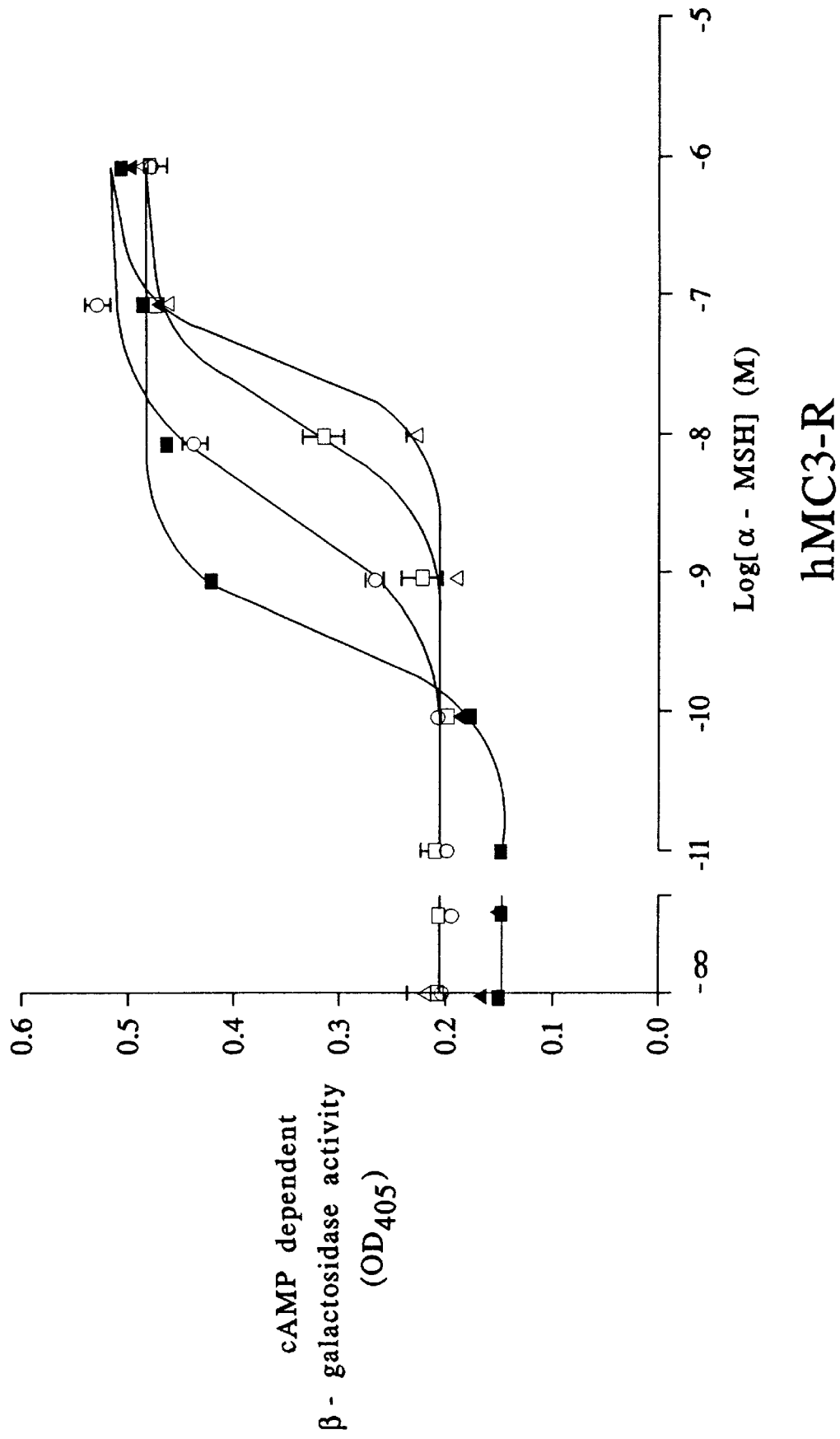
Figure 16C:
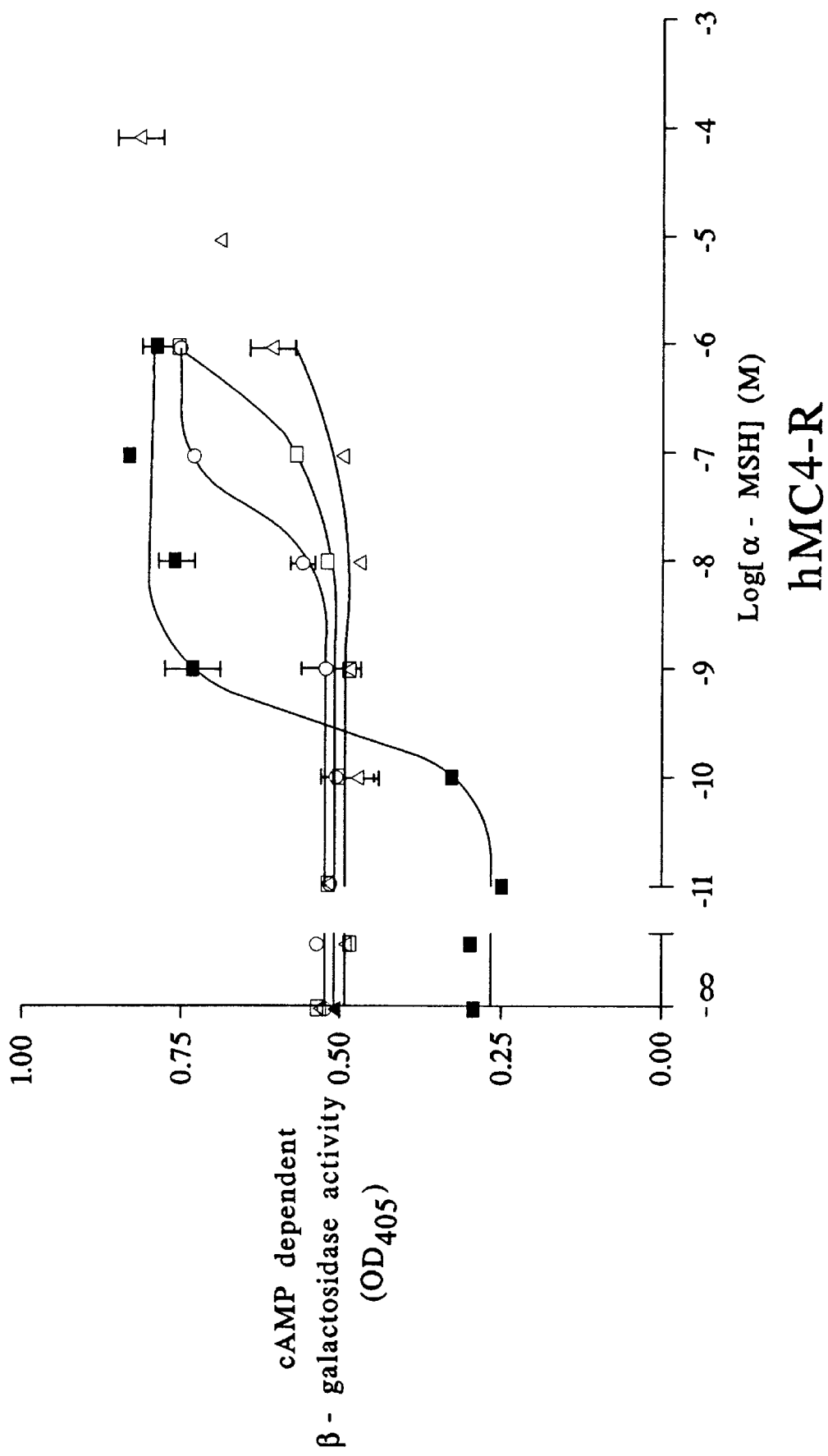
Figure 16D:
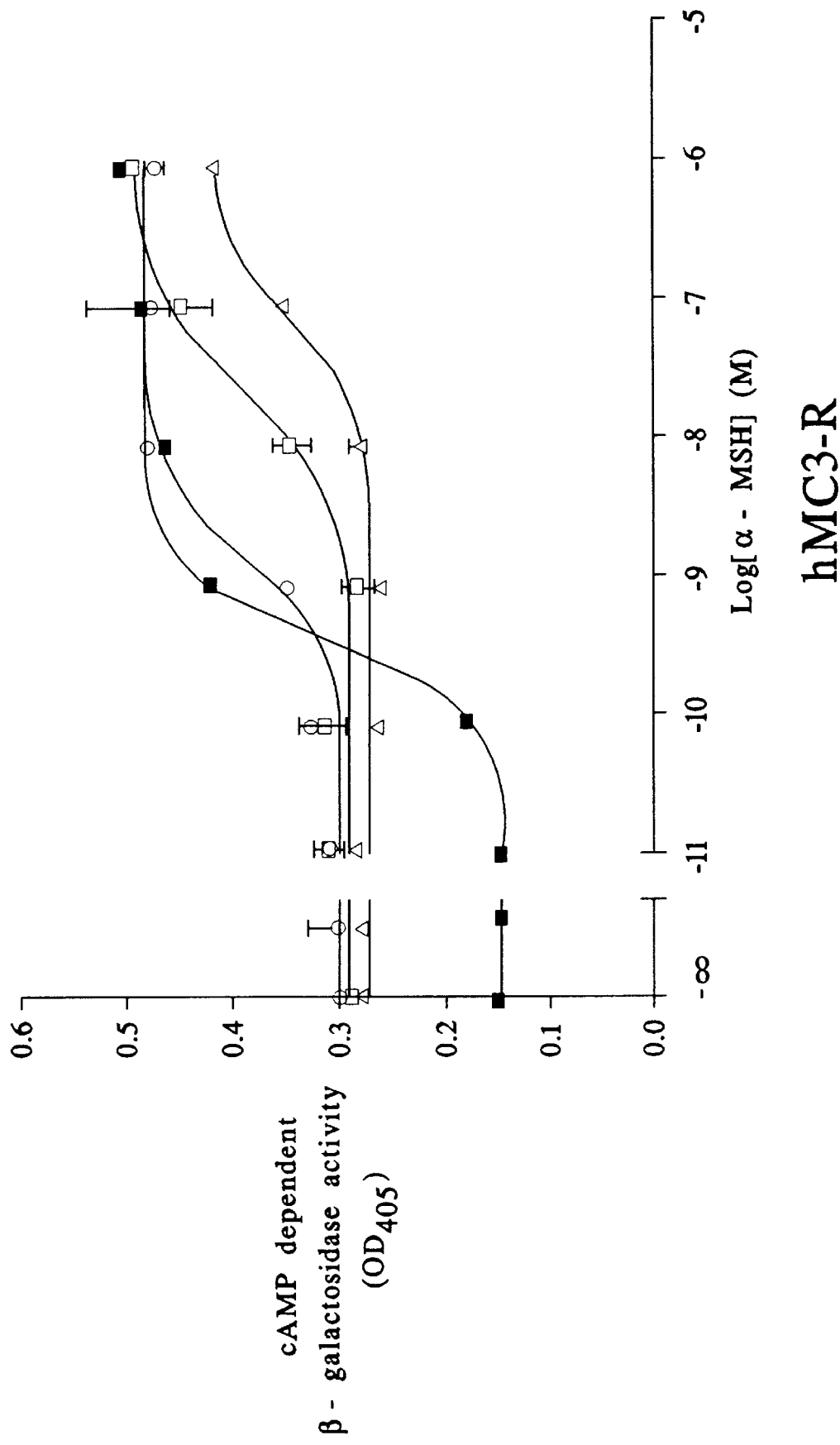

These analogues were tested for melanocortin receptor binding using a calorimetric assay system developed by some of the instant inventors (Chen et al., 1995, Analyt. Biochem. 226: 349–354) as follows. A series of concatamers of the synthetic oligonucleotide:

5'-GAATTCGACGTCACAGTATGACGGCCATG (SEQ ID No:19)

was produced by self-annealing and ligation and a tandem tetramer obtained. This fragment was cloned upstream of a fragment of the human vasoactive intestinal peptide (−93−+152; SEQ ID No.: 13; see Fink et al., 1988, Proc. Natl. Acad. Sci. USA 85: 6662–6666). This promoter was then cloned upstream of the β-galactosidase gene from E. coli. The resulting plasmid construct is shown in FIG. 14.

Transient transfection of the pCRE/β-gal plasmid described above was performed as follows. Cells at between 40–60% confluency (corresponding to about 1.5 million cells/6 cm tissue culture plate) were incubated with Opti-MEM (Gibco BRL, Long Island, N.Y.) and then contacted with a pCRE/β-gal-lipofectin complex which was prepared as follows. 3 μg plasmid DNA and 20 μL lipofectin reagent (Gibco) were each diluted into 0.5 mL Opti-MEM media and then mixed together. This mixture was incubated at room temperature for 15–20 min., and then the mixture (1 mL) added to each 6 cm plate. Transfected plates were incubated at 37° C. for 5–24 h, after which the plates were washed and incubated with DMEM media (Gibco) and the cells split equally into a 96-well culture plate.

To assay melanocortin receptor analogue binding, human 293 cells expressing each of the melanocortin receptors MC-1, MC-3, MC-4 and MC-5, and mouse Y1 cells expressing the MC-2 receptor, were transiently transfected with pCRE/β-gal as described above and assayed as follows. Two days after transfection, cells were stimulated with hormones specific for each receptor or hormone analogue by incubation for 6 h at 37° C. with a mixture comprising $10^{-12}$–$10^{-6}$M hormone or analogue, 0.1 mg/mL bovine serum albumin and 0.1 mM isobutylmethylxanthine in DMEM. The effect of hormone or analogue binding was determined by β-galactosidase assay according to the method of Felgner et al. (1994, J. Biol. Chem. 269: 2550–2561). Briefly, media was aspirated from culture wells and 50 μL lysis buffer (0.25M Tris-HCl, pH 8/0.1% Triton-X100) added to each well. Cell lysis was enhanced by one round of freezing and thawing the cell/lysis buffer mixture. 10 μL aliquots were sampled from each well for protein determination using a commercially-available assay (BioRad, Hercules, Calif.). The remaining 40 μL from each well was diluted with 40 μL phosphate buffered saline/0.5% BSA and 150 μL substrate buffer (60 mM sodium phosphate/1 mM $MgCl_2$/10 mM KCl/5 mM β-mercaptoethanol/200 μg/mL o-nitrophenyl-β-D-galactopyranoside) added. Plates were incubated at 37° C. for 1 h and then absorbance at 405 nm determined using a 96-well plate reader (Molecular Devices, Sunnyvale, Calif.). A series of two-fold dilutions from 20 ng of purified β-galactosidase protein (Sigma Chemical Co, St. Louis, Mo.) were assayed in parallel in each experiment to enable conversion of $OD_{405}$ to known quantity of β-galactosidase protein.

The results of these experiments are shown in FIGS. 15A through 15D. This Figure shows the results of the β-galactosidase assay described above using cells expressing each of the MC-1, MC-3, MC-4 or MC-5 receptors and contacted with αMSH or a variety of αMSH analogues, including SHIU9119. These results showed that SHU9119 had relatively weak agonist activity for both the human MC-3 and MC-4 receptors.

These results demonstrated the development of a colorimetric assay for cAMP accumulation as the result of melanocortin receptor binding to agonists and antagonists.

The action of MTII, SHU9119, and the endogenous mouse agouti peptide as agonists or antagonists of rodent MC receptors was determined by examining their ability to elevate intracellular cAMP in 293 cell lines expressing the rat MC3-R or mouse MC4-R (expressed as $IC_{50}$ values representing ligand concentrations required for half-maximal inhibition of binding of $^{125}I$-$(Nle^4,D$-$Phe^7)$ α-MSH tracer). Agonist/antagonist activity was also shown by demonstrating inhibition of cAMP elevation by the potent α-MSH analogue ($Nle^4$, D-$Phe^7$)α-MSH, using either a cAMP-responsive β-galactosidase reporter construct as described above, or by direct adenyl cyclase assay as described in Example 3 (wherein $EC_{50}$ values represent ligand concentration required for half-maximal activation of a cAMP-responsive β-galactosidase reporter). Competition binding experiments were determined as the amount of radioactivity bound in the presence of $5\times10^{-6}M$ cold ($Nle^4$, D-$Phe^7$)α-MSH, and was typically 3–5% of total counts bound.

In these experiments, murine agouti peptide was produced using a baculovirus system as described by Lu et al., (1994, *Nature* 371: 799–802), with the modification that the agouti peptide was purified from baculovirus supernatants by 0.6M NaCl step elution from an EconoS cation exchange column (BioRad). Agouti peptide used in these assays was approximately 60% pure.

Competition binding assays were performed to determine whether SHU9119 had antagonist activity towards αMSH binding to either the MC-3 or MC-4 receptors. These assays were performed as follows. Human 293 cells (100,000 cells/well in 24-well plates) expressing either the MC-3 or MC-4 receptors prepared as described above were incubated with a solution of 1 mg/mL BSA in PBS containing 100,000 cpm ($3.1\times10^{-10}$M ($^{125}I$)($Nle^4$, D-$Phe^7$)αMSH and varying concentrations of αMSH, ($Nle^4$, D-$Phe^7$)αMSH or SHU9119. Cells were incubated for 30 min at 37° C., washed twice with PBS-BSA, lysed with 0.5 mL 0.5N NaOH, and counted using a γ-counter to quantitate the amount of bound ($^{125}I$)($Nle^4$, D-$Phe^7$)αMSH. Control experiments showed non-specific binding to occur at about 3–5% levels, and this was taken into account when analyzing the experimental results.

Figure 17A:
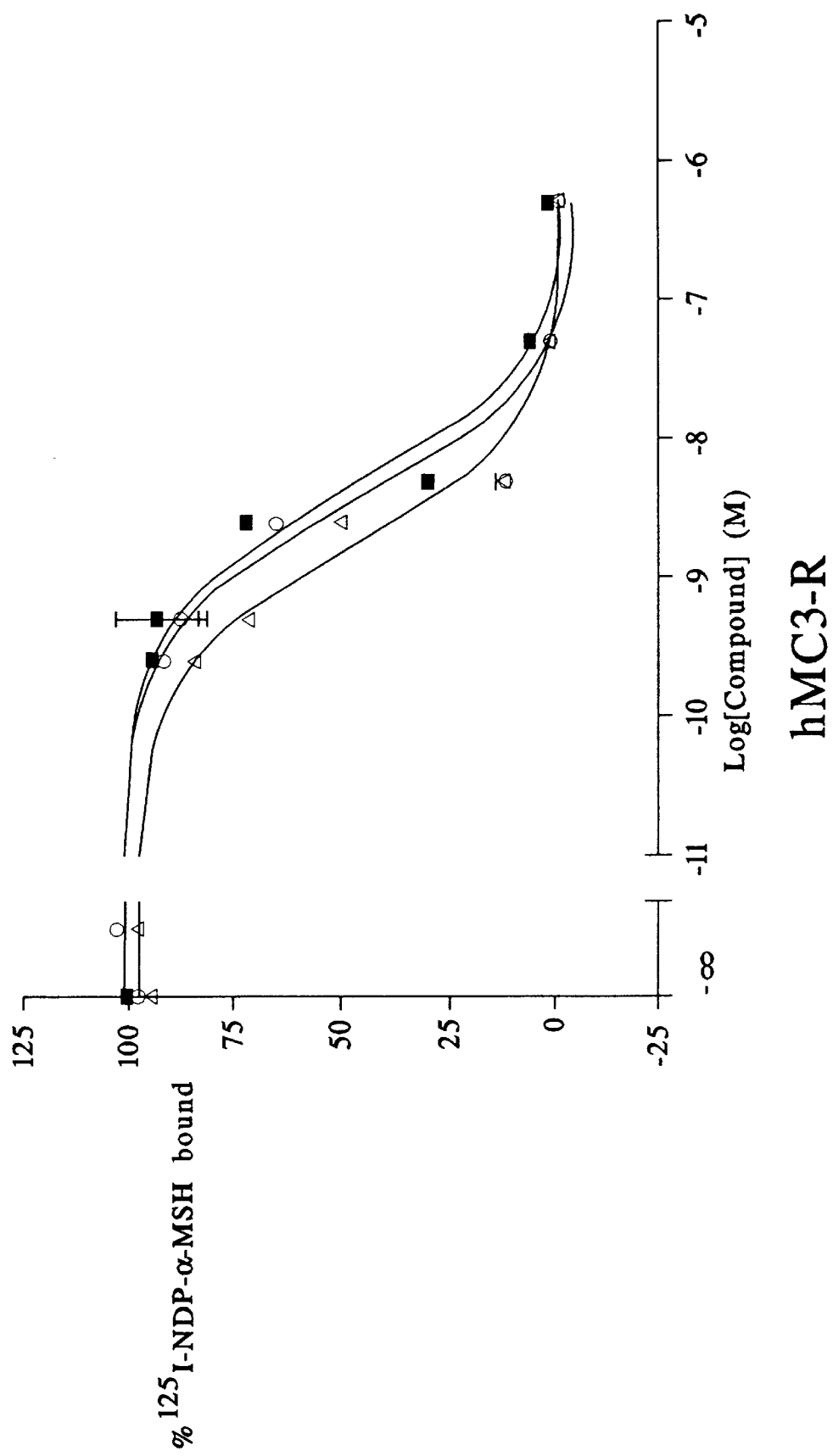
FIGS. 17A and 17B shows the results of classic competition binding assays using the melanocortin analogues SHU9119 and SHU8914 at the MC3R and MC-4 R receptors.
Figure 17B:
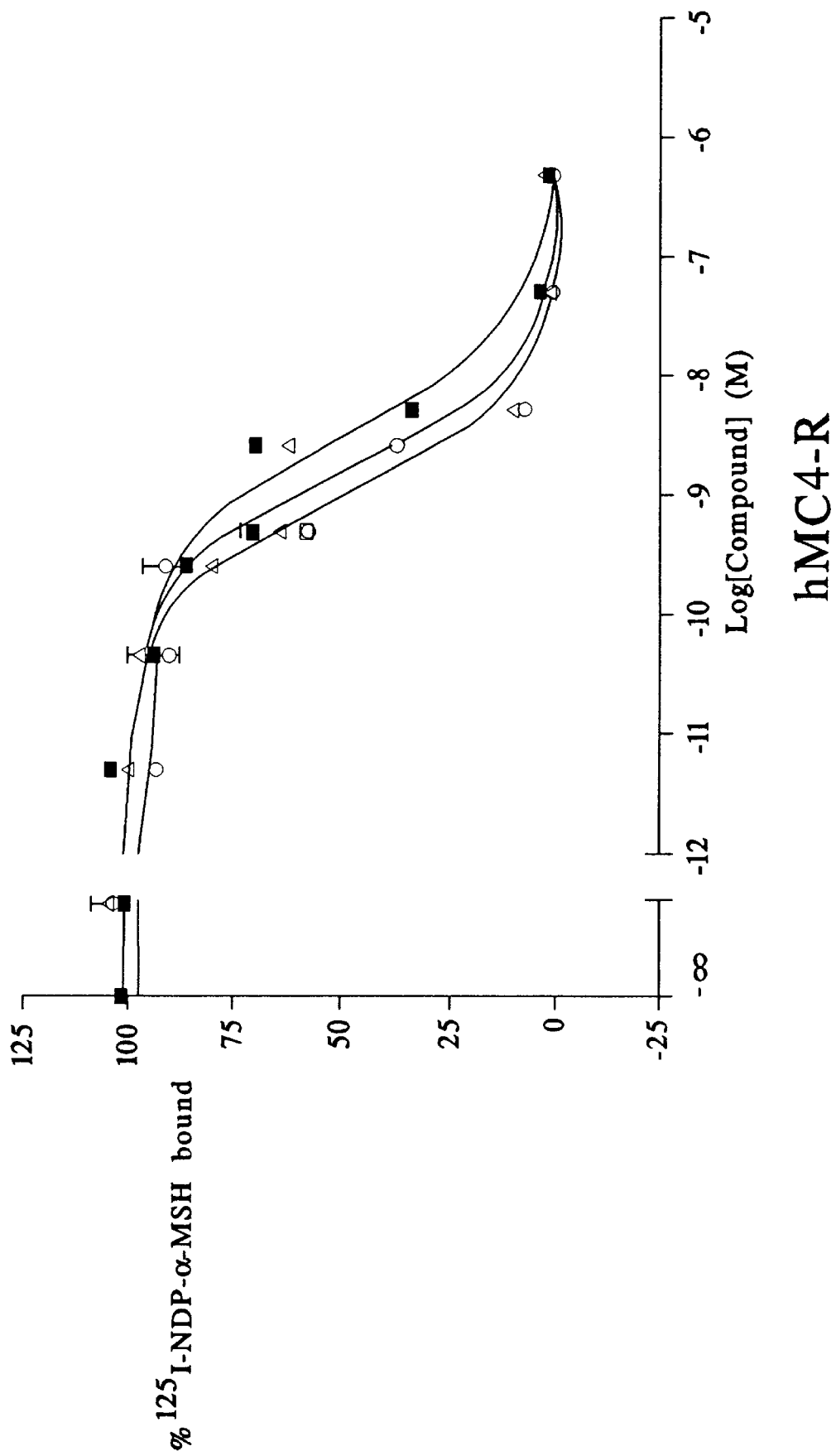

The SHU9119 analogue was found to be a potent antagonist of both the human MC-3 and MC-4 receptors, as shown in FIGS. 16A through 16D. These assays showed $pA_2$ values of 8.3 and 9.3 for the human MC-3 and MC-4 receptors, respectively, as determined using the method of Schild (1947, *Brit. J. Pharmacol.* 2: 189–206). In contrast, no significant alteration in $IC_{50}$ values was detected in binding experiments using this analogue with either the MC-3 or MC-4 receptors (FIGS. 17A and 17B).

Figure 18A:
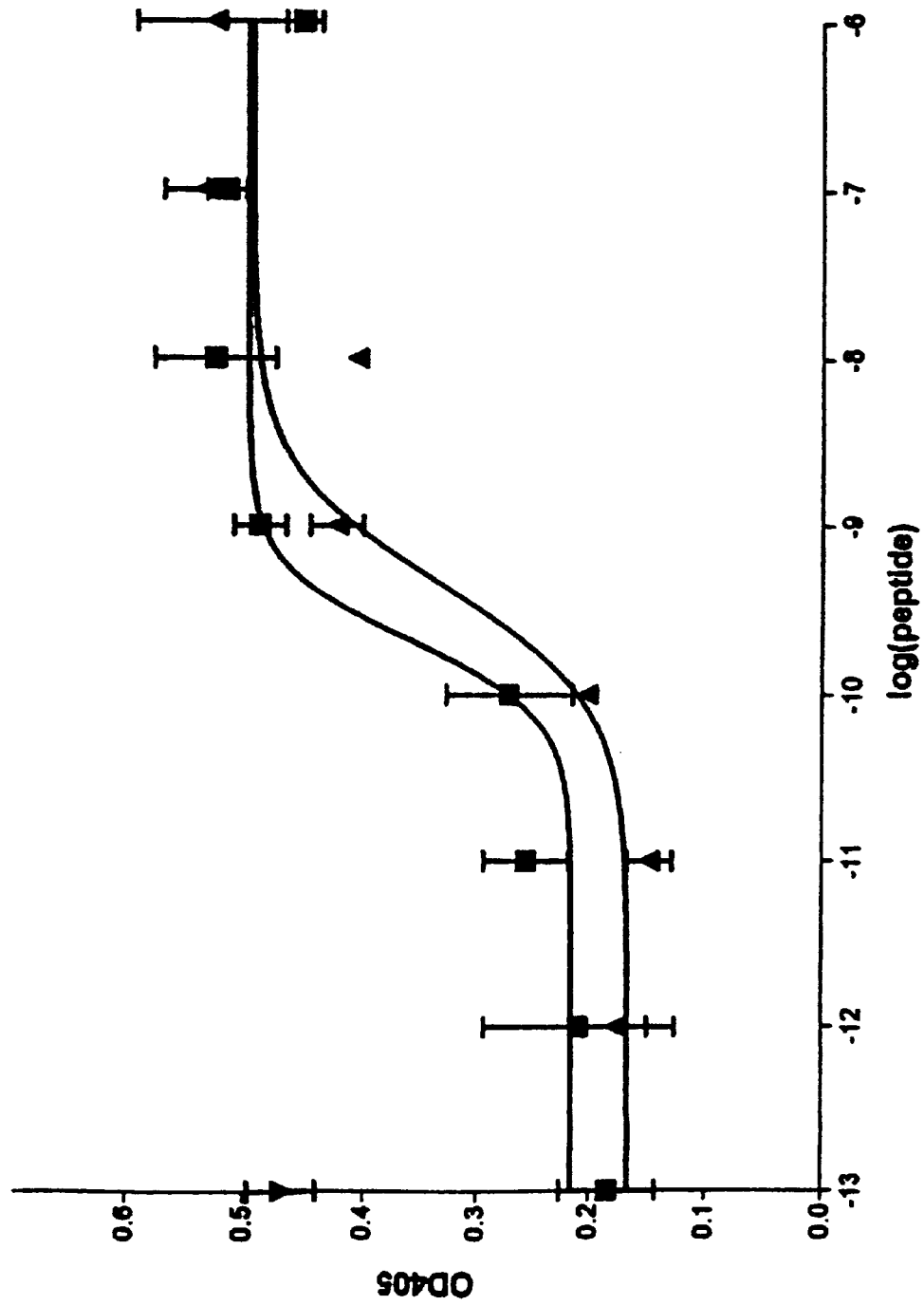
FIGS. 18A and 18B shows the results of cAMP accumulation experiments (performed using the β-galactosidase assay of Example 4) for mouse MC-4 receptor (FIG. 18A) and rat MC-5 receptor (FIG. 18B).
Figure 18B:
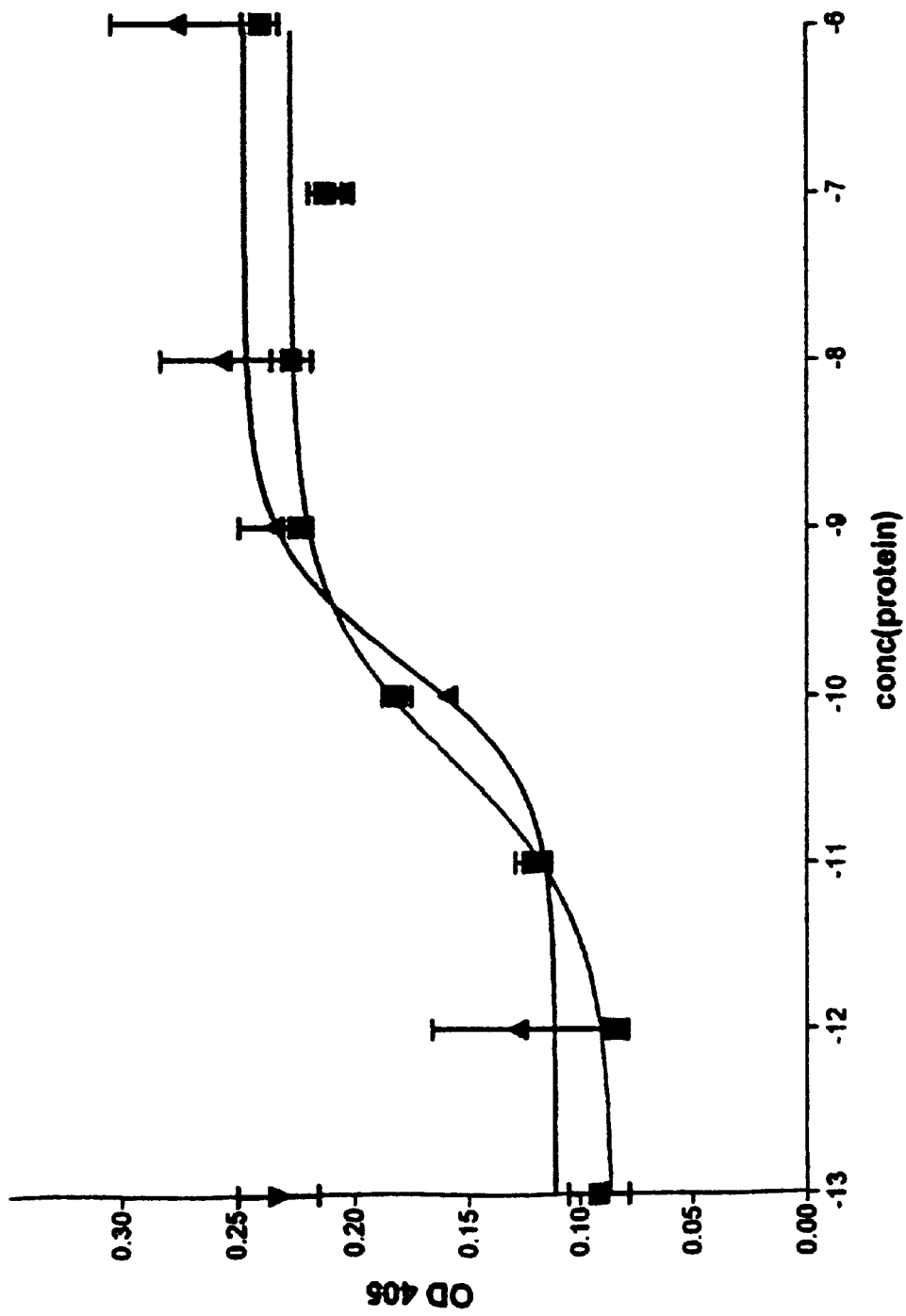

The activity of the MTII analogue was also assayed for melanocortin receptor agonist activity. These results are shown in FIGS. 18A and 18B, and confirmed that the MTII analogue is a specific agonist of the MC-3 and MC-4 receptors.

Specific competition of ($Nle^4$, D-$Phe^7$)α-MSH binding to the rat MC-3 receptor by agouti peptide was observed, although accurate $IC_{50}$ values could not be determined because the peptide preparation was not homogeneous (results not shown). Specific competition of αMSH activation of human MC-4R by agouti was previously disclosed (Lu et al., 1994, *Nature* 371: 799–802).

EXAMPLE 5

Feeding Behavior Effect of Melanocortin Analogue Binding in Brain

The results shown in Example 4 above suggested a role in the regulation of feeding behavior in mammalian brain for MC receptor agonists and antagonists, in view of the antagonist properties of the agouti peptide at the MC-3 and MC-4 receptors. The agouti peptide was known to cause obesity when expressed ectopically in the mouse, and has been found to be a high affinity antagonist of the melanocyte stimulating hormone receptor (MC-1R) and of the hypothalamic MC-4 receptor (see Lu et al., ibid.). The former activity explained the inhibitory effect of the agouti peptide on eumelanin pigment synthesis. Similarly, it was hypothesized by the inventors that agouti causes obesity in mice by antagonizing hypothalamic MC-4 receptors. The cyclic melanocortin analogue, SHU9119, having been shown herein and elsewhere (Hruby et al., ibid.) to be a specific, high affinity antagonist of the MC-3 and MC-4 receptors, was tested for the effect of direct administration to mouse brain on feeding behavior in the animals. Intracerebroventricular (ICV) administration of SHU9119 was performed to avoid any complications caused by inhibition of peptide traverse of the blood-brain barrier.

Briefly, male C57B1/6J mice (18–29 g) were maintained on a normal 12 hr/12 hr light dark cycle with food (Purina mouse chow) and water ad libitum. Animals were housed individually for 24 hrs, distributed into experimental and control groups, avoiding any bias as a function of prior weight, then injected with vehicle or vehicle plus drug just prior to the onset of a 12 hr light or dark cycle. Fasted animals were deprived of food from 18:00 to 10:30 hrs to stimulate feeding during the daytime experimental period. Animals were lightly anesthetized with halothane, and administered into one lateral ventricle 2 μL of a solution of artificial cerebrospinal fluid alone (acsf, comprising 130 mM NaCl, 27mM $NaHCO_3$, 1.2 mM $Na_2HPO_4$, 0.3 mM $NaH_2PO_4$, 0.5 mM $Na_2SO_4$, 1.0 mM $CaCl_2$, 1.0 mM $MgCl_2$, and 2.5 mM KCl), or 6 nmol SHU9119 in acsf. Freehand injections were performed as described by Laursen and Belknap (1986, *J. Pharmacol. Methods* 16: 355–357) with some modifications. A 10 μl luertip syringe (Hamilton 701 LT) was fitted with a 0.5 inch 27 gauge needle. Stiff Tygon tubing was slipped over the needle to expose 3 mM of the needle tip. The syringe was held at a 45° angle from the front of the skull with the bevel facing up. The coronal suture was found by lightly rubbing the needle over the skull. Maintaining the 45° angle, the needle was then inserted 1–2 mm lateral to the midline, using only mild pressure to insert and remove the needle. The compounds indicated in a 2 μl volume of acsf were administered slowly over approximately 15 seconds, and the needle removed after 35 seconds. Animals were allowed to recover from anesthesia and placed into a cage containing a premeasured quantity of food pellets in a spill-free cup. Moribund animals were not included in the study.

Figure 19A:
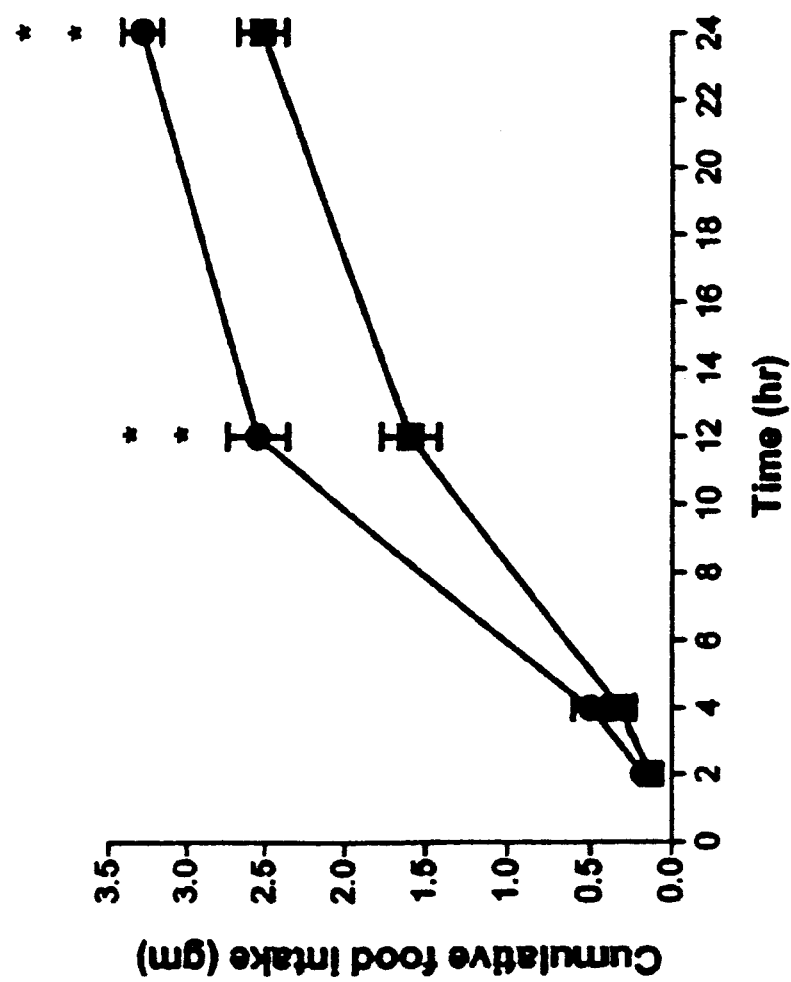
FIGS. 19A through 19C show the effect on food intake of intracerebroventricular administration of melanocortin analogue SHU9119 in mice.
Figure 19B:
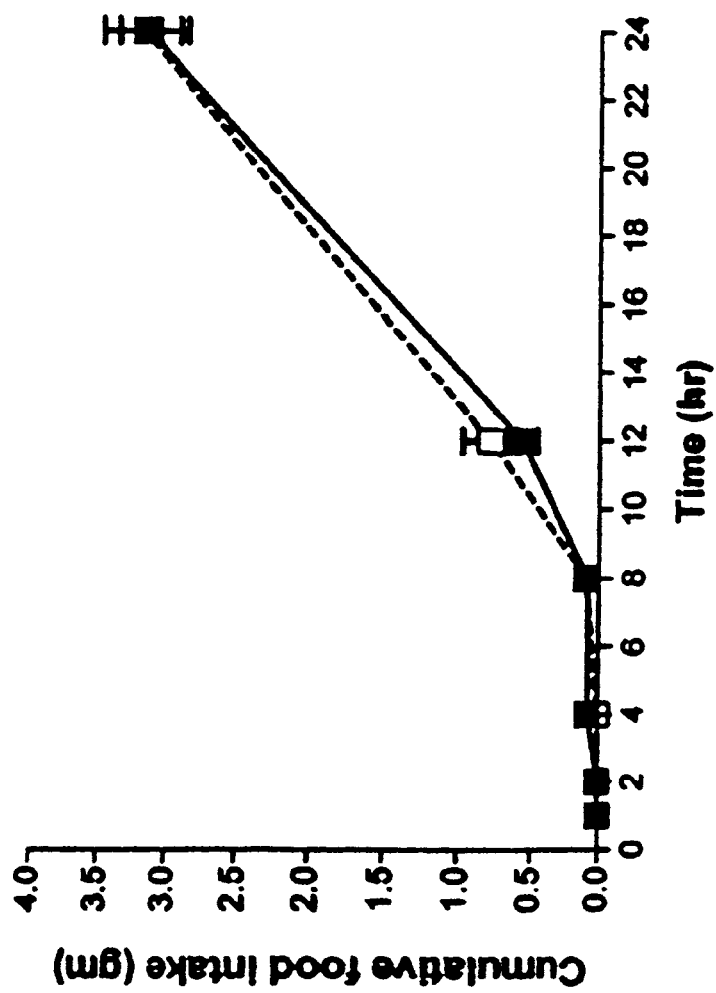
Figure 19C:
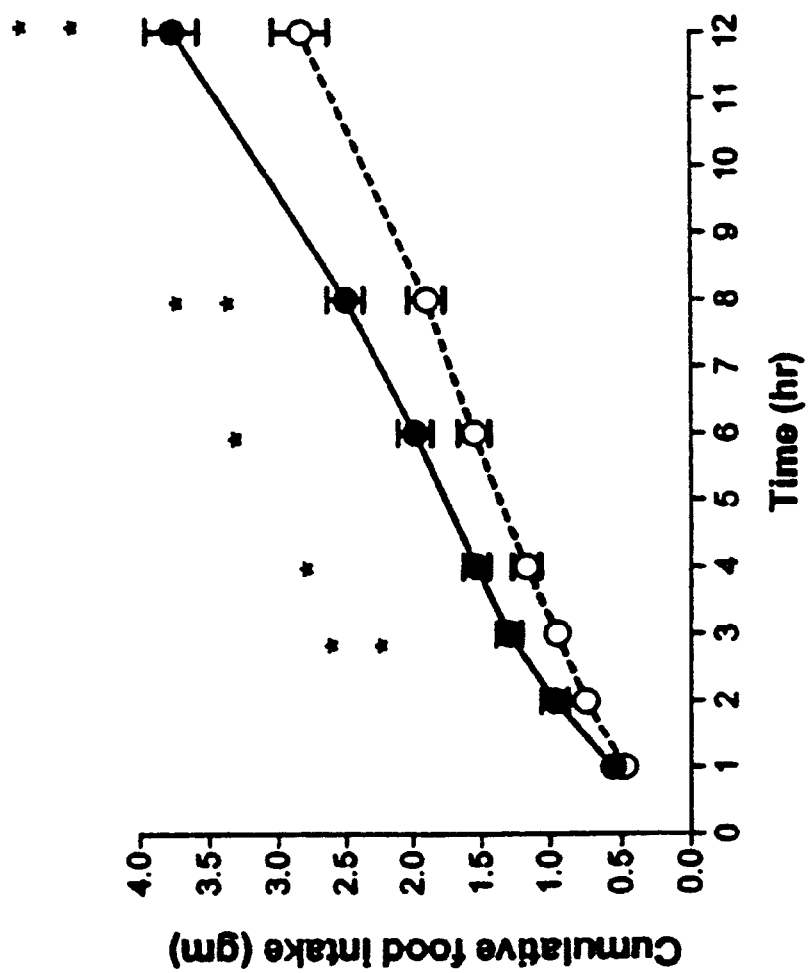

Stimulation of feeding by intracerebroventricular administration of the melanocortin antagonist SHU9119 is shown in FIGS. 19A through 19C. Curves show cumulative food intake as a function of time following administration of the substances shown. FIG. 19A shows stimulation of feeding by administration of SHU9119 just prior to lights off (19:00 hrs) to C57B 1/6J mice fed ad libidum. FIG. 19B, in contrast, shows no effect of morning (10:00 hrs) SHU9119 administration in C57B1/6J mice fed ad libidum. FIG. 19C illustrates stimulation of daytime feeding by SHU9119 administration in fasted C57B1/6J mice. In deriving the data points comprising these Figures, food remaining was briefly removed and weighted indica time intervals indicated. Data points indicate the mean and bars indicate standard error. Significance of the effect over time was determined by ANOVA with repeated measures. Significance of drug effects at individual time points was determined by two-way ANOVA, and is indicated in each Figure (*=$P<0.001$, =$P<0.01$, *=$P<0.05$).

These results demonstrated that ICV administration of SHU9119 into one lateral ventricle of the C57B 1/6J mouse just prior to lights out led to a mean 60% increase in food intake over 12 hrs (FIG. 19A; $P<0.005$). In contrast, daytime food intake in animals fed ad libidum was not stimulated by administration of SHU9119 (FIG. 19B). SHU9119-treatment did, however, significantly stimulate daytime food intake in animals fasted for 16 hrs prior to the experiment (FIG. 19C; $P<0.001$). Stimulation of feeding was evident at approximately two hrs post-treatment, and continued for 12 hrs, to produce a mean 34% in food intake relative to vehicle-injected controls.

These results supported the hypothesis that agouti or SHU9119 stimulate feeding by antagonizing MC receptors in the central nervous system. To further test this hypothesis, a series of experiments were performed wherein MC receptor agonists were administered to animals primed by fasting to eat, to determine whether feeding in such animals could be inhibited by the MC receptor agonists. Animals were induced to feed by food deprivation for 16 h prior to ICV administration of the non-specific melanocortin agonist MTII. In these experiments, ICV injections in male C57B1/6J mice (20–30 g) and the measurement of food intake were as described above.

Figure 20A:
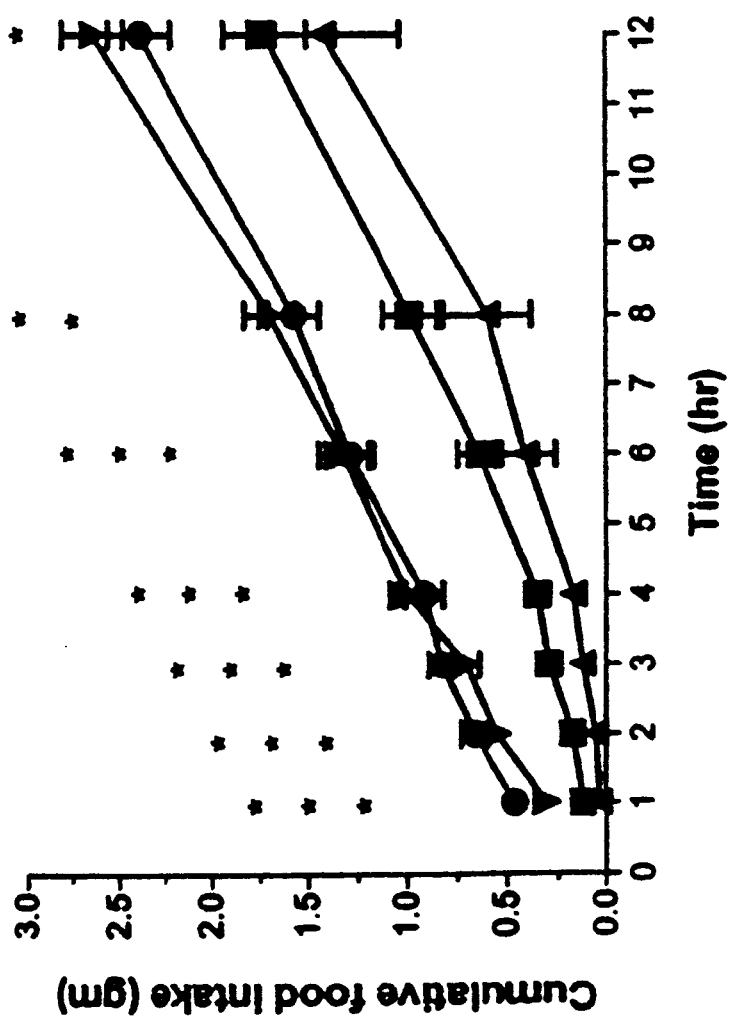
Figure 20B:
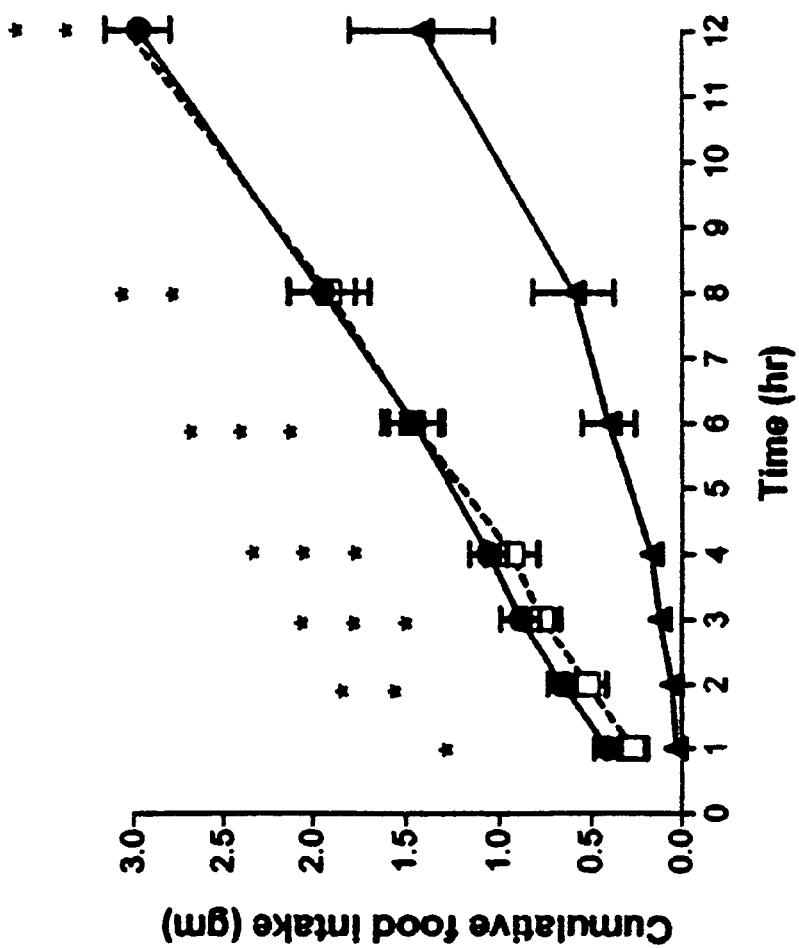

Results of these experiments are shown in FIGS. 20A through 20C. In comparison to vehicle-injected animals, MTII was found to produce a potent inhibition of feeding within one hour after administration (FIG. 20A) in a dose-responsive manner. Food intake was significantly inhibited for up to four hours following administration ($P<0.001$) at the highest dose administered (3 nmol), and decreased food intake continued for the next four hours with normal rates of food intake resuming at about 8 hours after treatment. This dose-responsive inhibition of feeding had an $IC_{50}$ at the two hour time point of approximately 0.5 nmol (FIG. 20C). However, inhibition of feeding with 3 nmol MTII was completely blocked by co-administration of 6 nmol SHU9119 (FIG. 20B; $P<0.001$), demonstrating that the effect results specifically from agonist binding to the MC-4 and/or MC-3 receptor.

Figure 20D:
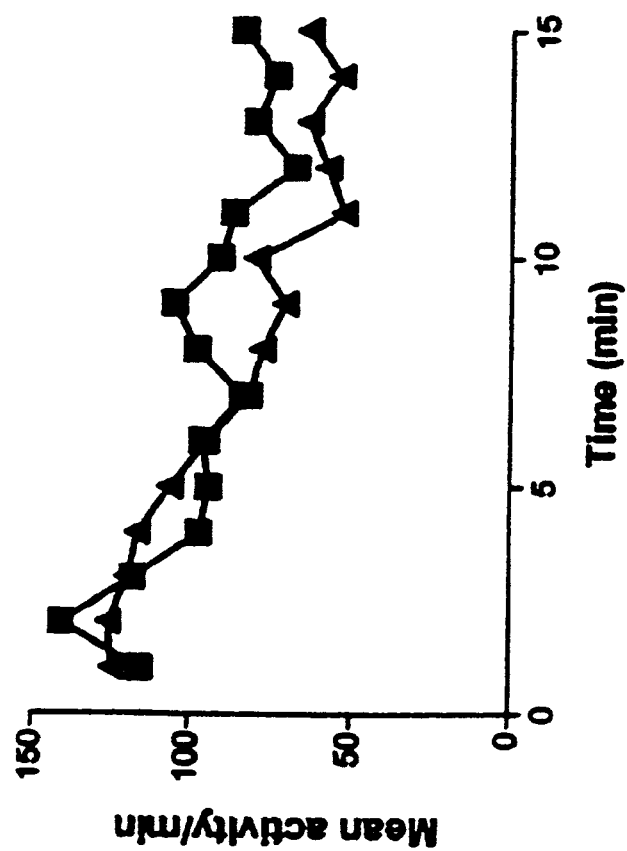
FIG. 20D shows the effect on locomotor activity of intracerebroventricular administration of melanocortin analogue MTII in mice.

Locomotor assays were performed to determine whether the effects on feeding behavior observed in these mice were secondary to generalized behavioral effects caused by administration of these melanocortin analogues. The effects of MTII on locomotor activity were tested by placing vehicle or MTII-treated mice in sound and light-proof cages containing multiple light beam detectors. These assays were performed by first injecting 3 nmol MTII or acsf as described above. At three hours (2:45–3:25) post-injection, 12 mice were placed into 12 separate boxes containing multiple infrared light sources and photodetectors. The boxes were contained within separate ventilated light and sound attenuating chambers (Coulboum model E10-20). Disruption of the infrared beams, with a 10 msec. resolution, was tallied independently for each one minute time period in each cage. The results of these assays are shown in FIG. 20D. Data points indicate the mean total activity (# of light breaks) for 6 animals in each experimental group. Four way ANOVA statistical analysis was used to analyze the data, and indicated an absence of a significant difference among the two groups.

Inhibition of feeding by MTII could not be explained by any apparent behavioral abnormalities, or any effect on arousal or locomotor activity. MTII-treated animals appeared alert and exhibited no unusual behavior relative to controls. At approximately three hours after ICV administration, MTII-treated animals exhibited locomotor activity that was indistinguishable from vehicle-treated animals (FIG. 20D). The higher initial activity, indicative of exploratory behavior, and continued locomotion over a 15 min period was indistinguishable between the two groups, indicating that the inhibition of feeding was not due to decreased locomotion or decreased arousal.

Figure 21A:
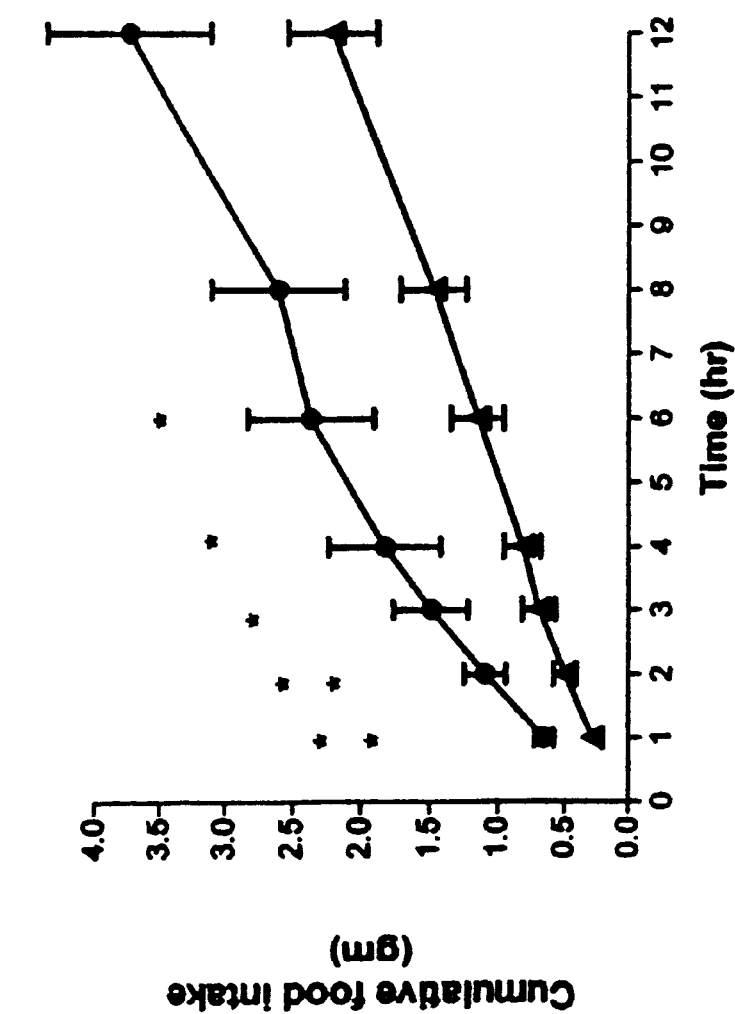
FIGS. 21A through 21D show the effect on food intake of intracerebroventricular administration of melanocortin analogue MTII in mice.
Figure 21B:
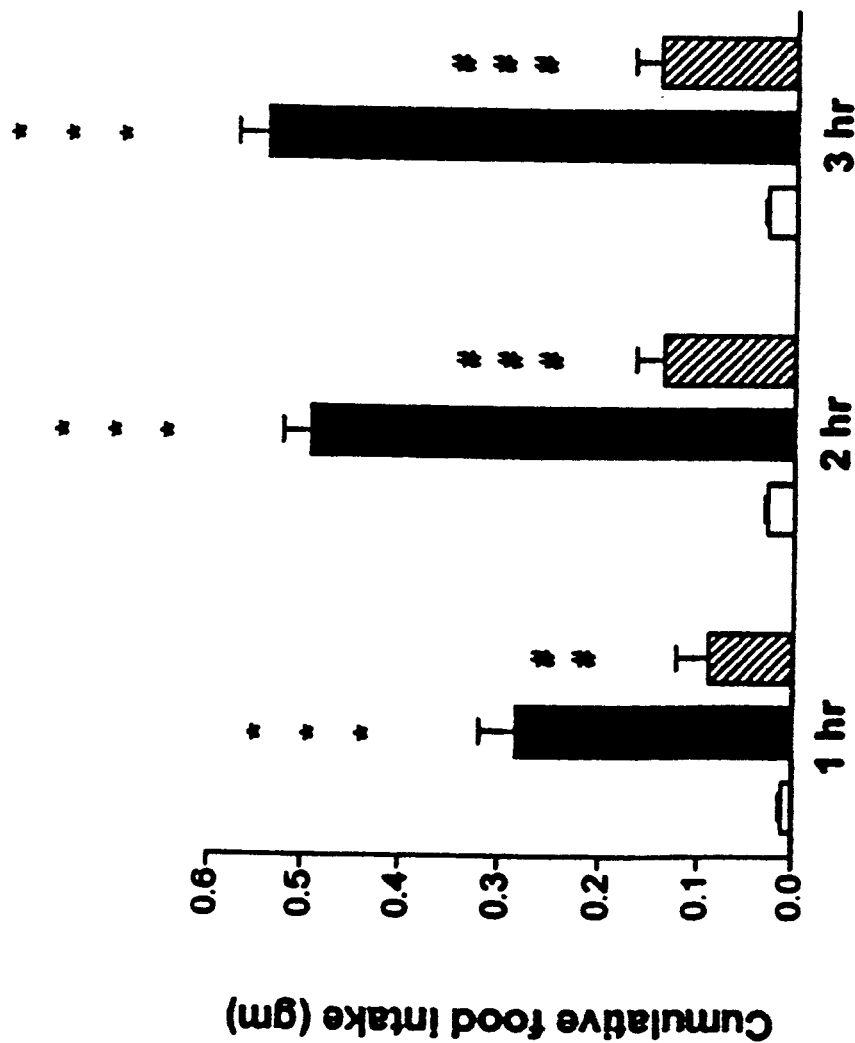
Figure 21C:
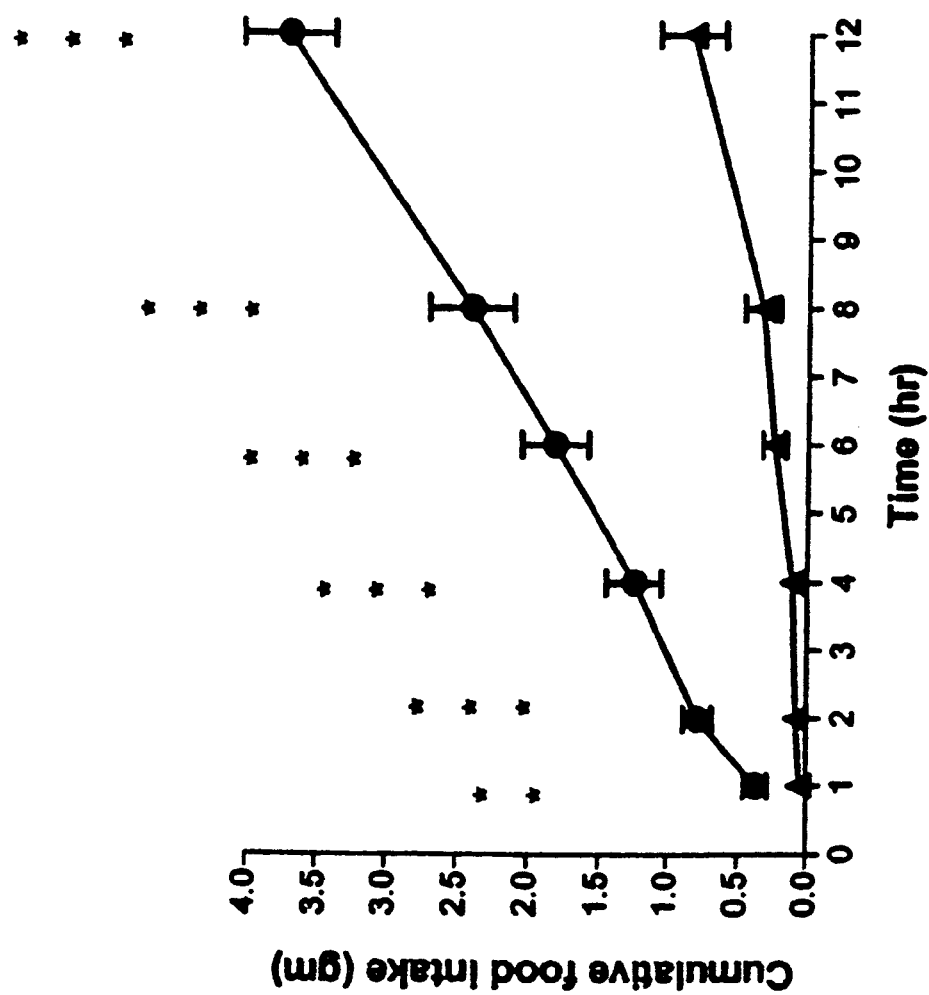
Figure 21D:
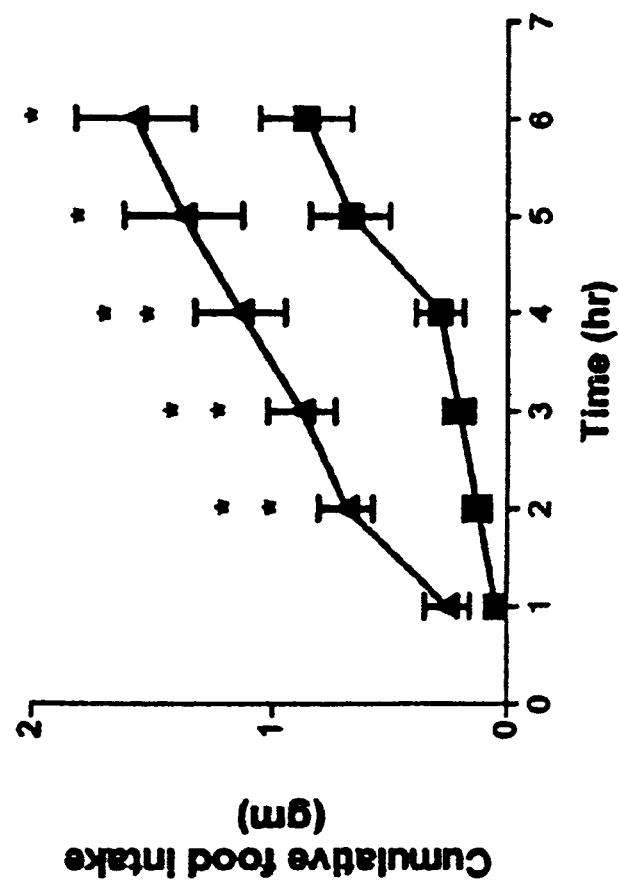

The administration of MTII also inhibited food intake in three other models of hyperphagia: the C57B1/6J-Lep$^{ob}$ mouse, C57B1/6J-A$^Y$ mouse, and NPY-injected C57B/1/6J mouse. FIG. 21A shows inhibition of feeding by intracerebroventricular administration of MTII in A$^Y$ mice (females, 19–28 gms). FIG. 21B shows inhibition of feeding by intracerebroventricular administration of MTII in C57B1/6J mice (females, 21–25 gm) stimulated to feed by co-administration of neuropeptide Y. FIG. 21C shows inhibition of feeding by intracerebroventricular administration of the MTII in ob/ob mice (females, 48–69 gms). FIG. 21D shows inhibition of feeding in ob/ob mice intraperitoneal administration of MTII (females, 40–45 gms). ICV injections and measurement of food intake was performed as described above, with the exception of NPY treated animals, which were not fasted prior to experimentation. Animals treated intraperitoneally received 100 μl of a 1 mM solution of MTII in saline, and vehicle injections consisted of the same value of saline alone. Significance indicated for individual time points, determined as described above, was for 3 nmol MTII vs. acsf (FIG. 21A), 1.18 nmol NPY vs. 1.18 nmol NPY+3 nmol MTII (FIG. 21B), 3 nmol MTII vs. acsf (FIG. 21C), and 100 nmol MTII vs. saline (FIG. 21D).

The hyperphagia in these models can be clearly seen by comparing the 12 hr food intake following a fast in vehicle-injected C57B/1/6J (2.4 g, FIG. 19A), C57B1/6J-A$^Y$ (3.7 g, FIG. 21A) and C57B1/6J-Lep$^{ob}$ (3.7 g. FIG. 21C) animals. As expected, MTII treatment inhibited food intake following a 16 hr fast in the C57B1/6J-A$^Y$ mouse (FIG. 21A; $P<0.05$). Interestingly, while food intake for the first four hours is significantly inhibited relative to vehicle-injected animals, it is also significantly less inhibited in the C57B1/6J-$A^Y$ animal than in the C57B/1/6J animal given the same 3 nmol dose (compare, FIG. 20A versus FIG. 21A, 1–4 hrs; P<0.001). The decreased effectiveness of the agonist in the presence of the $A^Y$ allele is consistent with the proposal that his allele results in chronic expression of agouti peptide melanocortin antagonist in the brain.

MTII, upon co-administration, also significantly inhibited the profound stimulation of feeding induced by neuropeptide Y (NPY), measured over a three hr period (FIG. 21C; P<0.005). Co-administration of an approximately two-fold molar excess of MTII produced a 74% inhibition of NPY-stimulated food intake at the three hour time point.

Finally, MTII also inhibited hyperphagia due to absence of leptin in the C57B1/6J-$Lep^{ob}$ mouse (FIG. 21C; P<0.001). MTII blocked feeding as potently (FIG. 20A), in contrast to the less potent inhibition described above for the C57B1/6J-$A^Y$ mouse.

The C57B/1/6J-$Lep^{ob}$ animal was also used to test the ability of MTII to regulate feeding when administered peripherally. Moderate doses (100 nmol) of MTII were inhibited feeding in the C57B1/6J-$Lep^{ob}$ mouse (P<0.001) while low doses (10 nmol) did not (date not shown). The kinetics were similar to those seen with ICV administration, with a potent inhibition of feeding for the first four hours. The 100-fold higher dose required peripherally, as well as the similar kinetics suggest a primarily central nervous system mechanism of action of MTII.

These data show that melanocortinergic neurons exert a tonic inhibition of feeding behavior, and that disruption of this signal leads to hyperphagia. With regard to the recently-discovered leptin hormone made by adipocytes, which is generally expressed at elevated levels in obese humans and rodents (such as the C57B1/6J-$Lep^{ob}$ animal), the regulatory defect is understood to be an incapacity to respond properly to the leptin hormone signal. The instant results indicate that the melanocortins act independently, or physiologically "downstream," from the leptin hormone/receptor interaction, because it has been shown herein that melanocortin receptor agonists can potently inhibit feeding in the C57B1/6J-$Lep^{ob}$ animal.

These results suggest that MC receptor agonists and antagonists can affect mammalian feeding behavior, and provide a means for determining candidate compounds for the development of effective pharmacological products directed towards alleviating such human ailments as obesity, anorexia and cachexia.

EXAMPLE 6

Use of MC Receptor-Expressing Recombinant Cells for Screening Compounds that Affect Feeding Behavior in Mammals The results obtained in Example 6 indicated that cells expressing a variety of mammalian melanocortin receptors are useful for characterizing compounds as a first step towards developing MC receptor agonists and antagonists for controlling feeding behavior in mammals, particularly obesity and overweight disorders in general, as well as anorexia, cachexia and other failure-to-thrive disorders.

A panel of mammalian melanocortin receptor-expressing recombinant cells are provided as described above in Example 3, wherein each member of the panel comprises appropriate mammalian cells, such as human 293 cells, comprising a recombinant expression construct encoding the MC-1, MC-2 (ACTH), MC-3, MC-4 or MC-5 receptor, the panel constructed to comprise cells functionally expressing each of these MC receptor proteins.

The panel is used as follows. Receptor agonist activity is assayed by transient or stable expression of a protein which produces a metabolite reporter molecule in response to receptor binding by any of the MC receptor proteins. An example of such a reporter system is the recombinant expression construct described in Example 4, wherein cAMP responsive elements (CREs) are operatively linked to bacterially-derived β-galactosidase (β-gal) gene. In the event of receptor binding, cAMP is produced in the mammalian cell, and the CRE induces β-gal expression. When co-incubated with a colorless substrate for β-gal, receptor binding results in conversion of the colorless substrate to a blue-colored product, which can be easily scored visually or spectrophotometrically. Alternative reporter genes, such a luciferase, can also be used as reporter systems, provided that expression of the reporter molecule-producing protein is functionally linked to receptor binding of a test compound. Alternatively, cAMP production resulting from MC receptor binding can also be measured directly. Additionally, the cell panel or membranes from these cells can be used for direct radioligand binding assays.

Assay panels are arranged so that agonist activity can be identified, quantitated and correlated with expression of each MC receptor. Automated assays using such panels are also envisioned, whereby the qualitative and quantitative detection of a reporter metabolite is detected in an array (such as a 96-well tissue culture plate) and the data collected and assembled into a computer data-base or other analytical program.

Antagonist activity is detected by a modification of the above assay. In this assay, the inhibition of production of an amount of a known receptor agonist, specific for each receptor, is assayed in the presence of a putative antagonist compound. Production of metabolite reporter molecules and their qualitative and quantitative detection is achieved as described above, and the specificity and potency of each antagonist compound characterized with regard to the degree of inhibition achieved for each receptor.

In view of the instant disclosure, MC-3/MC-4 receptor antagonists are expected to be useful to inhibit food intake in a hungry animal, and MC-3/MC-4 receptor agonists are expected to be useful to increase food intake in an animal. Alternative patterns of feeding behavior associated with different patterns of MC receptor agonist/antagonist activity can be determined using this assay.

Compounds having agonist or antagonist activity with the MC-3 or MC-4 receptors detected using this assay are further screened in vivo to determine whether the observed receptor binding activity results in modification of feeding behavior when administered to an animal. In these assays, the MC receptor binding compounds detected using the assay are administered intracerebroventricularly as described above in Example 5 to animals after an overnight fast, to waking animals, or to animals that are not otherwise primed to be hungry. Feeding and locomotor activity is monitored in these animals, and compounds affecting eating behavior (either by inhibiting feeding in otherwise hungry animals or stimulating feeding in otherwise sated animals) are selected for further development.

In addition, systemic administration of compounds found to be active by ICV administration assays is used to screen such compounds for the ability to cross the blood-brain barrier. Such compounds are also useful as templates for modifications aimed at increasing the availability of these compounds in the brain after systemic administration, for increasing bioactivity, or both.

It should be understood that the foregoing disclosure emphasizes certain specific embodiments of the invention and that all modifications or alternatives equivalent thereto are within the spirit and scope of the invention as set forth in the appended claims.

What we claim is:

1. A method for characterizing a compound as a mammalian MC-3 or MC-4 melanocortin receptor agonist that inhibits feeding behavior in an animal, the method comprising the steps of:

(a) providing a panel comprising a first mammalian cell comprising a recombinant expression construct encoding a mammalian melanocortin receptor that is the α-MSH receptor identified by Seq. ID Nos. 4 or 6, a second mammalian cell comprising a recombinant expression construct encoding a mammalian melanocortin receptor that is the ACTH receptor identified by Seq. ID Nos. 8 or 10, a third mammalian cell comprising a recombinant expression construct encoding a mammalian melanocortin receptor that is the MC-3 receptor identified by Seq. ID No. 12, a fourth mammalian cell comprising a recombinant expression construct encoding a mammalian melanocortin receptor that is the MC-4 receptor identified by Seq. ID No. 16, and a fifth mammalian cell comprising a recombinant expression construct encoding a mammalian melanocortin receptor that is the MC-5 receptor identified by Seq ID No. 18, wherein each mammalian cell expresses the melanocotin receptor encoded by the recombinant expression construct comprising tie cell;

(b) contacting each of the cells of the panel with a test compound to be characterized as an agonist of a mammalian melanocortin receptor;

(c) detecting binding of the test compound to each of the mammalian melanocortin receptors by assaying for a metabolite produced in the cells that bind the compound, wherein detection of the metabolite indicates that the test compound is an agonist of the melanocortin receptor;

(d) selecting the test compounds that are MC-3 or MC-4 melanocortin receptor agonists, and (e) determining whether the MC-3 or MC-4 melanocortin receptor agonist inhibits feeding behavior in an animal.

2. The method of claim 1, wherein the metabolite detected in subpart (c) is cyclic AMP.

3. The method of claim 1, each of the cells further comprising a recombinant expression construct encoding a cyclic AMP responsive element (CRE) transcription factor binding site operatively linked to a nucleic acid sequence encoding a protein capable of producing a detectable metabolite.

4. The method of claim 3, wherein the nucleic acid sequence encodes β-galactosidase.

5. The method of claim 3, wherein the recombinant expression construct is pCRE/β-galactosidase.

6. The method of claim 3, wherein the cells encoding each of the melanocortin receptors are cultured separately from each other and wherein the detectable metabolite produced by the protein encoded by the recombinant expression construct is produced by binding of the test compound to the mammalian melanocortin receptor encoded by each of the cells of the panel.

7. The method of claim 1 wherein the test compound is an agonist of the MC-3 mammalian melanocortin receptor.

8. The method of claim 1 wherein the test compound is an agonist of the MC-4 mammalian melanocortin receptor.

9. The method of claim 3 wherein the test compound is an agonist of the MC-3 mammalian melanocortin receptor.

10. The method of claim 3 wherein the test compound is an agonist of the MC-4 mammalian melanocortin receptor.

11. A method for characterizing a compound as a mammalian MC-3 or MC-4 melanocortin receptor antagonist that stimulates feeding behavior in an animal, the method comprising the steps of:

(a) providing a panel comprising a first mammalian cell comprising a recombinant expression construct encoding a mammalian melanocortin receptor that is the α-MSH receptor identified by Seq. ID Nos. 4 or 6, a second mammalian cell comprising a recombinant expression construct encoding a mammalian melanocortin receptor that is the ACTH receptor identified by Seq. ID Nos. 8 or 10, a third mammalian cell comprising a recombinant expression construct encoding a mammalian melanocortin receptor that is the MC-3 receptor identified by Seq. ID No. 12, a fourth mammalian cell comprising a recombinant expression construct encoding a mammalian melanocortin receptor that is the MC-4 receptor identified by Seq. ID No. 16, and a fifth mammalian cell comprising a recombinant expression construct encoding a mammalian melanocortin receptor that is the MC-5 receptor identified by Seq. ID No. 18, wherein each mammalian cell expresses the melanocortin receptor encoded by the recombinant expression construct comprising the cell, (b) contacting each of the cells of the panel with an agonist of the mammalian melanocortin receptor in an amount sufficient to produce a detectable amount of a metabolite produced in the cells that bind the agonist, in the presence or absence of a test compound to be characterized as an antagonist of a mammalian melanocortin receptor;

(c) detecting the amount of the metabolite produced in each cell in the panel in the presence of the test compound with the amount of the metabolite produced in each cell in the panel in the absence, wherein the test compound is determined to be an antagonist of melanocortin binding if the amount of the metabolite produced in the presence of the test compound is less than the amount of the metabolite produced in the absence of the test compound;

(d) selecting the test compounds that are MC-3 or MC-4 melanocortin receptor antagonist agonists, and (e) determining whether the MC-3 or MC-4 melanocortin receptor antagonist stimulates feeding behavior in an animal.

12. The method of claim 11, wherein the metabolite detected in subpart (c) is cyclic AMP.

13. The method of claim 11, each of the cells further comprising a recombinant expression construct encoding a cyclic AMP responsive element (CRE) transcription factor binding site operatively linked to a nucleic acid sequence encoding a protein capable of producing a detectable metabolite.

14. The method of claim 13, wherein the nucleic acid sequence encodes β-galactosidase.

15. The method of claim 13, wherein the recombinant expression construct is pCRE/β-galactosidase.

16. The method of claim 13, wherein the cells encoding each of the melanocortin receptors are cultured separately from each other and wherein the detectable metabolite produced by the protein encoded by the recombinant expression construct is produced by binding of the test compound to the mammalian melanocortin receptor encoded by each of the cells of the panel.

17. The method of claim 11 wherein the test compound is an antagonist of the MC-3 mammalian melanocortin receptor.

18. The method of claim 11 wherein the test compound is an antagonist of the MC-4 mammalian melanocortin receptor.

19. The method of claim 13 wherein the test compound is an antagonist of the MC-3 mammalian melanocortin receptor.

20. The method of claim 13 wherein the test compound is an antagonist of the MC-4 mammalian melanocortin receptor.

21. A biological screening panel for determining the mammalian melanocortin receptor agonist/antagonist profile of a test compound for the MC3 or MC-4 receptors, wherein the panel is used to identify compounds that modulate feeding behavior in an animal, the panel comprising a first mammalian cell consisting of a recombinant expression construct encoding a mammalian melanocortin receptor that is the MC-3 receptor identified by Seq. ID No. 12, and a second mammalian cell comprising a recombinant expression construct encoding a mammalian melanocortin receptor that is the MC-4 receptor identified by Seq. ID No. 16, wherein each mammalian cell expresses the melanocortin receptor encoded by the recombinant expression construct comprising the cell, and wherein compounds that modulate feeding behavior in a animal are selected from the MC-3/MC-4 mammalian melanocortin receptor agonists and antagonists.

* * * * *